(12) United States Patent
Kansal et al.

(10) Patent No.: US 9,056,838 B2
(45) Date of Patent: Jun. 16, 2015

(54) INTERMEDIATES AND PROCESSES FOR PREPARING TICAGRELOR

(75) Inventors: Vinod Kumar Kansal, Haryana (IN); Dhirenkumar Mistry, Gujarat (IN); Sanjay Vasoya, Gujarat (IN); Ghanshyam Pandey, Delhi (IN); Amit Taneja, Haryana (IN); Pramod Kadappa Shindey, Maharashtra (IN); Jiri Stohandl, Bobrova (CZ); Jaroslav Frantisek, Brno (CZ)

(73) Assignee: TEVA PHARMACEUTICAL INDUSTRIES LTD., Petah Tiqva (IL)

( * ) Notice: Subject to any disclaimer, the term of this patent is extended or adjusted under 35 U.S.C. 154(b) by 0 days.

(21) Appl. No.: 14/009,788

(22) PCT Filed: Apr. 6, 2012

(86) PCT No.: PCT/US2012/032497
§ 371 (c)(1),
(2), (4) Date: Dec. 16, 2013

(87) PCT Pub. No.: WO2012/138981
PCT Pub. Date: Oct. 11, 2012

(65) Prior Publication Data
US 2014/0094604 A1    Apr. 3, 2014

Related U.S. Application Data

(60) Provisional application No. 61/472,412, filed on Apr. 6, 2011, provisional application No. 61/490,371, filed on May 26, 2011.

(51) Int. Cl.
C07D 239/47   (2006.01)
C07D 487/04   (2006.01)
C07D 239/48   (2006.01)
B05B 1/16     (2006.01)
C07D 405/12   (2006.01)

(52) U.S. Cl.
CPC ............ *C07D 239/47* (2013.01); *C07D 487/04* (2013.01); *C07D 239/48* (2013.01); *B05B 1/1636* (2013.01); *C07D 405/12* (2013.01)

(58) Field of Classification Search
CPC ................................................. C07D 487/04
USPC ........................................................ 544/254
See application file for complete search history.

(56) References Cited

FOREIGN PATENT DOCUMENTS

| WO | WO 00/34283 | 6/2000 |
| WO | WO 01/92263 | 12/2001 |
| WO | WO 2009/139834 | 11/2009 |
| WO | WO 2010/030224 | 3/2010 |
| WO | WO 2011/017108 | 2/2011 |

OTHER PUBLICATIONS

International Search Report for International Application No. PCT/US2012/032497, mailed on Oct. 22, 2013.
Holschbach M.H. et al., Synthesis and evaluation of 7-amio-2(2(3)-furyl)-5-phenylethylamino-oxadolo[5,4-d] pyrimidines as potential A2A adenosine receptor antagonists for positron emission tomography (PET), European Journal of Medicinal Chemistry, Edition Scientifique Elsevier, Paris, FR, vol. 41, No. 1, Jan. 1, 2006, pp. 7-15, p. 8; compounds 5a, b.
Hoa Zhang et al., Synthesis and biological evaluation of ticagrelor derivatives as novel antiplatelet agents, Bioorganic & Medicinal Chemistry Letters, vol. 22, No. 11, Jun. 1, 2012, pp. 3598-3602, p. 3599; compound 11.

*Primary Examiner* — Brian McDowell
(74) *Attorney, Agent, or Firm* — Kenyon & Kenyon LLP

(57) ABSTRACT

The present invention is related to new intermediates and processes for preparing Ticagrelor disclosed in this patent application. One of the embodiments of the invention provides a process for preparing Ticagrelor of Formula I,

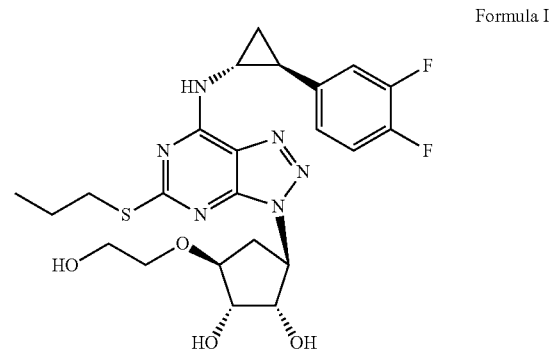

Formula I comprising coupling a compound of Formula VI,

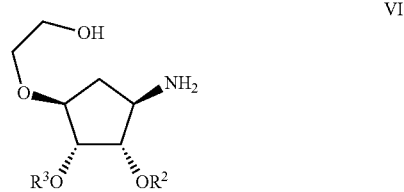

VI with a compound of Formula IX,

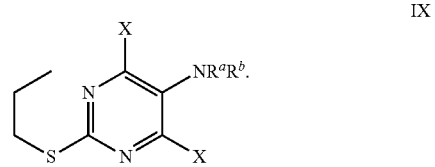

IX

8 Claims, No Drawings

INTERMEDIATES AND PROCESSES FOR PREPARING TICAGRELOR

REFERENCE TO RELATED APPLICATIONS

This patent application is the U.S. National Phase of International Application No. PCT/US2012/032497, filed on Apr. 6, 2012, and claims the benefits of U.S. Provisional Patent Application Nos. 61/472,412 filed Apr. 6, 2011 and 61/490,371 filed May 26, 2011, the disclosures of which are incorporated by reference herein.

FIELD OF THE INVENTION

The invention encompasses improved processes for preparing Ticagrelor and new intermediates useful for manufacturing Ticagrelor.

BACKGROUND OF THE INVENTION

Ticagrelor, (1S,2S,3R,5S)-3-[7-[[(1R,2S)-2-(3,4-difluorophenyl)cyclopropyl]-amino]-5-(propylthio)-3H-1,2,3-triazolo[4,5,d]pyrimidine-3-yl]-5-(2-hydroxyethoxy)-1,2-cyclopentanediol, has the following chemical structure:

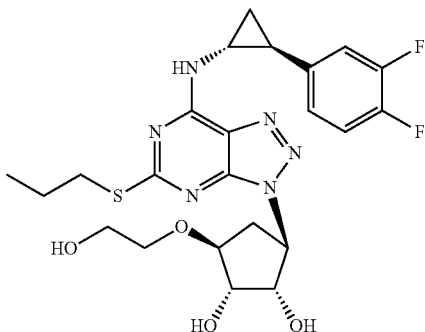 [SMILES: CCCSc1nc(N[C@@H]2C[C@H]2c2ccc(F)c(F)c2)c2nnn([C@@H]3C[C@H](OCCO)[C@@H](O)[C@H]3O)c2n1]

Ticagrelor is currently marketed in Europe under the trade name BRILIQUE™ BRILIQUE™ is purportedly a reversibly binding oral P2Y12 ADP receptor antagonist.

Ticagrelor can be obtained by a process as shown in the following scheme, as described in PCT Publication No. WO00034283:

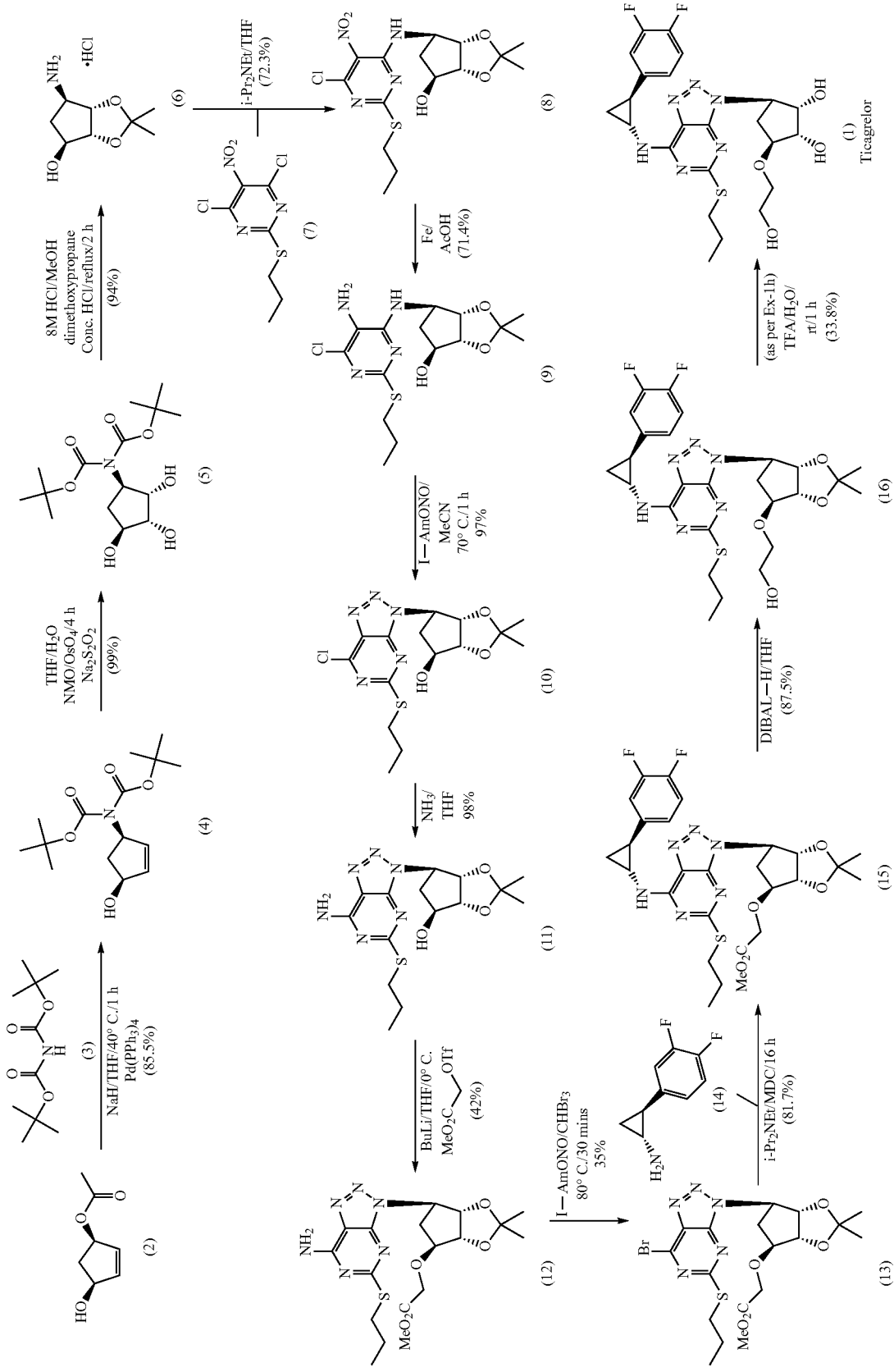

Although the process shown above produces the desired Ticagrelor product, several of the process steps incur significant problems that adversely affect the cost, yield, safety and environmental impact of the process as a whole. For example, in the process above, intermediates (9), (10), (12), (13), (15) and (16) are isolated as oils/liquids, making these intermediates much more difficult to handle and purify on a commercially useful scale. In some steps in the above process the conversion is low. For example, the coupling of intermediates (6) and (7) to prepare intermediate 8, results in a product that contains about 25-30% of a dimer byproduct that results from reaction of both chloro groups on intermediate (7). Another process step which does not proceed to completion is the reaction to form intermediate (12). This step has only about 40% conversion and produces a problematic triol byproduct, which can't be removed by crystallization because intermediate (12) is not a solid. Another potential problem with this step is that the methyl 2-(trifluoromethylsulfonyloxy)acetate reagent used therein is not commercially available and must be prepared using a reagent such as triflic anhydride, which is both expensive and hazardous. In addition, the final step of deprotection of the diol to produce Ticagrelor results in substantial racemization of the cyclopropyl amine.

There is a need in the art for improved processes for synthesizing Ticagrelor which are suitable for industrial use.

SUMMARY OF THE INVENTION

The present invention provides improved processes for preparing Ticagrelor. The invention also provides novel compounds. These compounds can be used as intermediates in the process for preparing Ticagrelor.

DETAILED DESCRIPTION OF THE INVENTION

The present invention encompasses improved processes for the preparation of Ticagrelor.

The term "acyl" means a radical of the general formula —C(O)—R, wherein —R is hydrogen or hydrocarbyl. When R is alkyl, the acyl group may be, for example, acetyl (—C(O)CH$_3$), propionyl (—C(O)Et), benzoyl (—C(O)C$_6$H$_5$), phenylacetyl (—C(O)CH$_2$C$_6$H$_5$).

The term "alkoxy/aryloxycarbonyl" means a radical of the general formula —OC(O)—R, wherein R is a hydrocarbyl group, such as a C$_{1-6}$ alkyl or a C$_{6-10}$ aryl, or a C$_{7-12}$ arylalkyl group for example carboethoxy (—CO$_2$Et), carbomethoxy (—CO$_2$Me) and benzyloxycarbonyl (—CO$_2$Bz).

The term "alkyl", by itself or as part of another substituent means, unless otherwise stated, a straight, branched or cyclic chain hydrocarbon radical, including di- and multi-radicals, having the number of carbon atoms designated (i.e. C$_1$-C$_6$ means one to six carbons) and includes straight, branched chain or cyclic groups. Examples include: methyl, ethyl, propyl, isopropyl, butyl, isobutyl, tert-butyl, pentyl, neopentyl, hexyl, cyclohexyl and cyclopropylmethyl.

Substituted alkyl means alkyl, as defined above, substituted by one, two or three substituents selected from halogen, =O, —OH, —O(C$_1$-C$_4$)alkyl, —OC(O)(C$_1$-C$_4$)alkyl, —C(O)(C$_1$-C$_4$)alkyl, =N(C$_1$-C$_4$)alkyl, =NOH, =NOC(O)(C$_1$-C$_4$)alkyl, —NH$_2$, —N(CH$_3$)$_2$, NHC(O)(C$_1$-C$_4$)alkyl, —CO$_2$H, —CO$_2$(C$_1$-C$_4$)alkyl, —CF$_3$, —CONH$_2$, —SO$_2$NH$_2$, —C(=NH)NH$_2$, —CN, =S, —SH, —S(C$_1$-C$_4$)alkyl, —SO(C$_1$-C$_4$)alkyl, SO$_2$(C$_1$-C$_4$)alkyl and —NO$_2$. Examples of substituted alkyls include, but are not limited to, 2,2-difluoropropyl, methoxymethyl, 2-carboxycyclopentyl and 3-chloropropyl.

The term "alkylene", by itself or as part of another substituent means, unless otherwise stated, a divalent straight, branched or cyclic chain hydrocarbon radical.

The term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers.

The term "amine" or "amino" refers to radicals of the general formula —NRR', wherein R and R' are independently selected from hydrogen or a hydrocarbyl radical, or wherein R and R' combined form a heterocycle. Examples of amino groups include: —NH$_2$, methyl amino, diethyl amino, anilino, benzyl amino, piperidinyl, piperazinyl and indolinyl.

The term "carbamyl" means the group —C(O)NRR', wherein R and R' are independently selected from hydrogen or a hydrocarbyl radical, or wherein R and R' combined form a heterocycle. Examples of carbamyl groups include: —C(O)NH$_2$ and —C(O)N(CH$_3$)$_2$.

The term "cycloalkyl" refers to ring-containing alkyl radicals. Examples include cyclohexyl, cyclopentyl, cyclopropyl methyl and norbornyl The term "heteroalkyl" by itself or in combination with another term means, unless otherwise stated, a stable straight or branched chain radical consisting of the stated number of carbon atoms and one or two heteroatoms selected from O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$CH$_2$—OH, —CH$_2$—CH$_2$—NH—CH$_3$, —CH$_2$—S—CH$_2$—CH$_3$, and —CH$_2$CH$_2$—S(O)—CH$_3$. Up to two heteroatoms may be consecutive, such as, for example, —CH$_2$—NH—OCH$_3$, or —CH$_2$—CH$_2$—S—S—CH$_3$.

The terms "halo" or "halogen" by themselves or as part of another substituent mean, unless otherwise stated, a fluorine, chlorine, bromine, or iodine atom, preferably, fluorine, chlorine, or bromine.

The term "aromatic" refers to a carbocycle or heterocycle having one or more polyunsaturated rings having aromatic character (4n+2) delocalized π (pi) electrons).

The term "aryl" employed alone or in combination with other terms, means, unless otherwise stated, a carbocyclic aromatic system containing one or more rings (typically one, two or three rings) wherein such rings may be attached together in a pendent manner, such as, for example, a biphenyl, or may be fused, such as, for example, naphthalene. Examples include phenyl; anthracyl; and naphthyl.

The term "aryl-(C$_1$-C$_3$)alkyl" means a radical wherein a C$_1$-C$_3$ alkylene chain is attached to an aryl group, e.g., —CH$_2$CH$_2$-phenyl. The term "substituted aryl-(C$_1$-C$_3$)alkyl" means an aryl-(C$_1$-C$_3$)alkyl radical in which the aryl group is substituted.

The term "heterocycle" or "heterocyclyl" or "heterocyclic" by itself or as part of another substituent means, unless otherwise stated, an unsubstituted or substituted, stable, mono- or multicyclic heterocyclic ring system which consists of carbon atoms and at least one heteroatom selected from N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom which affords a stable structure.

The term "heteroaryl" or "heteroaromatic" refers to a heterocycle having aromatic character. A polycyclic heteroaryl may include one or more rings which are partially saturated. Examples include tetrahydroquinoline and 2,3-dihydrobenzofuryl.

Examples of non-aromatic heterocycles include monocyclic groups such as, for example: pyrrolidine, pyrroline, imidazoline, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include: Pyridyl, pyrazinyl, pyrimidinyl, particularly 2- and 4-pyrimidinyl, pyridazinyl, thienyl, furyl, pyrrolyl, particularly 2-pyrrolyl, imidazolyl, thiazolyl, oxazolyl, pyrazolyl, particularly 3- and 5-pyrazolyl, isothiazolyl, 1,2,3-traizolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include: Indolyl, particularly 3-, 4-, 5-, 6- and 7-indolyl, indolinyl, quinolyl, tetrahydroquinolyl, isoquinolyl, particularly 1- and 5-isoquinolyl, 1,2,3,4-tetrahydroisoquinolyl, cinnolinyl, quinoxalinyl, particularly 2- and 5-quinoxalinyl, quinazolinyl, phthalazinyl, 1,8-naphthyridinyl, 1,4-benzodioxanyl, coumarin, dihydrocoumarin, benzofuryl, particularly 3-, 4-, 1,5-naphthyridinyl, 5-, 6- and 7-benzofuryl, 2,3-dihydrobenzofiryl, 1,2-benzisoxazolyl, benzothienyl, particularly 3-, 4-, 5-, 6- and 7-benzothienyl, benzoxazolyl, benzthiazolyl, particularly 2-benzothiazolyl and 5-benzothiazolyl, purinyl, benzimidazolyl, particularly 2-benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

The term "hydrocarbyl" refers to any moiety comprising only hydrogen and carbon atoms. Preferred hydrocarbyl groups are $(C_1-C_{12})$hydrocarbyl, e.g., $(C_1-C_7)$hydrocarbyl such as, for example, benzyl and $(C_1-C_6)$alkyl.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position.

In one embodiment, the present invention provides a novel compound of the following formula:

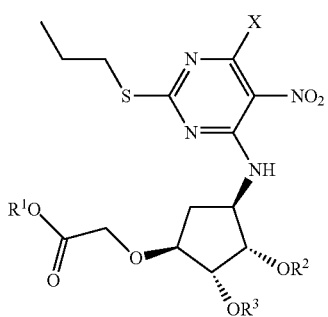

wherein, X is a halogen atom;
$R^1$ is —H, or —$C_1$-$C_{12}$ hydrocarbyl;
$R^2$ and $R^3$ are independently selected from —H, optionally substituted —$C_1$-$C_6$ alkyl, optionally substituted —$C_6$-$C_{18}$ aryl, optionally substituted —$C_6$-$C_{12}$aryl-$(C_1$-$C_3)$alkyl, optionally substituted —Si$(C_{1-6}$ alkyl$)_3$, optionally substituted —C(═O)—$C_{1-6}$alkyl, and optionally substituted —C(═O)—O$C_{1-6}$ alkyl; or
$R^2$ and $R^3$ form, together with the oxygen atoms to which they are attached, a 5 to 10 membered heterocyclic ring, which heterocyclic ring is optionally substituted with 1, 2 or 3 substituents independently selected from a $C_{1-8}$ straight-chain hydrocarbyl group, a $C_{3-8}$ branched or cyclic hydrocarbyl group, and a $C_{3-8}$ carbocyclic ring A; wherein said $C_{3-8}$ carbocyclic ring A is bonded to the 5 to 10 membered heterocyclic ring via:

a) a single bond:

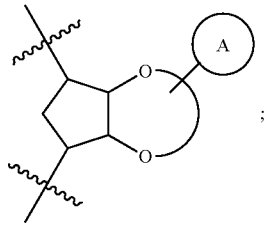

or
b) via a spiro fusion:

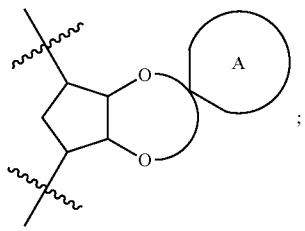

wherein the carbocyclic ring A is optionally substituted by 1, 2 or three substituents independently selected from —$C_1$-$C_6$ alkyl, such as, for example, methyl, ethyl, propyl, isopropyl, butyl, isobutyl, or t-butyl; —$C_6$-$C_{10}$ aryl, such as, for example, phenyl, tolyl or naphthyl and —$C_6$-$C_{10}$ aryl-$C_1$-$C_3$ alkyl, such as, for example, benzyl, 1-phenylethyl, 2-phenylethyl, or α or β naphthylmethyl.

According to some embodiments, $R^2$ and $R^3$ are independently selected from —H, optionally substituted —Si$(C_{1-6}$alkyl$)_3$, optionally substituted —C(═O)—$C_{1-6}$alkyl, and optionally substituted —C(═O)—O$C_{1-6}$ alkyl; or $R^2$ and $R^3$ can together with the oxygen atoms to which they are attached form a heterocyclic ring as shown below:

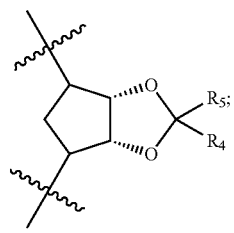

wherein $R^4$ and $R^5$ are independently selected from —H, —$C_{1-6}$ alkyl, and —$C_{6-10}$ aryl; or $R^4$ and $R^5$ together with the carbon atom to which they are attached form a 5 to 6 membered spiro-fused carbocyclic ring, which is optionally substituted by 1, 2 or three substituents independently selected from —$C_1$-$C_6$ alkyl, such as, for example, methyl, ethyl, propyl, isopropyl, butyl, isobutyl, or t-butyl; —$C_6$-$C_{10}$ aryl, such as, for example, phenyl, tolyl or naphthyl and —$C_6$-$C_{10}$ aryl-$C_1$-$C_3$ alkyl, such as, for example, benzyl, 1-phenylethyl, 2-phenylethyl, or α or β naphthylmethyl.

According to some embodiments, $R^2$ and $R^3$, together with the atoms to which they are attached, form an alkylidene ring, such as, for example, a methylidene or isopropylidene ring, or an alkoxymethylidene ring such as, for example, ethoxymethylidene; each optionally substituted with 1, 2 or 3 substituents independently selected from —$C_1$-$C_8$ alkyl or —$C_6$-$C_8$ aryl. In some embodiments, $R^2$ and $R^3$ together can form an alkylidene group such as a methylidene or isopropylidene group, or an alkoxymethylidene group such as, for example, ethoxymethylidene; each optionally substituted with 1, 2 or 3 substituents independently selected from —$C_1$-$C_8$ alkyl or —$C_6$-$C_8$ aryl. According to some embodiments, a spiro fused system formed by $R^4$ and $R^5$ can be, for example:

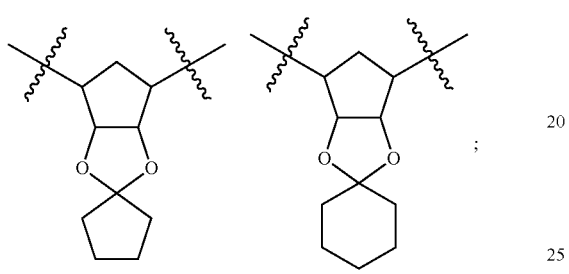

wherein, in the partial structures above, the two oxygen atoms are understood to correspond to the two oxygen atoms to which the $R^2$ and $R^3$ substituents are attached.

According to some embodiments, $R^1$ is —H, a $C_1$-$C_6$ alkyl group, such as, for example, methyl, ethyl, propyl, isopropyl, butyl, isobutyl, or t-butyl; a —$C_6$-$C_{10}$aryl group, such as, for example, phenyl, alpha naphthyl or beta naphthyl; or a $C_6$-$C_{10}$aryl-($C_1$-$C_2$)alkyl, such as, for example, benzyl, phenylethyl or naphthylmethyl.

According to some embodiments, one or both of $R^2$ and $R^3$ are protecting groups selected from Si($C_{1-6}$alkyl)$_3$, C(=O)—$C_{6-10}$ aryl, C(=O)—O$C_{1-6}$ alkyl, —C(O)OCH$_2$($C_6$-$C_{10}$)aryl and substituted —C(O)OCH$_2$($C_6$-$C_{10}$)aryl. —Si($C_{1-6}$alkyl)$_3$, such as, for example, trimethylsilyl and tert-butyldimethylsilyl; —C(=O)—$C_{1-6}$alkyl, such as, for example, acetyl and propionyl; —C(=O)—$C_{1-6}$ aryl, such as, for example, benzoyl; —C(=O)—O$C_{1-6}$ alkyl, such as, for example, —C(=O)OCH$_3$, —C(=O)OEt and —C(=O)Ot-Bu; and —C(O)OCH$_2$($C_6$-$C_{10}$)aryl such as C(O)Obenzyl.

When $R^2$ and $R^3$ are protecting groups, these groups can typically be added and removed using conventional protecting group methodology, for example, as described in "Protective Groups in Organic Chemistry," edited by J W F McOmie, Plenum Press (1973), and "Protective Groups in Organic Synthesis", 2nd edition, T W Greene & P G M Wutz, Wiley-Interscience (1991).

In certain specific embodiments, the present invention provides the novel compounds, ethyl(2-((3aR,4S,6R,6aS)-4-(6-chloro-5-nitro-2-(propylthio)pyrimidin-4-ylamino)-tetrahydro-2,2-dimethyl-3aH-cyclopenta[d][1,3]dioxol-6-yloxy)acetate (Compound 7); ethyl (2-((1S,2S,3S,4R)-4-(6-chloro-5-nitro-2-(propylthio)pyrimidin-4-ylamino)-2,3-dihydroxycyclopentyloxy)acetate (Compound 7a); and ethyl 2-((3aS,4R,6S,6aR)-4-(6-chloro-5-nitro-2-(propylthio)pyrimidin-4-ylamino)tetrahydro-3aH-spiro[cyclopenta[d][1,3]dioxole-2,1'-cyclopentane]-6-yloxy)acetate (Compound 7b); as depicted in the structure diagrams below:

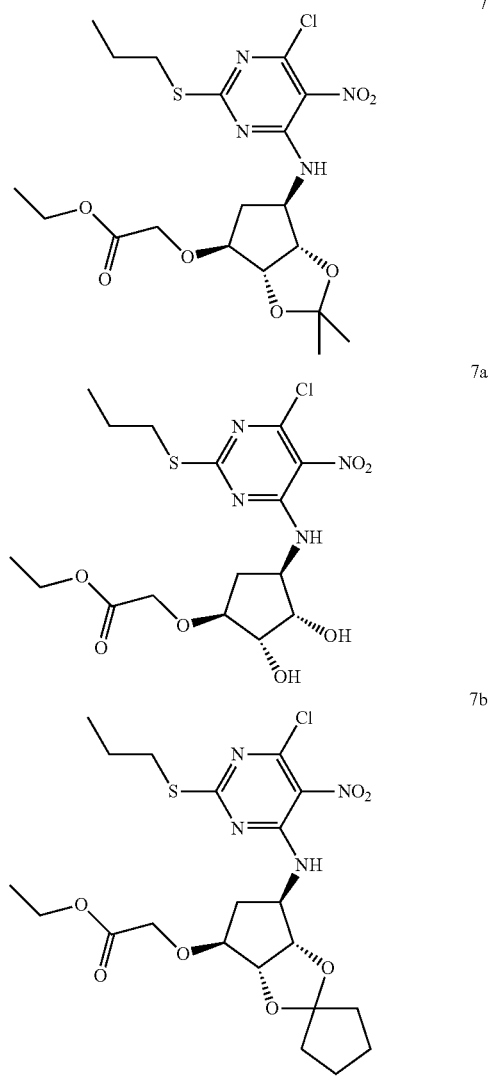

In another embodiment, the present invention provides a novel compound 8 of the following formula:

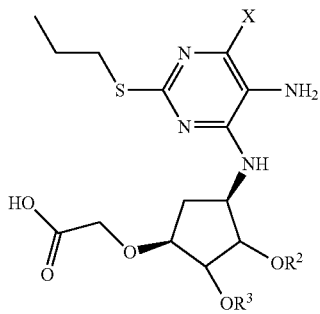

wherein X is a halogen atom, and $R^2$, and $R^3$ are defined as above.

In certain other specific embodiments, the present invention provides the novel compounds, 2-({3aR,4S,6R,6aS)-6-{[5-amino-6-chloro-2-(propylthio)-4-pyrimidinylamino}-2,2-dimethyltetrahydro-3aH-cyclopenta[d][1,3]dioxol-4-yl)oxy]-1-acetic acid (Compound 8a); and 2-((3aR,4S,6R,6aS)-4-(5-amino-6-chloro-2-(propylthio)pyrimidin-4-ylamino) tetrahydro-3aH-spiro[cyclopenta[d][1,3]dioxole-2,1'-cyclopentane]-6-yloxy)acetic acid (Compound 8a'); shown in the structure diagrams below:

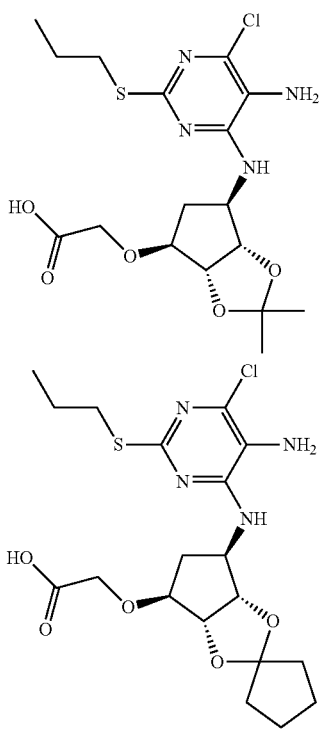

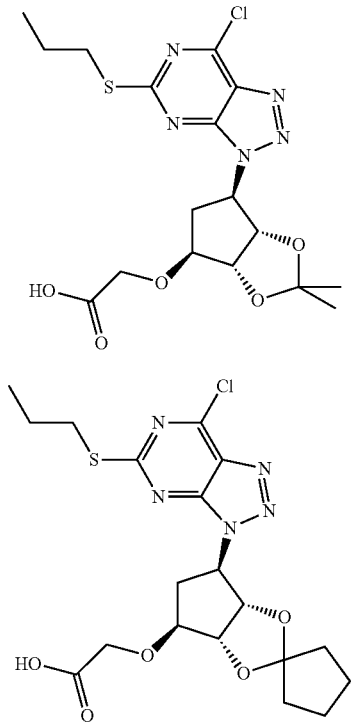

In other specific embodiments, the present invention provides the novel compounds, 2-({3aR,4S,6R,6aS)-6-[7-chloro-5-(propylthio)-3H-[1,2,3]triazolo[4,5-d]pyrimidin-3-yl]-2,2-dimethyltetrahydro-3aH-cyclopenta[d][1,3]dioxol-4-yl}oxy)-1-acetic acid (Compound 9a); and 2-((3aR,4S,6R,6aS)-4-(7-chloro-5-(propylthio)-3H-[1,2,3]triazolo[4,5-d]pyrimidin-3-yl)tetrahydro-3aH-spiro[cyclopenta[d][1,3]dioxole-2,1'-cyclopentane]-6-yloxy)acetic acid (Compound 9a') shown below:

In one embodiment, the present invention provides an isolated compound and its salts, having the following formula:

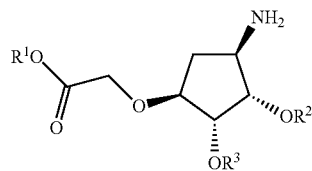

wherein $R^1$, $R^2$ and $R^3$ are as defined as above.

In another specific embodiment, the present invention provides isolated compounds ethyl 2-((3aR,4S,6R,6aS)-6-amino-2,2-dimethyltetrahydro-3aH-cyclopenta[d][1,3]dioxol-4-yloxy)acetate and ethyl 2-((3aR,4S,6R,6aS)-4-aminotetrahydro-3aH-spiro[cyclopenta[d][1,3]dioxole-2,1'-cyclopentane]-6-yloxy)acetate having the following two formulae:

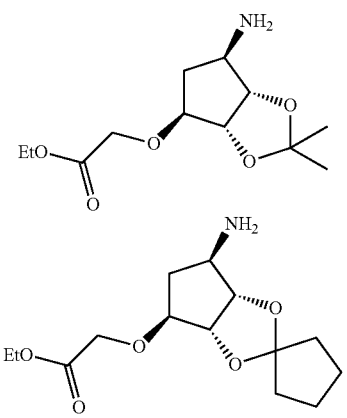

In one embodiment, the present invention provides a novel compounds, having the following formulae:

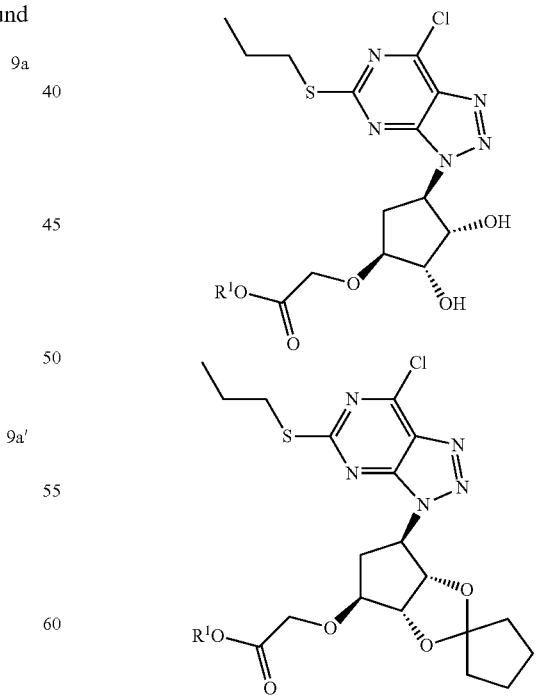

wherein, $R^1$ is as defined above.

In certain specific embodiments, the present invention provides the novel compounds, ethyl (2-((1S,2S,3S,4R)-4-(7-chloro-5-(propylthio)-3H-[1,2,3]triazolo[4,5-d]pyrimidin-3- yl)-2,3-dihydroxycyclopentyloxy)acetate (Compound 9b); and ethyl 2-((3aS,4R,6S,6aR)-4-(7-chloro-5-(propylthio)-3H-[1,2,3]triazolo[4,5-d]pyrimidin-3-yl)-tetrahydro-3aH-spiro[cyclopenta[d][1,3]dioxole-2,1'-cyclopentane]-6-yloxy)acetate (Compound 9b'), as shown in the structure diagrams below:

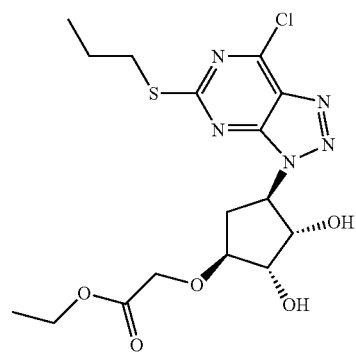

9b

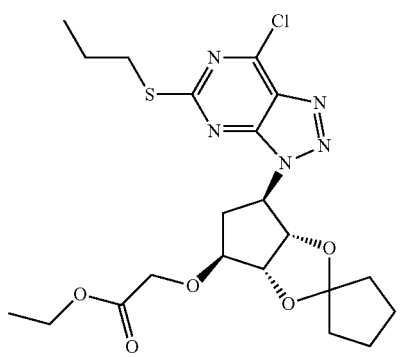

9b'

In another embodiment, the present invention provides a novel compounds, having the following formula:

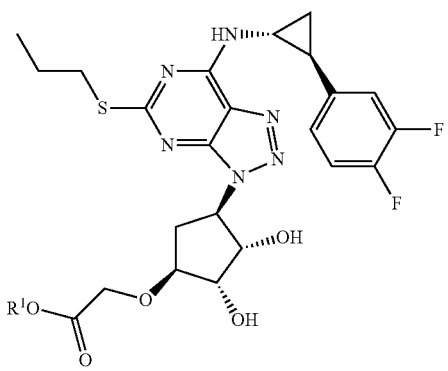

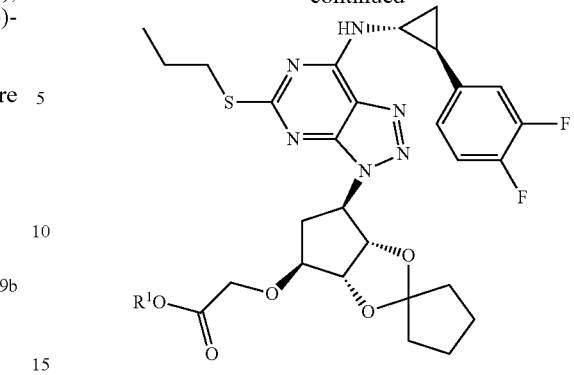

wherein, $R^1$ is defined as above.

In certain specific embodiments, the present invention provides the novel compounds, ethyl[3aR-[3aα,4α,6α(1R*,2S*),6aα]]-[[6-[7-[[2-(3,4-difluorophenyl)cyclopropyl]amino]-5-(propylthio)-3H-1,2,3-triazolo[4,5-d]-pyrimidin-3-yl]-2,3-dihydroxy-cyclopentyloxy)acetate (Compound 11a); and ethyl 2-((3aS,4R,6S,6aR)-4-(7-((1R,2S)-2-(3,4-difluorophenyl)cyclopropylamino)-5-(propylthio)-3H-[1,2,3]triazolo[4,5-d]-pyrimidin-3-yl)tetrahydro-3aH-spiro[cyclopenta[d][1,3]dioxole-2,1'-cyclopentane]-6-yloxy)acetate (Compound 11b), as shown in the structure diagrams below:

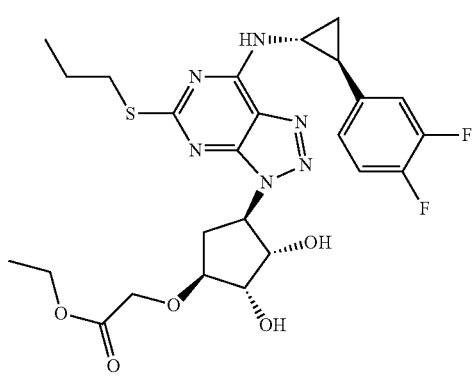

11a

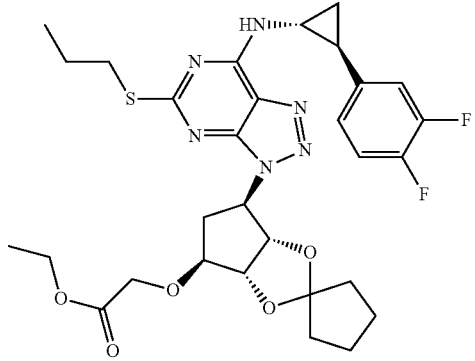

11b

Any of the above mentioned compounds can be used as an intermediate in the process for preparing Ticagrelor.

In another embodiment, the present invention encompasses a process for preparing Ticagrelor by preparing any one of the above mentioned compounds and further converting it to Ticagrelor, for example according to the process described below. In another embodiment, the present invention provides improved processes for preparing Ticagrelor, according to the following Schemes.

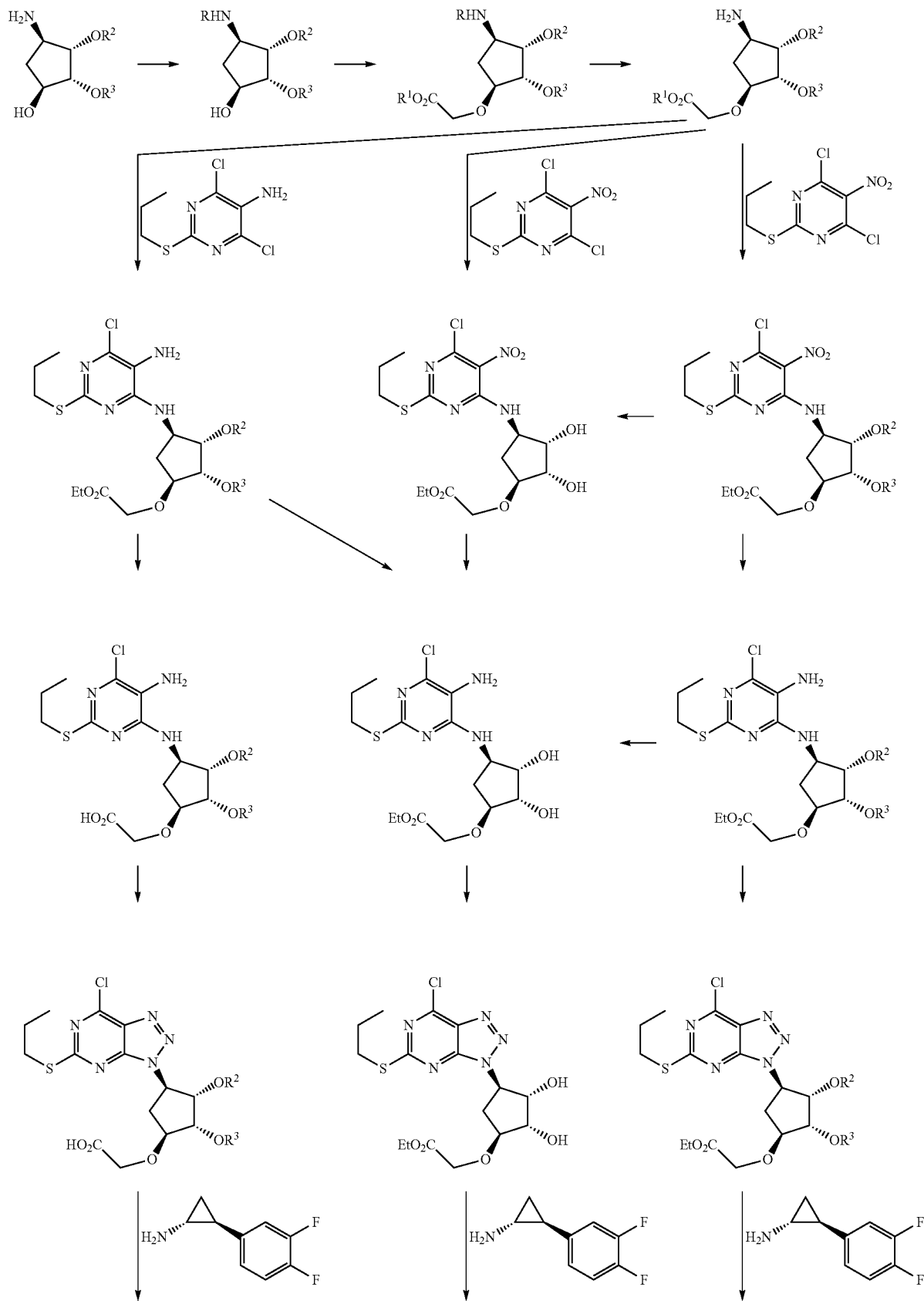
Scheme A 17 18
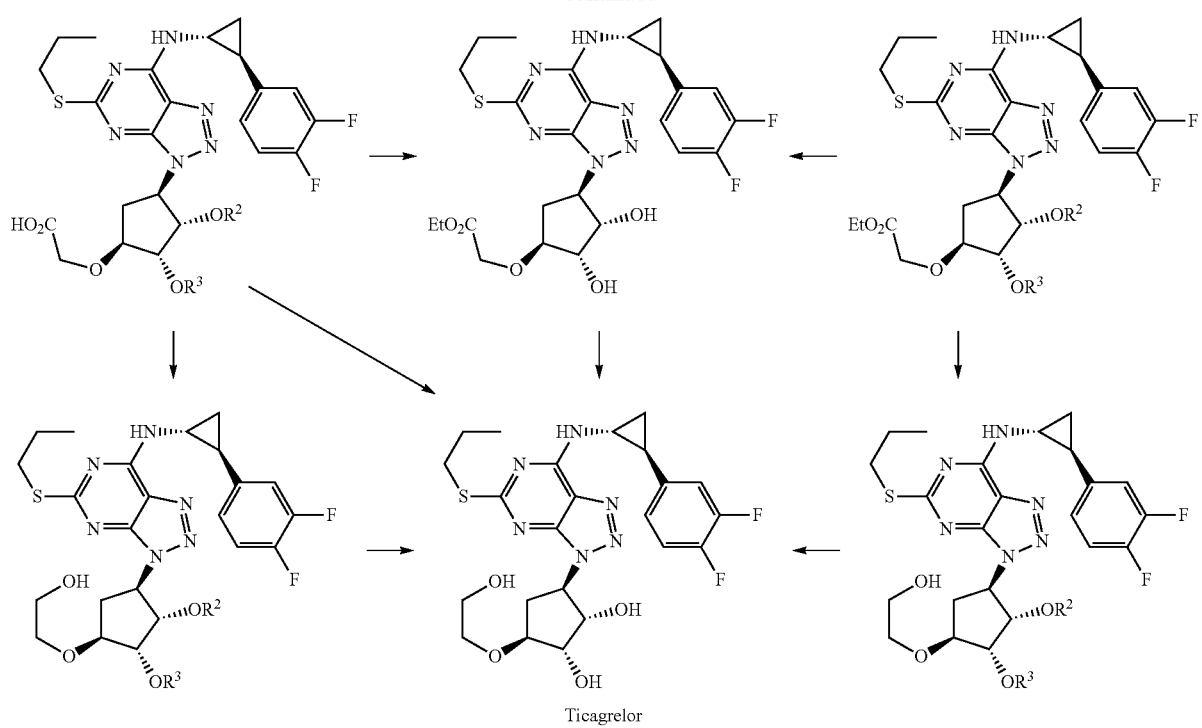
-continued
Ticagrelor
Reaction Scheme 1:
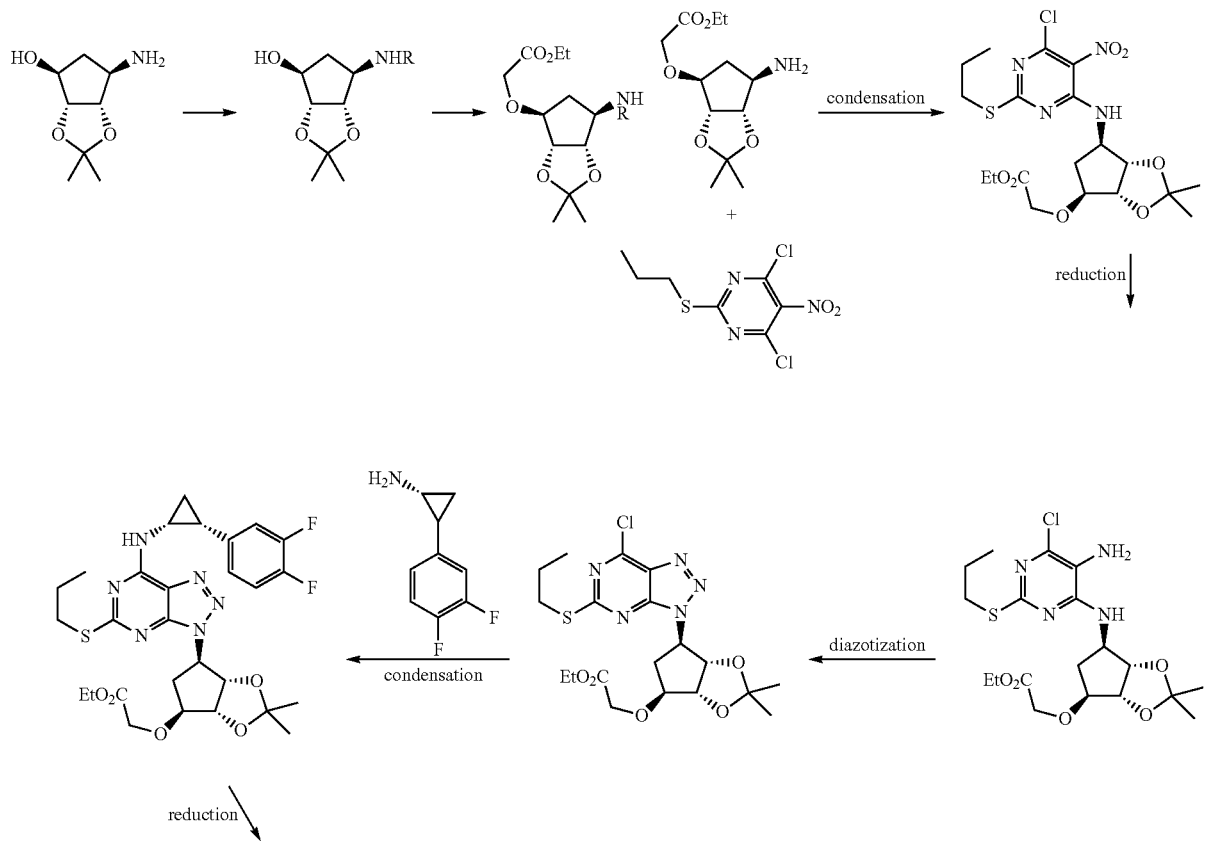

-continued
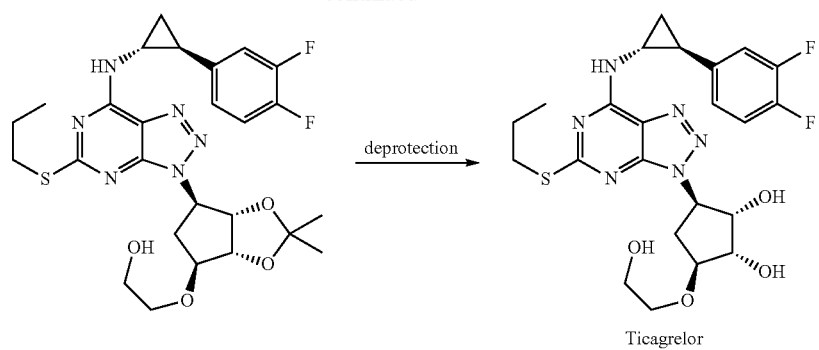
Scheme 2
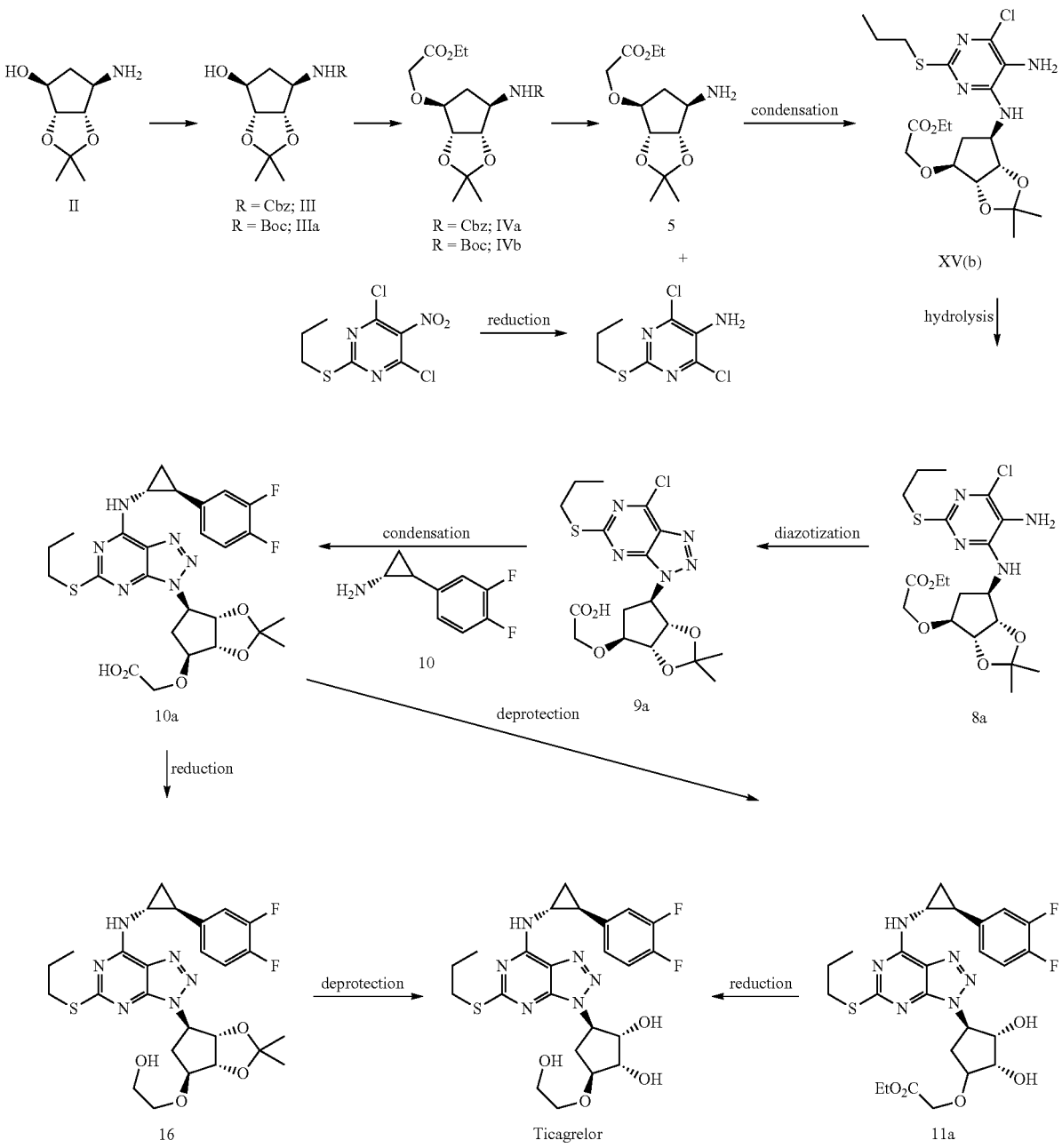

Scheme 2a

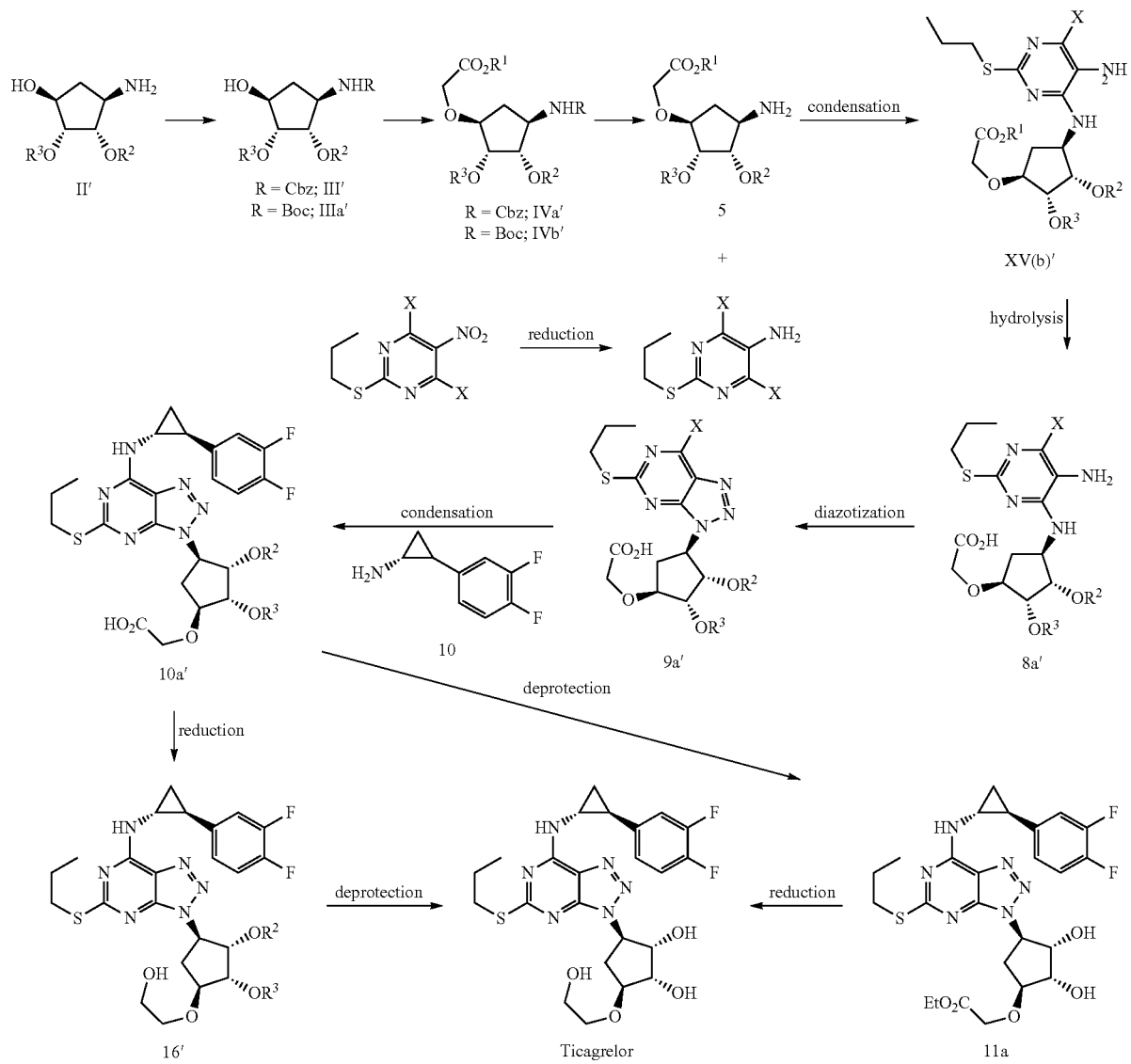

According to certain specific embodiments, Ticagrelor can be obtained by a process as shown in Schemes 2 and 2a above. The process is high yielding and several core intermediates, e.g., intermediates 8a, 9a and 10a are solid materials that are readily purified on commercially useful scales.

The invention provides novel compounds of Formula 8a':

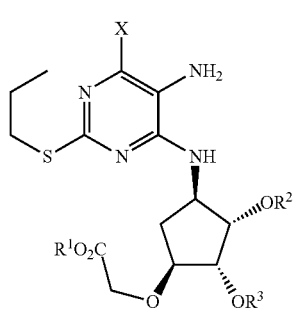

wherein, $R^1$ is as described above; X is a leaving group that can be removed or substituted by conventional methods; and $R^2$ and $R^3$ are as defined above.

According to some embodiments, the leaving group X is selected, for example, from halogens, such as, for example, —Cl, —Br and —I.

The invention also provides compounds according to Formulae 9a and 9a':

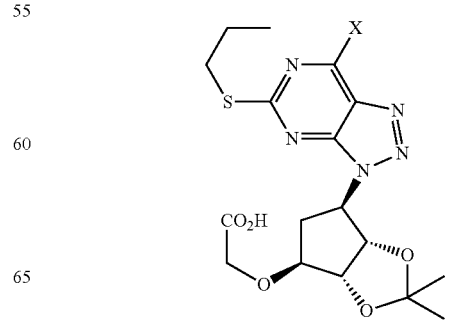

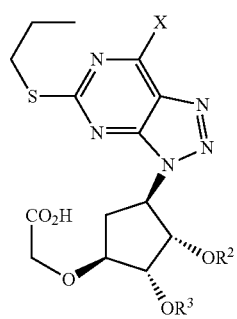

9a'

In certain specific embodiments, the present invention provides the novel compounds, ethyl 2-((3aR,4S,6R,6aS)-6-(5-amino-6-chloro-2-(propylthio)pyrimidin-4-ylamino)-2,2-dimethyltetrahydro-3aH-cyclopenta[d][1,3]dioxol-4-yloxy)acetate:

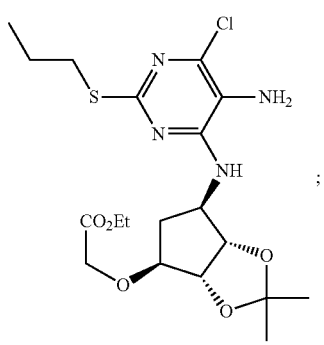

XV(b)

2-((3aR,4S,6R,6aS)-6-(5-amino-6-chloro-2-(propylthio)pyrimidin-4-ylamino)-2,2-dimethyltetrahydro-3aH-cyclopenta[d][1,3]dioxol-4-yloxy)acetic acid:

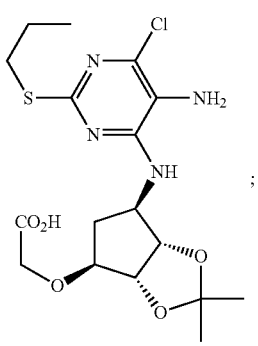

8a 2-((3aR,4S,6R,6aS)-6-(7-chloro-5-(propylthio)-3H-[1,2,3]triazolo[4,5-d]pyrimidin-3-yl)-2,2-dimethyltetrahydro-3aH-cyclopenta[d][1,3]dioxol-4-yloxy)acetic acid:

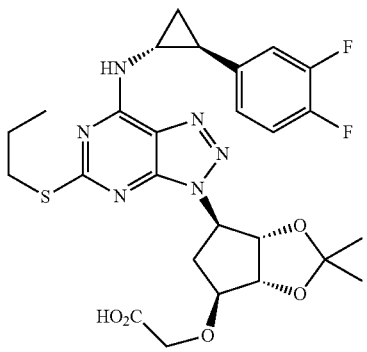

9a and
2-((3aR,4S,6R,6aS)-6-(7-((1R,2S)-2-(3,4-difluorophenyl)cyclopropylamino)-5-(propylthio)-3H-[1,2,3]triazolo[4,5-d]pyrimidin-3-yl)-2,2-dimethyltetrahydro-3aH-cyclopenta[d][1,3]dioxol-4-yloxy)acetic acid:

According to another embodiment, the invention provides a process of preparing Ticagrelor, said process comprising coupling the compound according to Formula 5:

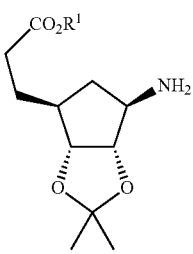

5 with a compound of the following formula:

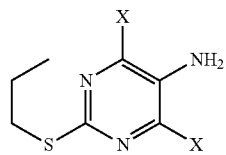

wherein X is a leaving group, for example, 4,6-dichloro-2-(propylthio)pyrimidin-5-amine, to form a compound of Formula 8a, as described above; wherein $R^1$ is as described above; and X is a leaving group;

hydrolyzing the compound of Formula 8a, wherein R¹ is —C₁-C₁₂ hydrocarbyl, to produce a compound of Formula 8a, wherein R¹ is —H;

diazotizing the compound of Formula 8a (wherein R¹ is —H) to produce a compound of Formula 9a, as described above;

reacting the compound of Formula 9a with (1R,2S)-2-(3,4-difluorophenyl)cyclopropanamine to produce the compound, 2-((3aR,4S,6R,6aS)-6-(7-((1R,2S)-2-(3,4-difluorophenyl)cyclopropylamino)-5-(propylthio)-3H-[1,2,3]triazolo[4,5-d]pyrimidin-3-yl)-2,2-dimethyltetrahydro-3aH-cyclopenta[d][1,3]dioxol-4-yloxy)acetic acid:

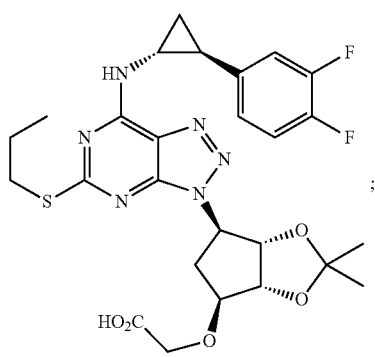 [SMILES: CCCSc1nc(N[C@@H]2C[C@H]2c2ccc(F)c(F)c2)c2nnn([C@@H]3C[C@H](OCC(=O)O)[C@H]4OC(C)(C)O[C@H]43)c2n1]
;

reducing the compound above to produce the compound 16, 2-((3aR,4S,6R,6aS)-6-(7-((1R,2S)-2-(3,4-difluorophenyl)cyclopropylamino)-5-(propylthio)-3H-[1,2,3]triazole[4,5-d]pyrimidin-3-yl)-2,2-dimethyltetrahydro-3aH-cyclopenta[d][1,3]dioxol-4-yloxy)ethanol:

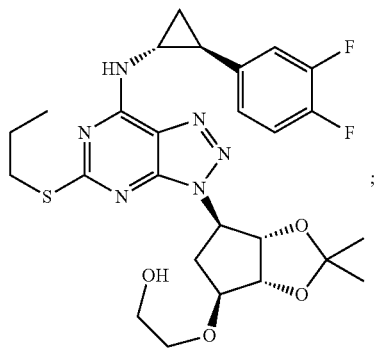 [SMILES: CCCSc1nc(N[C@@H]2C[C@H]2c2ccc(F)c(F)c2)c2nnn([C@@H]3C[C@H](OCCO)[C@H]4OC(C)(C)O[C@H]43)c2n1]
;

and deprotecting compound 16 to produce Ticagrelor; or alternatively; deprotecting the compound 2-((3aR,4S,6R,6aS)-6-(7-((1R,2S)-2-(3,4-difluorophenyl)cyclopropylamino)-5-(propylthio)-3H-[1,2,3]triazolo[4,5-d]pyrimidin-3-yl)-2,2-dimethyltetrahydro-3aH-cyclopenta[d][1,3]dioxol-4-yloxy)acetic acid to produce the ester compound 11a, ethyl 2-((1S,2S,3S,4R)-4-(7-((1R,2S)-2-(3,4-difluorophenyl)cyclopropylamino)-5-(propylthio)-3H-[1,2,3]triazolo[4,5-d]pyrimidin-3-yl)-2,3-dihydroxycyclopentyloxy)acetate:

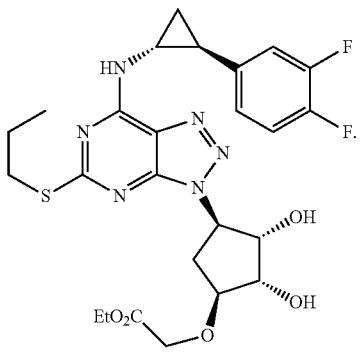 [SMILES: CCCSc1nc(N[C@@H]2C[C@H]2c2ccc(F)c(F)c2)c2nnn([C@@H]3C[C@H](OCC(=O)OCC)[C@@H](O)[C@H]3O)c2n1]

and reducing that ester compound 11a to produce Ticagrelor.

The step of hydrolyzing a Formula XVb ester compound to a Formula 8a acid compound, may be carried out using a suitable base, and is preferably carried out in a suitable solvent. Suitable base can be alkali metal hydroxide or carbonates or bicarbonates Suitable solvents include polar solvents, such as, for example C₁-C₆ alcohols, e.g., methanol, ethanol, propanol and isopropanol, acetonitrile, tetrahydrofuran, NMP, mixtures of these solvents, and mixtures thereof with water.

The step of diazotizing the Formula 8a acid can be carried out, for example, by reacting the Formula 8a acid with a suitable diazotizing agent, preferably, in the presence of a suitable solvent. Suitable diazotizing agents include, for example sodium nitrite and isoamyl nitrite. Suitable solvents for carrying out this reaction include polar organic solvents such as, for example, methanol, ethanol, or acetonitrile, mixtures thereof; and mixtures thereof with water and water alone.

The step of coupling the Formula 9a with (1R,2S)-2-(3,4-difluorophenyl)cyclopropanamine can be carried out, for example, by reacting the two compounds in the presence of a suitable base, preferably in the presence of a suitable solvent. Suitable bases include organic bases, such as triethyl amine and diisopropyl ethyl amine and inorganic bases, such as, for example sodium bicarbonate, sodium carbonate, potassium bicarbonate and potassium carbonate. Suitable solvents include solvents that are inert to the reaction conditions and in which the reagents are soluble. The reaction can be carried out in a single phase in solvents including halogenated solvents such as, for example, dichloromethane or dichloroethane, ethers such as t-butylmethyl ether or THF, and other suitably inert organic solvents. The reaction can also be carried out in a two-phase reaction, i.e., with water and a suitable organic solvent such as toluene or THF.

Conversion of the compound 2-((3aR,4S,6R,6aS)-6-(7-((1R,2S)-2-(3,4-difluoro-phenyl)cyclopropylamino)-5-(propylthio)-3H-[1,2,3]triazolo[4,5-d]pyrimidin-3-yl)-2,2-dimethyltetrahydro-3aH-cyclopenta[d][1,3]dioxol-4-yloxy)acetic acid (10a) to Ticagrelor can be carried out by a reaction with a suitable reducing agent. Suitable reducing agents include hydride reagents, for example LAH, NaBH₄—BF₃.OEt₂ or Redal; diborane or SmI₂, followed by deprotecting the acetonide in acidic conditions. Alternatively, 10a is deprotected in acidic conditions to give the compound 11a, followed by the reduction of acid group using suitable reducing agents include, hydride reagents, for example LAH, NaBH₄—BF₃.OEt₂ or Redal; diborane or SmI₂.

Reaction Scheme 3:
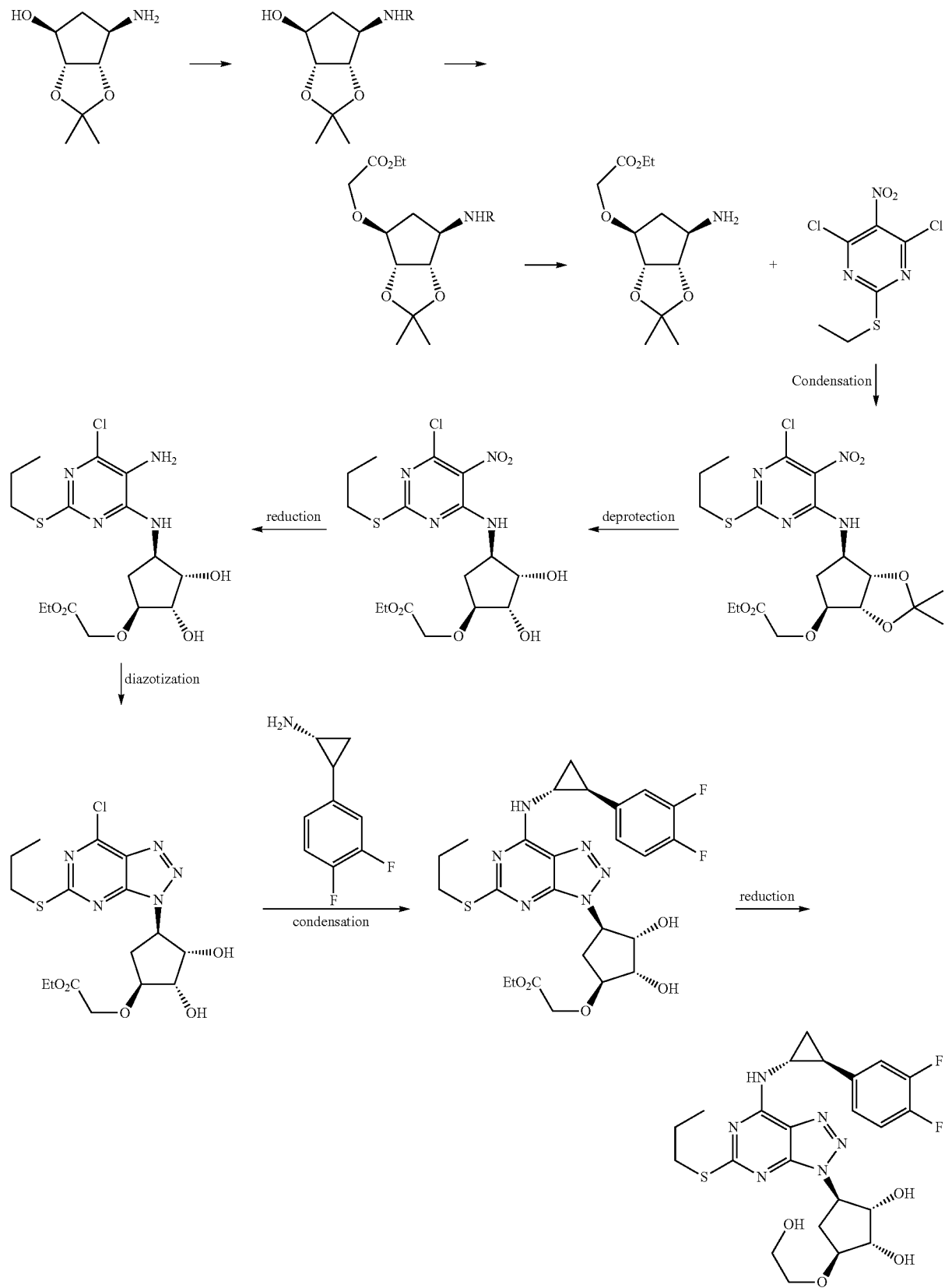

Reaction Scheme 4:
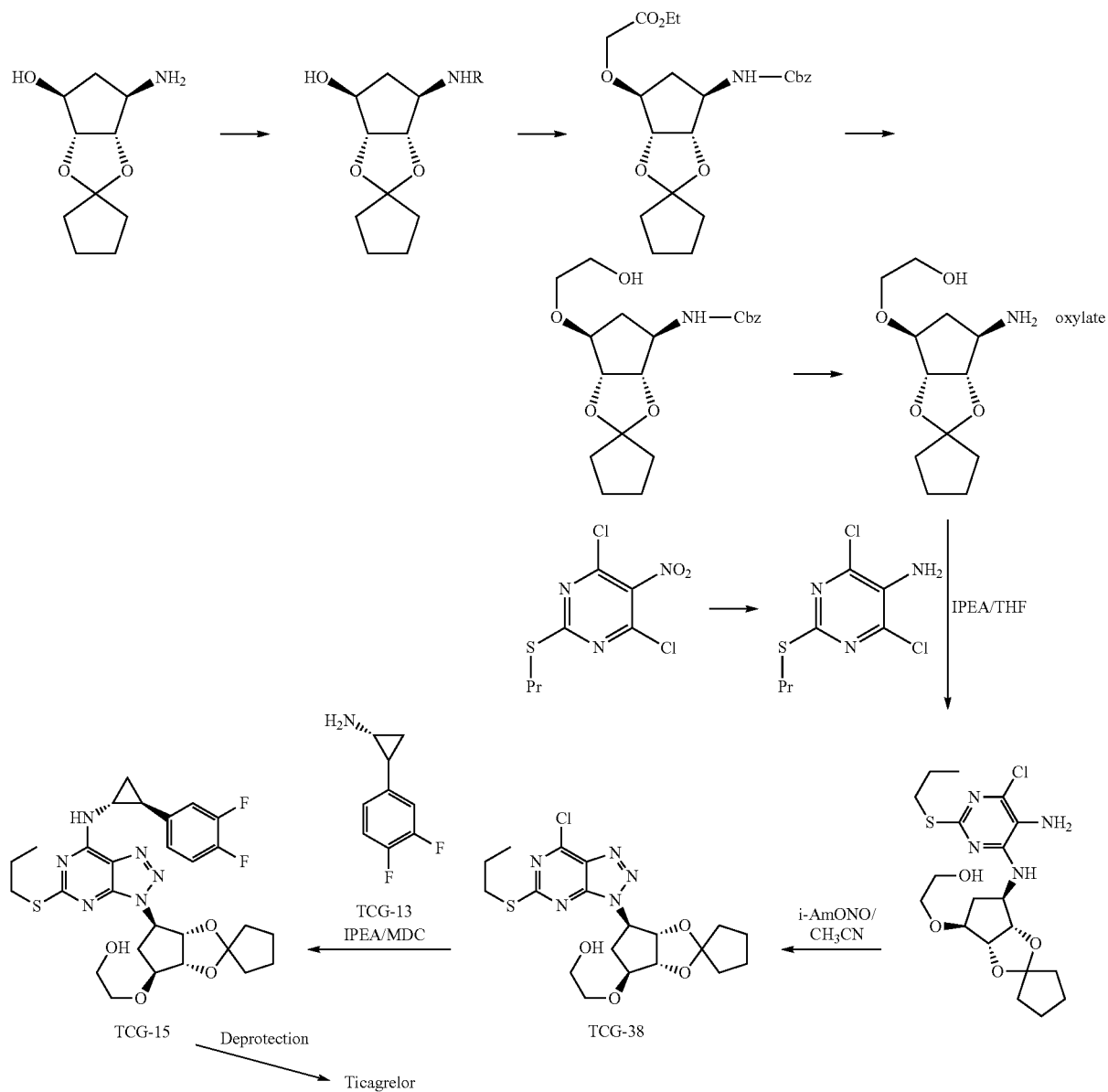
The present invention also provides the following process for preparation of Ticagrelor, represented by two following reaction schemes 5a, 5b and 6:

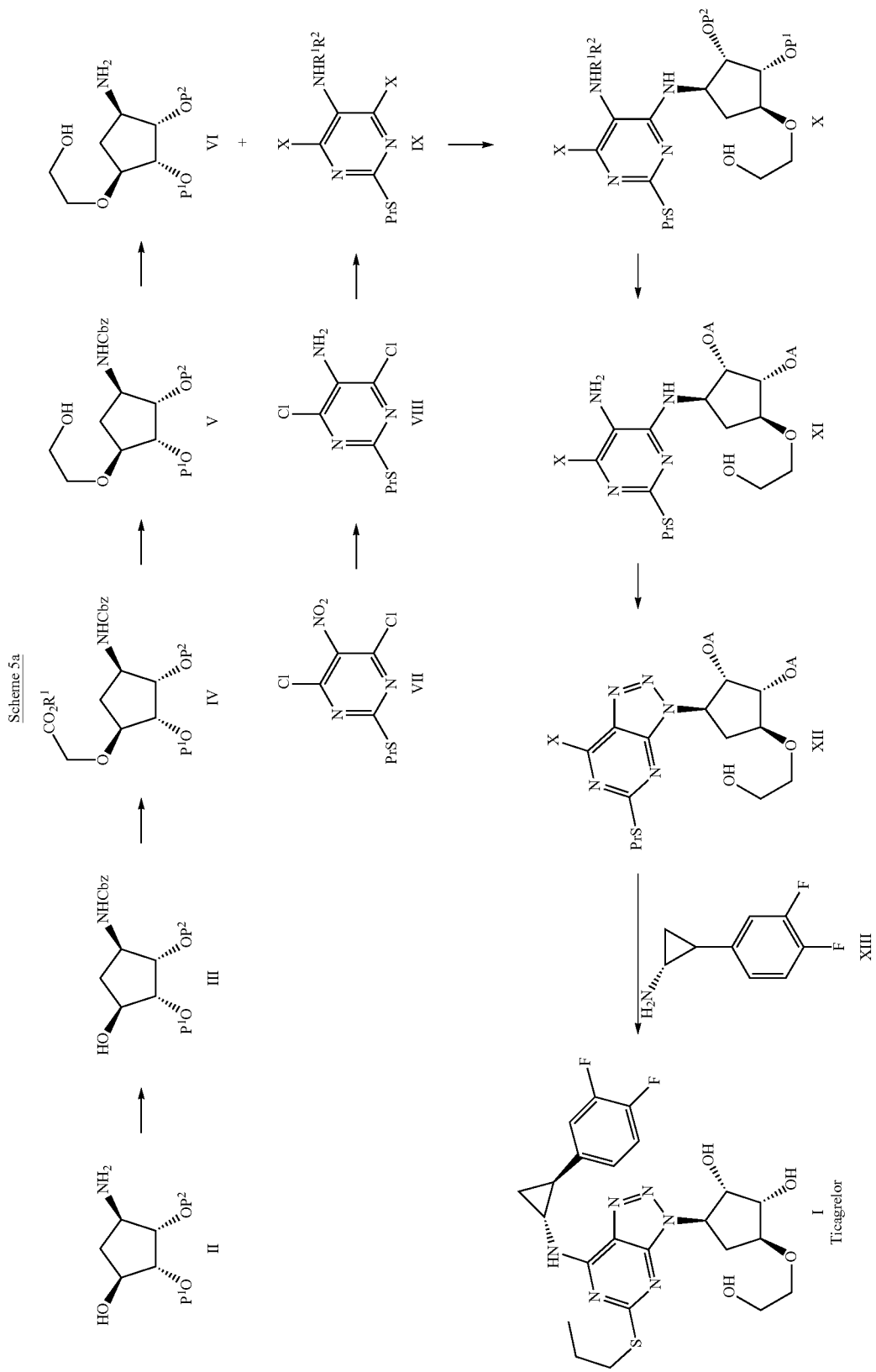

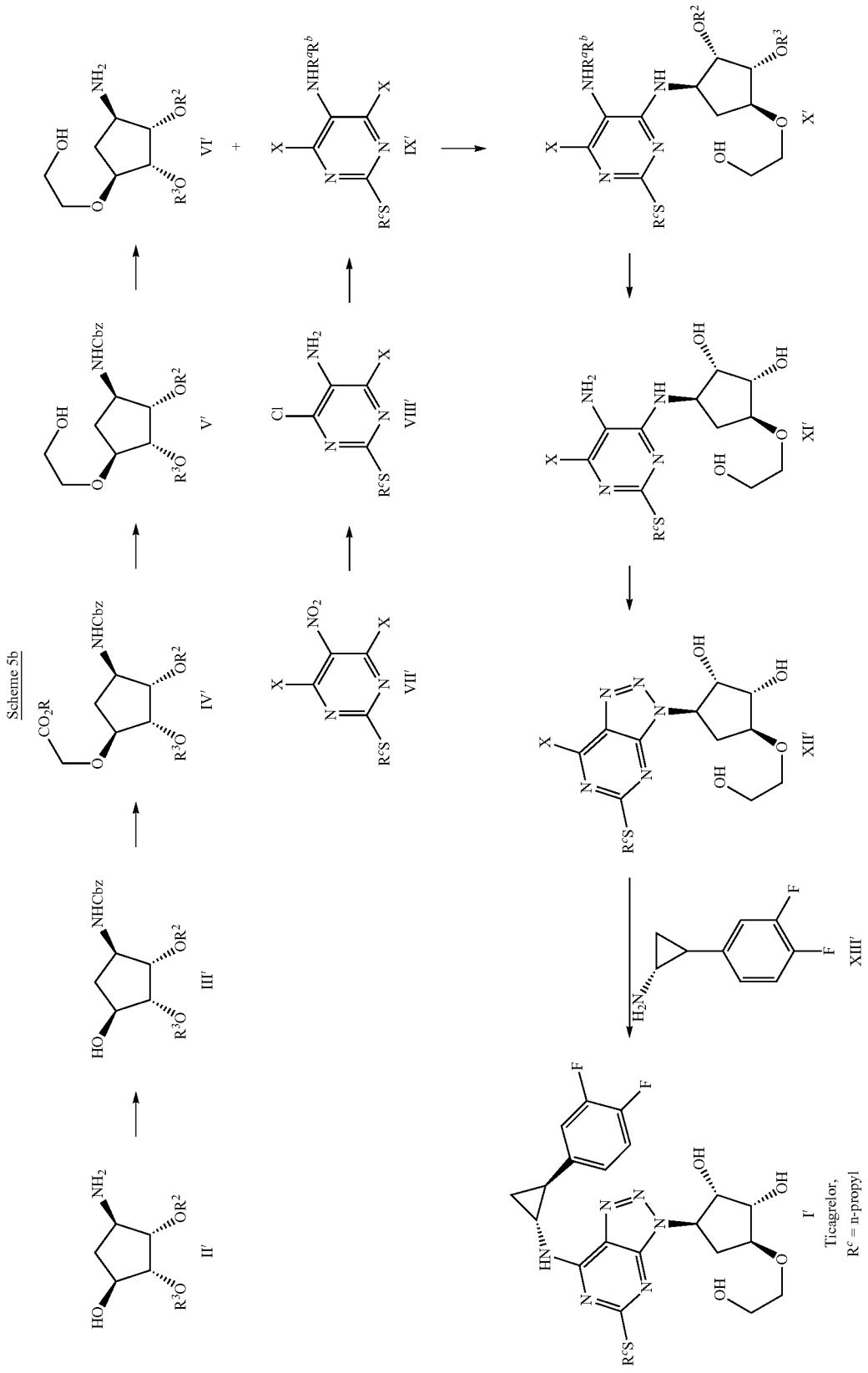

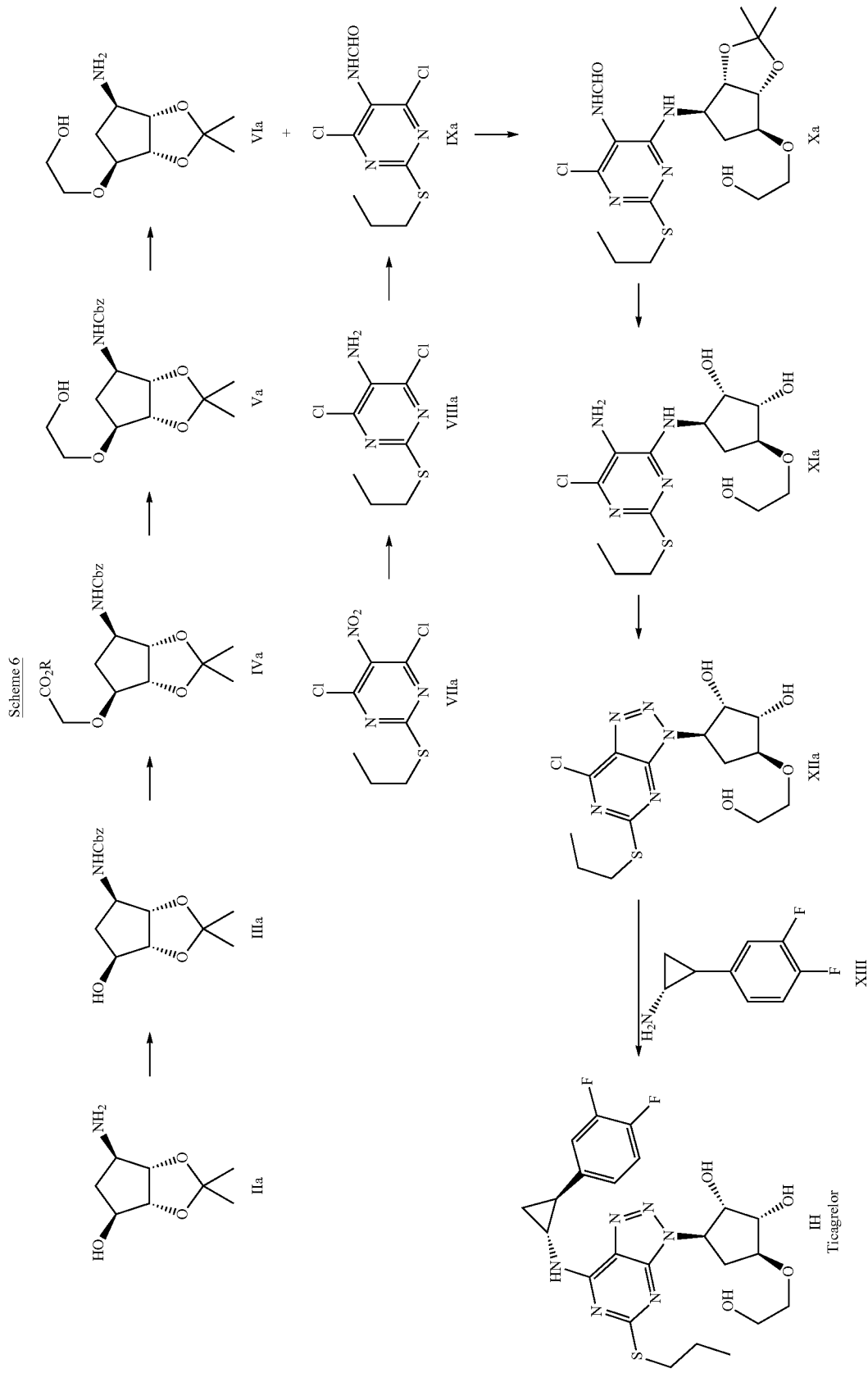

According to certain specific embodiments, Ticagrelor can be obtained by a process as shown in the above Schemes 5A, 5B and 6; wherein $R^1$ is as described above The process shown above provides a high overall yield and high purity for the final product. Most of the synthetic intermediates in the above process, e.g., intermediates III/IIIc, IV/IVa, V/Va, IX/IXa, X/Xa, and XII/XIIa are solid materials that are readily purified on commercially useful scales. One significant advantage of the above process is observed in the coupling of intermediates VI/VIa and IX/IXa to form intermediate X/Xa. In the above process, this step produces no dimer byproduct (resulting from coupling of both aromatic chloro groups). This reaction can be accomplished in as little as 2-3 hrs. In addition, the above process carries out the final coupling with (1R)-2-(3,4-difluorophenyl)cyclopropanamine on the unprotected diol intermediate XII/XIIa. This synthesis step is thus not subject to the significant amounts of isomerization of the cyclopropyl amine optical center that is a known problem associated with some other synthesis routes. Furthermore, this process does not require any column chromatographic purification steps.

The invention provides novel compounds of formula (IX):

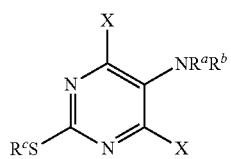

IX wherein, X is a leaving group that can be removed or substituted by conventional methods. According to some embodiments, the leaving group X is selected, for example, from halogens, such as, for example, —Cl, —Br and —I.

$R^a$ is —H and $R^b$ is an amino protecting group. According to some embodiments, the amino protecting group may be selected from, for example, carboaryloxy (benzyloxy), p-alkoxybenzyloxy carbonyl, tert-butyloxycarbonyl, 9-fluorenylmethylcarbonyl, alkanoyl, such as, for example, $C_1$-$C_6$ alkanoyl, benzoyl, a carbamate group, and sulfonamide groups.

According to some embodiments, the amino protecting group is selected from —C(O)O$C_1$-$C_6$alkyl, such as, for example, carboethoxy, carbomethoxy and t-butoxy-carbonyl; optionally substituted —C(O)O$C_6$-$C_{10}$ aryl, such as, for example, benzyloxycarbonyl and p-methoxybenzyloxycarbonyl; optionally substituted —$C_6$-$C_{12}$ aryl($C_1$-$C_3$)alkyl, such as, for example, benzyl, phenethyl, p-methoxybenzyl, 2,3-dimethoxybenzyl, 2,4-dimethoxybenzyl and 9-fluorenylmethyl; optionally substituted —$C_7$-$C_{11}$ arylcarbonyl, such as, for example, benzoyl; —$C_1$-$C_6$ alkanoyl, such as, for example, formyl, acetyl, and propionyl; —$C_1$-$C_6$ alkylsulfonyl, such as, for example, mesyl; optionally substituted phenylsulfonyl, such as, for example, benzenesulfonyl, toluenesulfonyl (tosyl) and 3-nitrobenzenesulfonyl; —Si($C_1$-$C_6$ alkyl)$_3$, such as, for example, tert-butyldimethylsilyl; —$C_1$-$C_6$ alkylcarbamoyl, such as, for example, dimethylcarbamoyl; and optionally substituted —$C_7$-$C_{10}$ arylalkyl carbamoyl, such as, for example, benzyl carbamoyl.

Some examples of suitable amino protecting groups include tosyl, formyl, p-methoxybenzyl, acetyl, 3,4-dimethoxybenzyl, and p-methoxyphenyl.

Other examples include benzyloxycarbonyl, benzyl, 2,4-dimethoxybenzyl, mesyl, tert-butyloxycarbonyl, 9-fluorenylmethyl, carboethoxy, and carbomethoxy.

According to some embodiments: $R^a$ is —H, and $R^b$ is an amino protecting group as defined above. According to some embodiments, $R^a$ is —H, and $R^b$ is —C(O)H, acetyl, propionyl, benzoyl, carbobenzyloxy, carbomethoxy, carboethoxy, or t-Boc.

$R^c$ is a —$C_1$-$C_6$ alkyl group. According to some embodiments $R^c$ is methyl, ethyl, propyl or isopropyl. According to some embodiments $R^c$ is propyl.

In one specific embodiment, the present invention provides the novel compound, N-(4,6-dichloro-2-(propylthio)pyrimidin-5-yl)formamide, having the following structure;

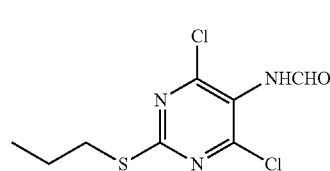

IX-A

The present invention provides novel compounds of formula (X):

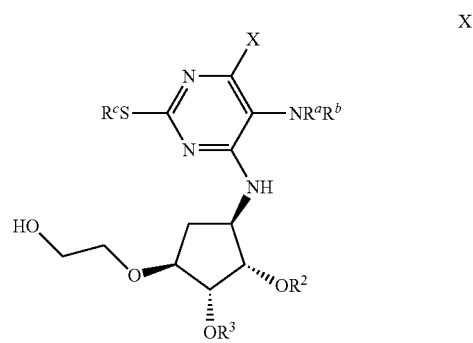

X wherein, $R^a$, $R^b$, $R^c$, X are as defined above.

$R^2$ and $R^3$ have also been defined supra. $R^2$ and $R^3$ can be independently selected from —H, optionally substituted —$C_1$-$C_6$ alkyl, optionally substituted —$C_6$-$C_{18}$ aryl, optionally substituted —$C_6$-$C_{12}$aryl-($C_1$-$C_3$)alkyl, optionally substituted —Si($C_{1-6}$alkyl)$_3$, optionally substituted —C(=O)—$C_{1-6}$alkyl, and optionally substituted —C(=O)—O$C_{1-6}$ alkyl; or $R^2$ and $R^3$ form, together with the oxygen atoms to which they are attached, a heterocyclic ring as shown below:

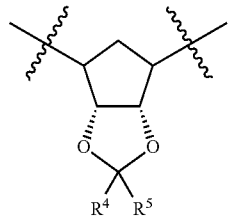

In some embodiments, $R^2$ and $R^3$ together can form an alkylidene group such as a methylidene or isopropylidene group, or an alkoxymethylidene group such as, for example, ethoxymethylidene; each optionally substituted with 1, 2 or 3 substituents independently selected from —$C_1$-$C_8$ alkyl or —$C_6$-$C_8$ aryl.

According to some embodiments, $R^2$ and $R^3$ are independently selected from —H, optionally substituted —Si(C$_{1-6}$ alkyl)$_3$, optionally substituted —C(=O)—C$_{1-6}$alkyl, and optionally substituted —C(=O)—OC$_{1-6}$ alkyl; or $R^2$ and $R^3$ can, together with the oxygen atoms to which they are attached, form a heterocyclic ring as shown below:

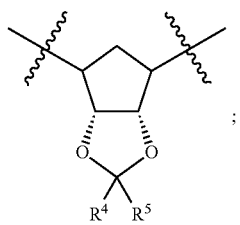

wherein $R^4$ and $R^5$ are independently selected from —H, —C$_{1-6}$ alkyl, and —C$_{6-10}$ aryl; or $R^4$ and $R^5$ together with the carbon atom to which they are attached form a 5 to 6 membered spiro-fused carbocyclic ring, which is optionally substituted by 1, 2 or three substituents independently selected from —C$_1$-C$_6$ alkyl, such as, for example, methyl, ethyl, propyl, isopropyl, butyl, isobutyl, or t-butyl; —C$_6$-C$_{10}$ aryl, such as, for example, phenyl, tolyl or naphthyl and —C$_6$-C$_{10}$ aryl-C$_1$-C$_3$ alkyl, such as, for example, benzyl, 1-phenylethyl, 2-phenylethyl, or α or β naphthylmethyl.

According to some embodiments, $R^1$ is —H, a C$_1$-C$_6$ alkyl group, such as, for example, methyl, ethyl, propyl, isopropyl, butyl, isobutyl, or t-butyl; a —C$_6$-C$_{10}$ aryl group, such as, for example, phenyl, alpha naphthyl or beta naphthyl; or a —C$_6$-C$_{10}$aryl-(C$_1$-C$_2$)alkyl, such as, for example, benzyl, phenylethyl or naphthylmethyl.

According to some embodiments, one or both of $R^2$ and $R^3$ are protecting groups selected from —Si(C$_{1-6}$alkyl)$_3$, —C(=O)—C$_{6-10}$ aryl, —C(=O)—OC$_{1-6}$ alkyl, —C(O)OCH$_2$(C$_6$-C$_{10}$)aryl and substituted —C(O)OCH$_2$(C$_6$-C$_{10}$) aryl. —Si(C$_{1-6}$alkyl)$_3$, such as, for example, trimethylsilyl and tert-butyldimethylsilyl; —C(=O)—C$_{1-6}$alkyl, such as, for example, acetyl and propionyl; —C(=O)—C$_{1-6}$ aryl, such as, for example, benzoyl; —C(=O)—OC$_{1-6}$ alkyl, such as, for example, —C(=O)OCH$_3$, —C(=O)OEt and —C(=O)Ot-Bu; and —C(O)OCH$_2$(C$_6$-C$_{10}$)aryl such as —C(O)O-benzyl.

According to some embodiments, the spiro system can be, for example:

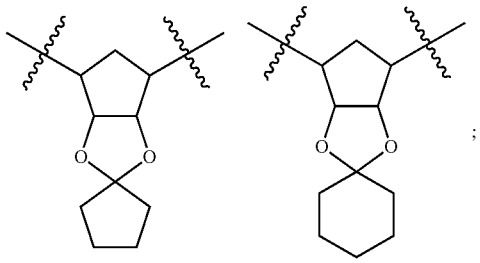

wherein, in the partial structures above, the two oxygen atoms are understood to correspond to the two oxygen atoms to which the $R^2$ and $R^3$ substituents are attached.

In a specific embodiment, the present invention provides a novel compound, N-(4-chloro-6-(((3aS,4R,6S,6aR)-6-(2-hydroxyethoxy)-2,2-dimethyl tetrahydro-3aH-cyclopenta[d][1,3]dioxol-4-yl)amino)-2-(propylthio)pyrimidin-5-yl)formamide, having the following structure:

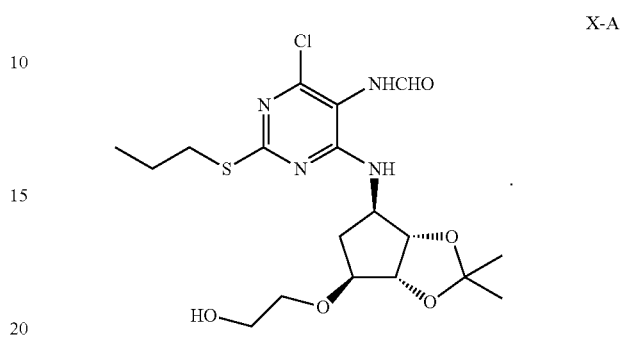

X-A

The present invention provides novel compounds of Formula XI wherein X is as defined above; such as, for example, (1S,2S,3R,5S)-3-((5-amino-6-chloro-2-(propylthio)-pyrimidin-4-yl)amino)-5-(2-hydroxyethoxy)cyclopentane-1,2-diol; as shown below:

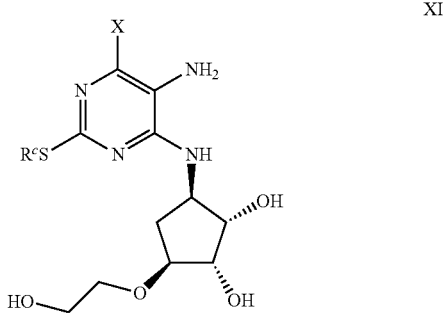

XI

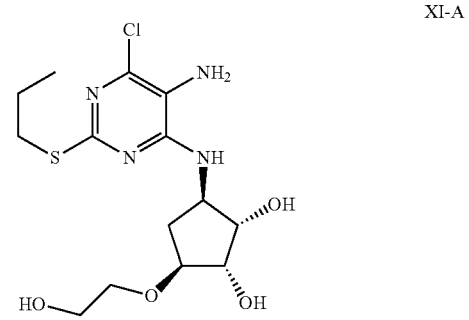

XI-A

In a specific embodiment, the present invention provides a novel compound, (1S,2S,3R,5S)-3-(7-chloro-5-(propylsulfanyl-triazolo) [4,5-d]pyrimidin-3-yl)-5-(2-hydroxyethoxy) cyclopentane-1,2-diol (XII-A) Via (1S,2S,3S,5R)-3-(2-hydroxyethoxy)-5-(5-amino-6-chloro-2-(propylthio) pyrimidin-4-ylamino)cyclopentane-1,2-diol, having the following structure:

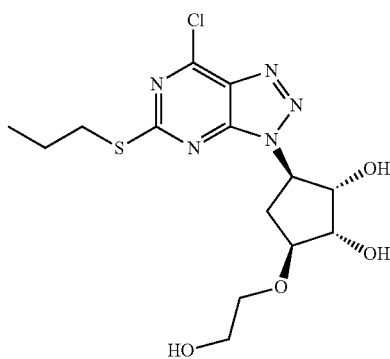

The invention provides a process of preparing process of preparing a compound according to Formula I:

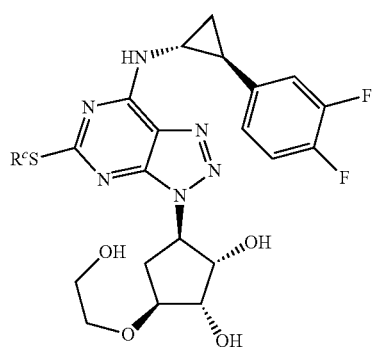

wherein $R^c$ is a —$C_1$-$C_6$ alkyl group, said process comprising coupling a compound according to Formula VI:

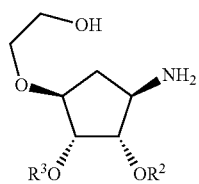

wherein $R^2$ and $R^3$ are defined as provided above; with a compound of Formula IX:

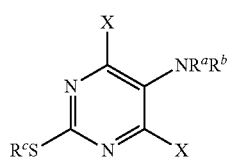

wherein X, $R^a$, $R^b$ and $R^c$ are as defined above; to form a compound of Formula X:

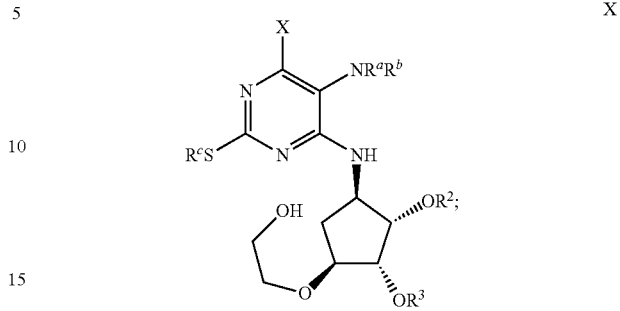

and
converting said compound of Formula X to a compound according to Formula I.

When $R^c$ is n-propyl, the invention thus provides a process of preparing Ticagrelor, said process comprising said process comprising coupling a compound of Formula VI:

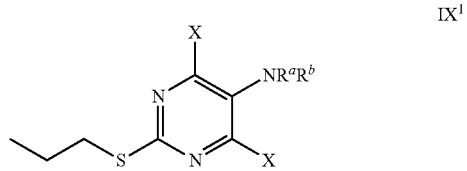

wherein $R^2$ and $R^3$ are defined as provided above; with a compound of Formula $IX^1$:

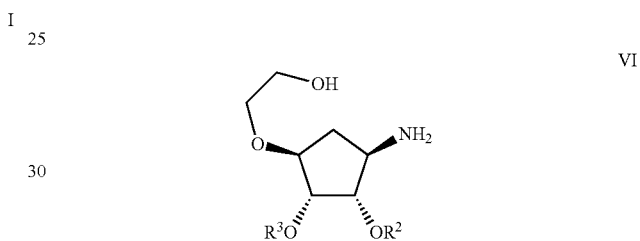

wherein X, $R^a$, and $R^b$ are as defined above; to form a compound according to Formula $X^a$:

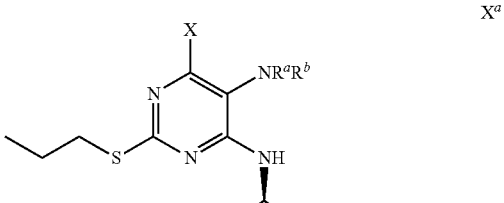

and
converting said compound according to Formula $X^a$ to Ticagrelor.

According to another embodiment, the invention provides a process of preparing Ticagrelor, said process comprising coupling the compound 2-((3aR,4S,6R,6aS)-6-amino-2,2-dimethyltetrahydro-3aH-cyclopenta[d][1,3]dioxol-4-yloxy)ethanol (Formula VI-A):

VIa

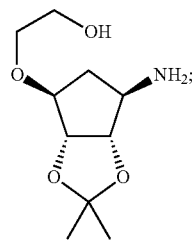

with the compound N-(4,6-dichloro-2-(propylthio)pyrimidin-5-yl)formamide (Formula IX-A):

IX-A

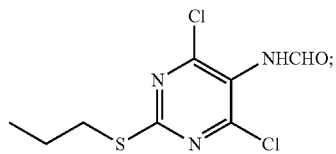

to form the compound N-(4-chloro-6-((3aS,4R,6S,6aR)-6-(2-hydroxyethoxy)-2,2-dimethyltetrahydro-3aH-cyclopenta[d][1,3]dioxol-4-ylamino)-2-(propylthio)pyrimidin-5-yl)formamide (Formula X-A):

X-A

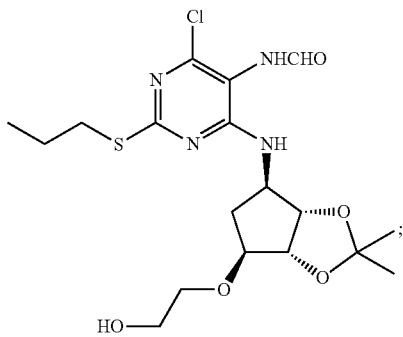

and
converting said compound according to Formula X-A to Ticagrelor.

The step of coupling a Formula VI compound with a Formula IX (or formula IX$^1$) compound (or coupling a formula VI-A compound to a formula IX-A compound) can be carried out, for example, by reacting the compounds, preferably, in the presence of base and in a suitable solvent. Suitable bases include organic bases such as, for example, triethyl amine, and diisopropylethylamine, and also inorganic bases, such as, for example, sodium bicarbonate and potassium bicarbonate. Suitable solvents include any solvent in which the reactants dissolve and are stable. Preferred solvents include polar organic solvents such as $C_1$-$C_6$ alcohols such as methanol, ethanol and propanol, ethers such as t-butylmethyl ether and tetrahydrofuran, glycol solvents such as propylene glycol, polar aprotic solvents such as dimethylformamide and N-methylpyrrolidinone, mixtures of these solvents and mixtures thereof with water. The reaction is preferably carried out at temperatures from about 40° C. up to about the reflux temperature of the reaction mixture; for example from about 40° C. to about 150° C.

The conversion of a compound of Formula X to a compound of Formula I, or of, a compound of Formula X$^a$ or Formula X-A to Ticagrelor, can comprise: removing the N-protecting group represented by R$^a$ and R$^b$, and in some embodiments by only R$^b$; removing the O-protecting groups R$^2$ and R$^3$; diazotizing the intermediate of Formula XI or XIa to produce the intermediate of Formula XII (or XIIa) having the [1,2,3]triazolo[4,5-d]pyrimidine ring system, and coupling the triazolopyrimidine compound of Formula XII (or XIIa) with (1R,2S)-2-(3,4-difluorophenyl)cyclopropanamine (Formula XIII) to produce a Formula I compound, such as, when R$^c$ is n-propyl, Ticagrelor.

The step of removing the N-protecting group can be carried out, for example, by hydrolysis. The hydrolysis reaction may be carried out using a suitable acid reagent and is preferably carried out in a suitable solvent. Suitable acid reagents include, for example mineral acids, such as hydrochloric acid, sulfuric acid and methanesulfonic acid, and organic acids such as trifluoroacetic acid. Suitable solvents include polar solvents, such as, for example $C_1$-$C_6$ alcohols, e.g., methanol, ethanol, propanol and isopropanol, acetonitrile, tetrahydrofuran, dioxane, mixtures of these solvents, and mixtures thereof with water. According to some preferred embodiments, the O-protect groups R$^2$ and R$^3$ may be removed under the same conditions and in the same reaction step as is employed to remove the N-protecting group.

The step of diazotizing the intermediate of Formula XI or XI-A to produce the intermediate of Formula XII (or XIIa) can be carried out, for example, by reacting the Formula XI or XIa compound with a suitable diazotizing agent, preferably, in the presence of a suitable solvent. Suitable diazotizing agents include, for example sodium nitrite and isoamyl nitrite. Suitable solvents for carrying out this reaction include polar organic solvents such as, for example, methanol, ethanol, or acetonitrile, mixtures thereof, and mixtures thereof with water. According to some embodiments, the diazotization reaction can be carried out directly on the hydrolysis reaction mixture used to remove the N-protecting group to prepare the Formula XI (or XIa) compound.

The step of coupling the Formula XII (or XIIa) triazolopyrimidine compound with the compound of Formula XIII ((1R,2S)-2-(3,4-difluorophenyl)cyclopropanamine) can be carried out, for example, by reacting the two compounds in the presence of a suitable base, preferably in the presence of a suitable solvent. Suitable bases include organic bases, such as triethyl amine and diisopropyl ethyl amine and inorganic bases, such as, for example sodium bicarbonate, sodium carbonate, potassium bicarbonate and potassium carbonate. Suitable solvents include solvents that are inert to the reaction conditions and in which the reagents are soluble. The reaction can be carried out in a single phase in solvents including halogenated solvents such as, for example, dichloromethane or dichloroethane, ethers such as t-butylmethyl ether or THF, and other suitably inert organic solvents. The reaction can also be carried out in a two-phase reaction, i.e., with water and a suitable organic solvent such as toluene or THF.

The invention also provides an alternative process for preparation of Ticagrelor according to the two schemes below:

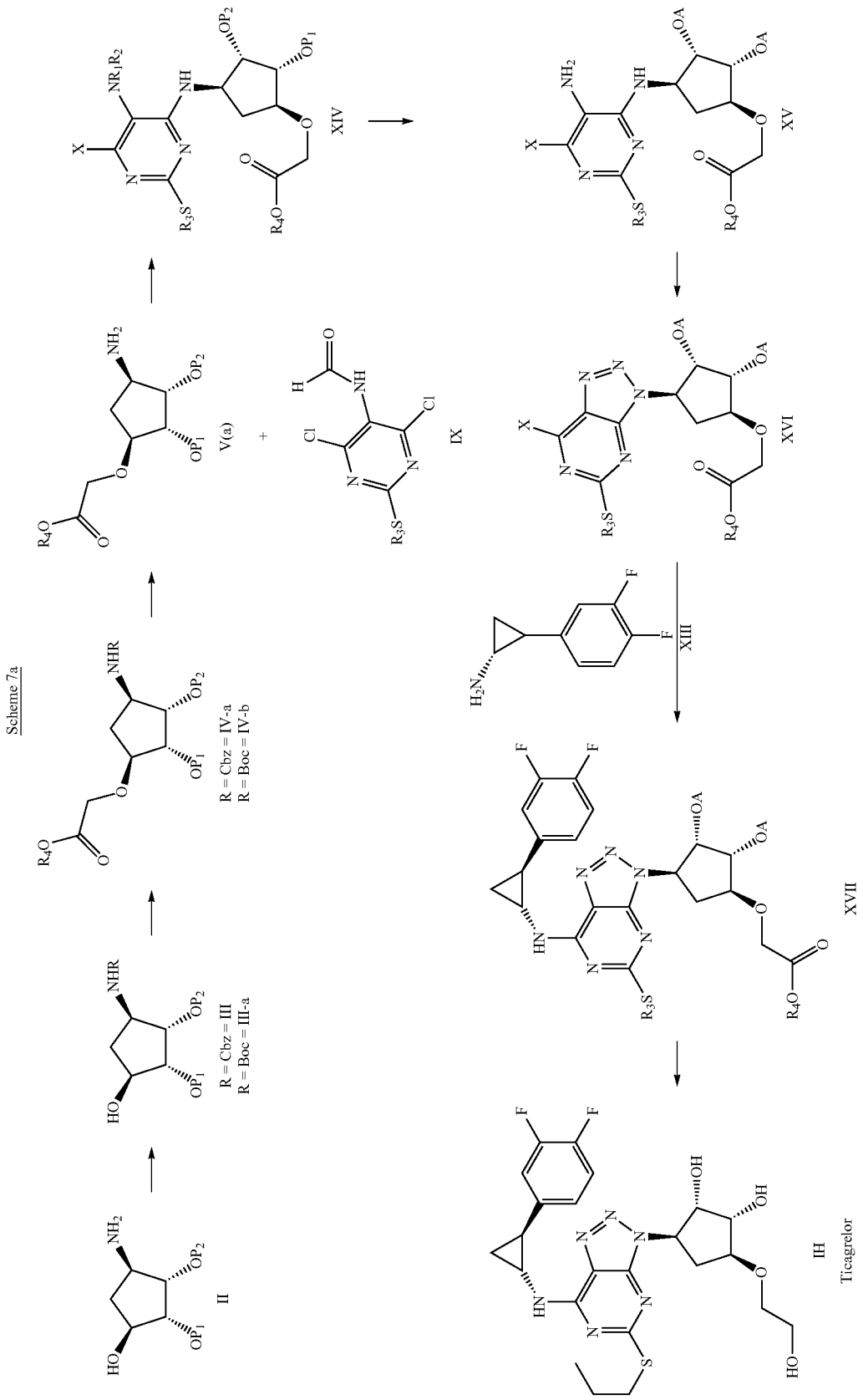

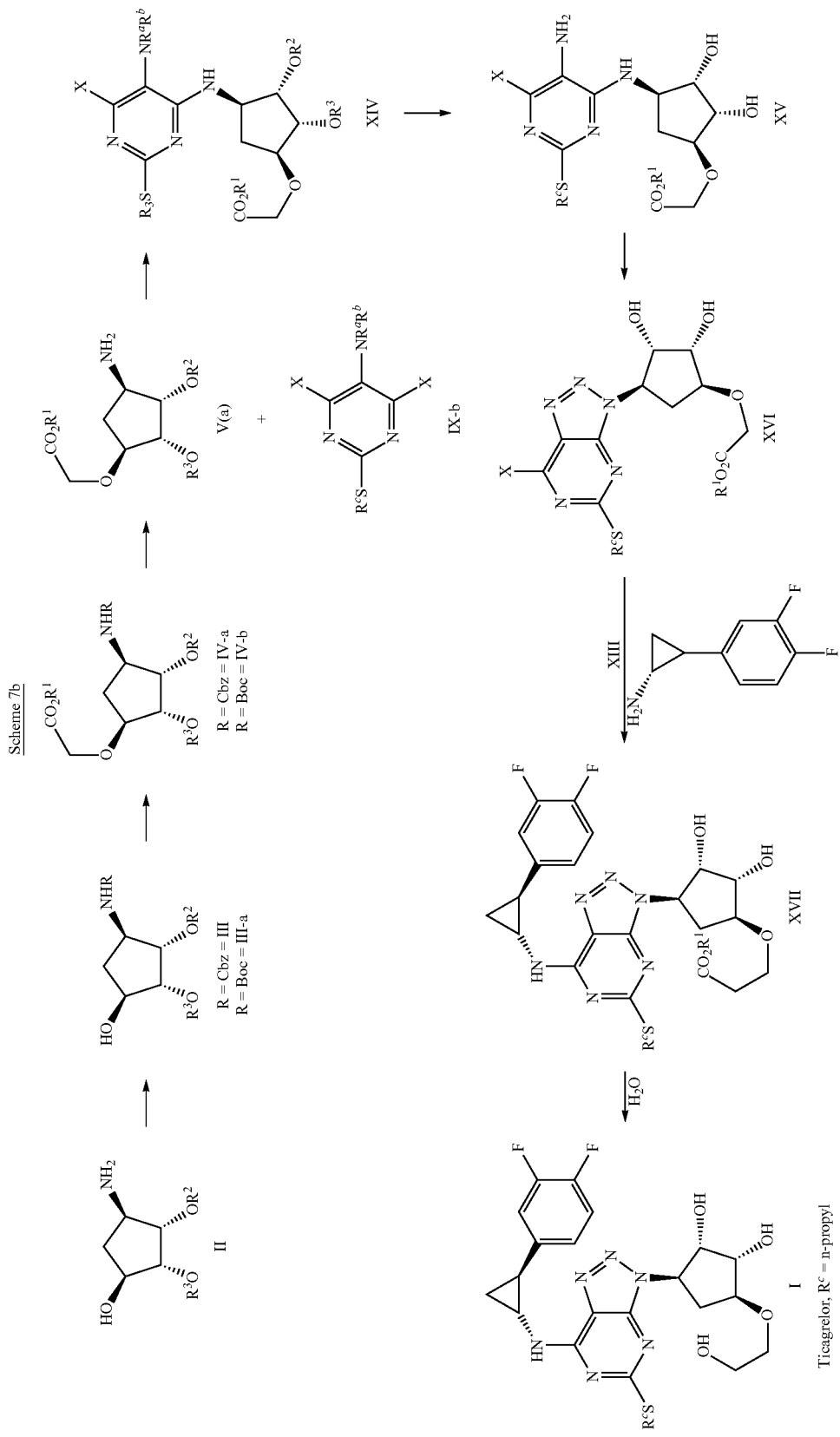

In a specific embodiment, the process for preparation of Ticagrelor is represented by the following systematic reaction scheme:

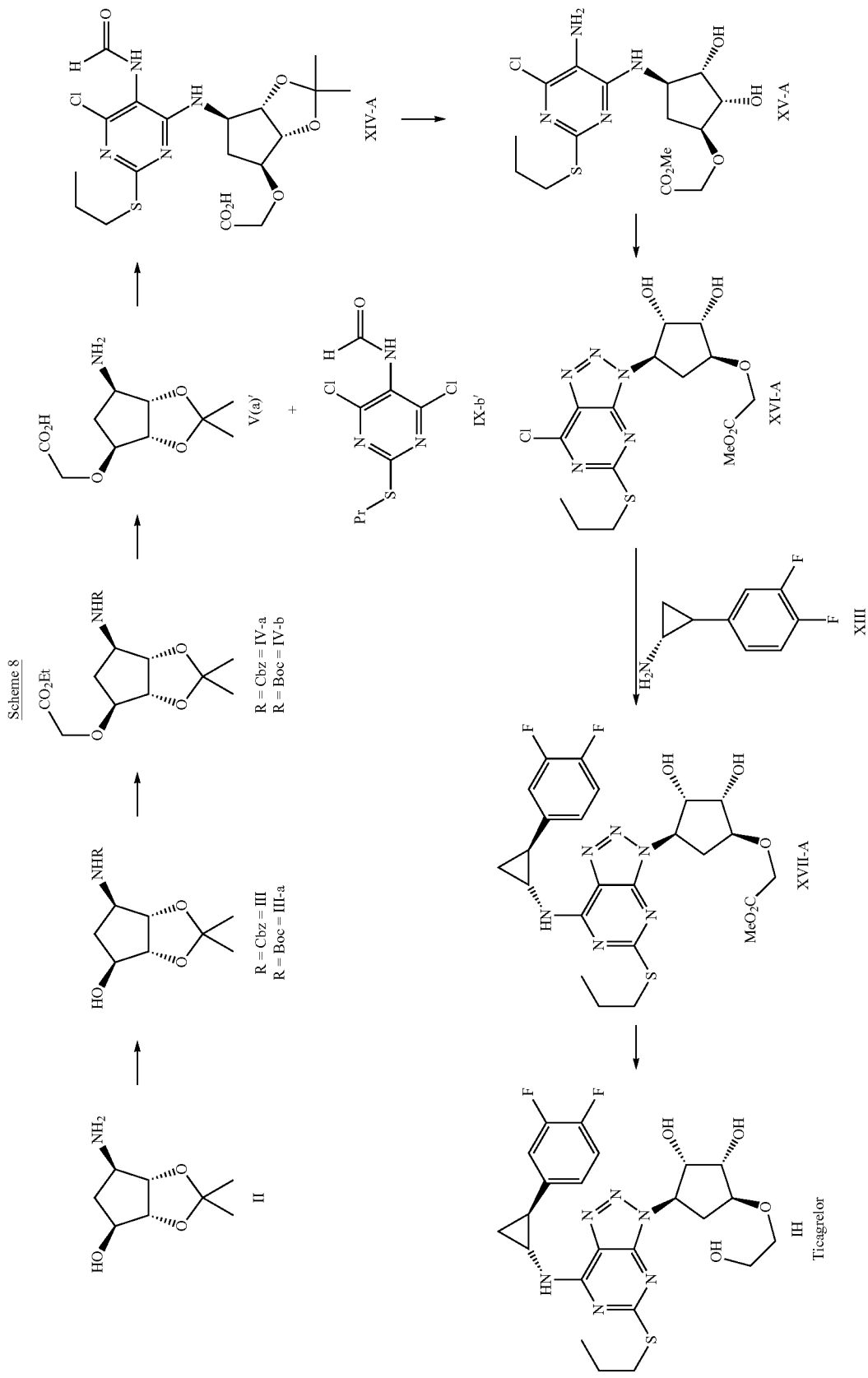
Scheme 8

The present invention provides the novel compound of Formula (XIV):

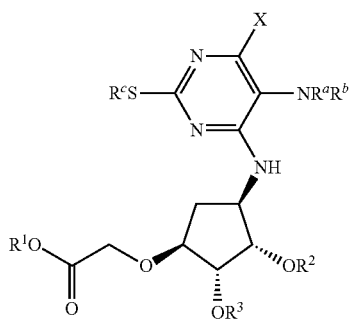

XIV wherein, $R^a$, $R^b$, $R^c$, $R^2$, $R^3$ and X are as defined above; and $R^1$ is selected from —H, $C_1$-$C_6$ straight or branched alkyl, $C_6$-$C_{10}$ aryl, and $C_7$-$C_{12}$ arylalkyl. According to some embodiments of the Formula XIV compound, $R^c$ is n-propyl. In a specific embodiment, the invention provides a novel compound, 2-(((3aR,4S,6R,6aS)-6-((6-chloro-5-formamido-2-(propylthio)pyrimidin-4-yl)amino)-2,2-dimethyltetrahydro-3aH-cyclopenta-[d][1,3]dioxol-4-yl)oxy)acetic acid (Compound (XIV-A):

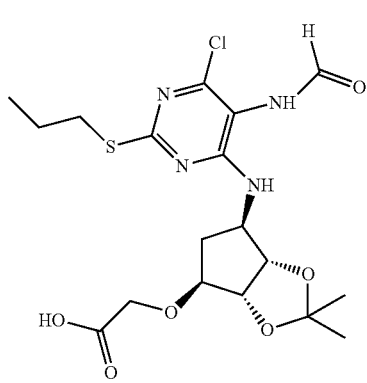

XIV-A

The invention provides a process of preparing process of preparing a compound according to Formula I:

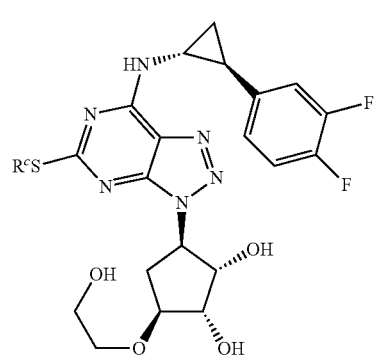

I wherein $R^c$ is a —$C_1$-$C_6$ alkyl group; said process comprising coupling a compound of Formula V(a):

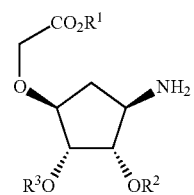

V(a)

wherein $R^1$, $R^2$ and $R^3$ are defined as provided above; with a compound of Formula IX-b:

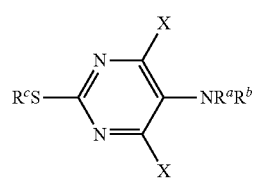

IX-b wherein $R^a$, $R^b$, $R^c$ and X are as defined above; to form a compound of Formula XV:

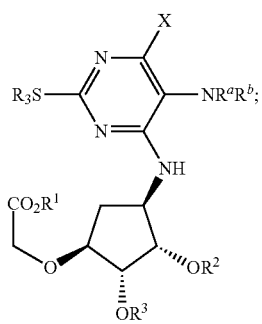

XIV and converting said compound according to Formula XV to a compound of Formula I.

The invention thus provides a process of preparing Ticagrelor when $R^c$ is n-propyl, said process comprising coupling a compound according to Formula V(a):

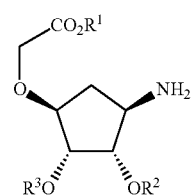

V(a)

wherein $R^1$, $R^2$ and $R^3$ are defined as provided above; with a compound of Formula IX-b':

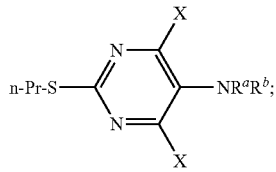

to form a compound according to Formula XIV':

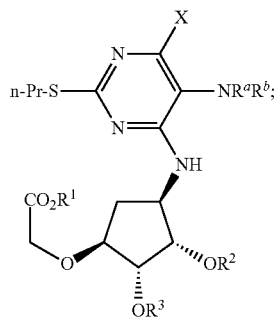

and
converting the Formula XIV' compound (Formula XIV; $R^c$ is n-propyl) to Ticagrelor.

According to another embodiment, the invention provides a process of preparing Ticagrelor, the process comprising coupling the compound, 2-((3aR,4S,6R,6aS)-6-amino-2,2-dimethyltetrahydro-3aH-cyclopenta[d][1,3]dioxol-4-yloxy) acetic acid:

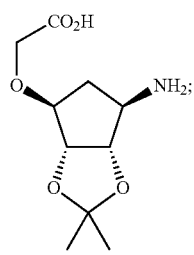

with N-(4,6-dichloro-2-(propylthio)pyrimidin-5-yl)formamide (Formula IX-b'):

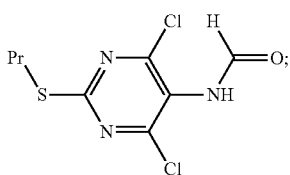

to form the compound 2-((3aR,4S,6R,6aS)-6-(6-chloro-5-formamido-2-(propylthio)-pyrimidin-4-ylamino)-2,2-dimethyltetrahydro-3aH-cyclopenta[d][1,3]dioxol-4-yloxy)-acetic acid (Formula XV-A):

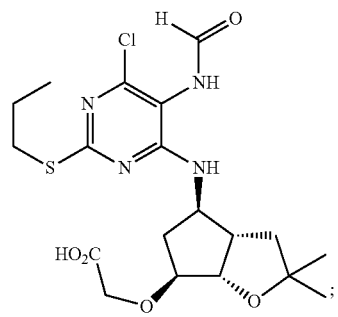

and converting said compound to Ticagrelor.

The step of coupling a Formula V(a) compound with a Formula IX (or formula IX-b) compound (or coupling a formula V(a)' compound to a formula IX-b' compound) can be carried out, for example, by reacting the compounds, preferably, in the presence of base and in a suitable solvent. Suitable bases include organic bases such as, for example, triethyl amine, and diisopropylethylamine, and also inorganic bases, such as, for example, sodium bicarbonate and potassium bicarbonate. Suitable solvents include any solvent in which the reactants dissolve and are stable. Preferred solvents include polar organic solvents such as $C_1$-$C_6$ alcohols such as methanol, ethanol and propanol, ethers such as t-butylmethyl ether and tetrahydrofuran, glycol solvents such as propylene glycol, polar aprotic solvents such as dimethylformamide and N-methylpyrrolidinone, mixtures of these solvents and mixtures thereof with water. The reaction is preferably carried out at temperatures from about 40° C. up to about the reflux temperature of the reaction mixture; for example from about 40° C. to about 150° C.

The conversion of a compound of Formula XIV to a compound of Formula I, or of, a compound of XIV-A to Ticagrelor, can comprise: removing the N-protecting group represented by $R^a$ and $R^b$, and in some embodiments by only $R^b$; removing the O-protecting groups $R^2$ and $R^3$; diazotizing the intermediate of Formula XV or XVa to produce the intermediate of Formula XVI (or XVI-A) having the [1,2,3]triazolo[4,5-d]pyrimidine ring system; coupling the triazolopyrimidine compound of Formula XVI (or XVI-A) with (1R)-2-(3,4-difluorophenyl)cyclopropanamine (Formula XIII): to produce an ester compound of Formula XVII (or XVII-A), and converting the Formula XVII (or XVII-A) ester compound to a compound of Formula I, which, when $R^c$ is n-propyl, is the compound, Ticagrelor.

The step of removing the N-protecting group can be carried out, for example, by hydrolysis. The hydrolysis reaction may be carried out using a suitable acid reagent and is preferably carried out in a suitable solvent. Suitable acid reagents include, for example mineral acids, such as hydrochloric acid, sulfuric acid and organic acids such as methanesulfonic acid, and trifluoroacetic acid. Suitable solvents include polar solvents, such as, for example $C_1$-$C_6$ alcohols, e.g., methanol, ethanol, propanol and isopropanol and other organic solvents such as acetonitrile, tetrahydrofuran, mixtures of these solvents, and mixtures thereof with water. According to some preferred embodiments, the O-protect groups $R^2$ and $R^3$ may be removed under the same conditions and in the same reaction step as is employed to remove the N-protecting group.

The step of diazotizing the intermediate of Formula XV or XV-A to produce the intermediate of Formula XVI (or XVI-A) can be carried out, for example, by reacting the Formula XV or XV-A compound with a suitable diazotizing agent, preferably, in the presence of a suitable solvent. Suitable diazotizing agents include, for example sodium nitrite and isoamyl nitrite. Suitable solvents for carrying out this reaction include polar organic solvents such as, for example, methanol, ethanol, or acetonitrile, mixtures thereof, and mixtures thereof with water. According to some embodiments, the diazotization reaction can be carried out directly on the hydrolysis reaction mixture that was used to remove the N-protecting group to prepare the Formula XV (or XV-A) compound.

The step of coupling the Formula XVI (or XVI-A) triazolopyrimidine compound with the compound of Formula XIII ((1R)-2-(3,4-difluorophenyl)cyclopropanamine) can be carried out, for example, by reacting the two compounds in the presence of a suitable base, preferably in the presence of a suitable solvent. Suitable bases include organic bases, such as triethyl amine and diisopropyl ethyl amine and inorganic bases, such as, for example sodium bicarbonate, sodium carbonate, potassium bicarbonate and potassium carbonate. Suitable solvents include solvents that are inert to the reaction conditions and in which the reagents are soluble. The reaction can be carried out in a single phase in solvents including halogenated solvents such as, for example, dichloromethane or dichloroethane, ethers such as t-butylmethyl ether or THF, and other suitably inert organic solvents. The reaction can also be carried out in a two-phase reaction, i.e., with water and a suitable organic solvent such as toluene or THF.

The conversion of a compound of Formula XVII, or Formula XVII-A to Ticagrelor, requires a functional group transformation of the carboxylic ester to a primary alcohol. This transformation can be accomplished, for example by reduction of the ester using a suitable reducing agent. Suitable reducing agents are those that can selectively reduce the ester moiety, for example hydride reagents, such as sodium borohydride-BF$_3$.OEt$_2$, lithium borohydride, lithium triethylborohydride, LAH, L-selctride and diborane and its complexes The reaction is preferably done in the presence of a suitable solvent, for example, THF or dioxane.

Having described the invention with reference to particular preferred embodiments and illustrative examples, those in the art can appreciate modifications to the invention as described and illustrated that do not depart from the spirit and scope of the invention as disclosed in the specification. The examples are set forth to aid in understanding the invention but are not intended to, and should not be construed to, limit its scope in any way. It will be apparent to those skilled in the art that many modifications, both to materials and methods, may be practiced without departing from the scope of the invention.

EXAMPLES

Example 1

Preparation of tert-butyl (3aS,4R,6S,6aR)-6-hydroxy-2,2-dimethyltetrahydro-3aH-cyclopenta[d][1,3]dioxol-4-ylcarbamate (compound 3)

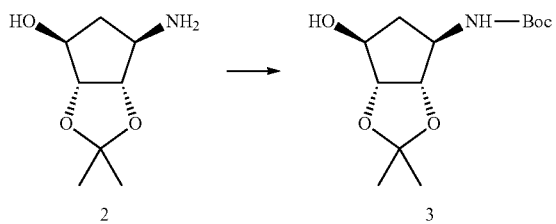 [SMILES: CC1(C)O[C@@H]2[C@H](O1)[C@@H](O)C[C@H]2N ; CC(C)(C)OC(=O)N[C@@H]1C[C@H](O)[C@H]2OC(C)(C)O[C@H]21]

Compound 2 (100 g,) was dissolved in THF (2-15V). A solution of water (2-15V) and sodium carbonate (67.4 g) was added to the solution. The resulting mixture was stirred at room temperature, followed by dropwise addition of Boc-anhydride (138.77 g) The reaction mixture was agitated for 1-3 hrs. Then the aqueous and organic layers were separated. The organic layer was concentrated to produce a residue, which was crystallized to produce compound 3 (149.1 g).

$^1$H NMR (400 MHz, CDCl$_3$): δ 5.44 (d, J=8 Hz, 1H), 4.57-4.49 (m, 2H), 4.27 (t, J=4 Hz, 1H), 4.09 (brs, 1H), 2.55 (brs, 1H), 2.22 (brs, 1H), 1.68 (d, J=16 Hz, 1H), 1.45 (s, 9H), 1.41 (s, 3H), 1.26 (s, 3H). $^{13}$C NMR (100 MHz, CDCl$_3$) δ 155.20, 110.17, 86.23, 35.47, 28.44, 26.23, 23.85.

Example 1a

Preparation of tert-butyl (3aS,4R,6S,6aR)-6-hydroxy-2,2-dimethyltetrahydro-3aH-cyclopenta[d][1,3]dioxol-4-ylcarbamate Compound 2 (100 g,) was dissolved in THF (15V). A solution of water (15V) and sodium carbonate (67.4 g) was added to the solution. The resulting mixture was stirred at room temperature, followed by dropwise addition of Boc-anhydride (138.77 g). The reaction mixture was agitated for 1 hr. Then the aqueous and organic layers were separated. The organic layer was concentrated to produce a residue, which was crystallized to produce compound 3 (149.1 g).

$^1$H NMR (400 MHz, CDCl$_3$): δ 5.44 (d, J=8 Hz, 1H), 4.57-4.49 (m, 2H), 4.27 (t, J=4 Hz, 1H), 4.09 (brs, 1H), 2.55 (brs, 1H), 2.22 (brs, 1H), 1.68 (d, J=16 Hz, 1H), 1.45 (s, 9H), 1.41 (s, 3H), 1.26 (s, 3H). $^{13}$C NMR (100 MHz, CDCl$_3$) δ 155.20, 110.17, 86.23, 35.47, 28.44, 26.23, 23.85.

Example 2

Preparation of benzyl (3aS,4R,6S,6aR)-6-hydroxy-2,2-dimethyltetrahydro-3aH-cyclopenta[d][1,3]dioxol-4-ylcarbamate

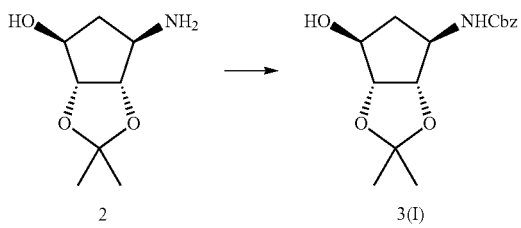 [SMILES: CC1(C)O[C@@H]2[C@H](O1)[C@@H](O)C[C@H]2N ; CC1(C)O[C@@H]2[C@H](O1)[C@@H](O)C[C@H]2NC(=O)OCc1ccccc1]

Compound 2 (50 g) was dissolved in methylisobutylketone (MIBK) (900 mL). Water (1-5V mL) and potassium carbonate (47.80 g) were added, followed by dropwise addition of benzyl chloroformate (54.16 g). The reaction mixture was stirred at room temperature for 4-6 hours. The aqueous and organic layers were separated and the aqueous layer was extracted with MIBK. The combined organic layers were concentrated and the resulting residue was purified by crystallization in n-hexane give compound 2 (83.36 g).

$^1$H NMR (400 MHz, CDCl$_3$): δ 7.37-7.30 (m, 5H), 5.68 (brs, 1H), 5.11 (s, 2H), 4.60 (d, J=4 Hz, 1H), 4.49 (dd, J=8 Hz, J=4 Hz, 1H), 4.28 (brs, 1H), 4.20 (t, J=8 Hz, 1H), 2.28-2.06 (m, 2H), 1.73-1.69 (m, 2H), 1.42 (s, 3H), 1.29 (s, 3H). $^{13}$C NMR (100 MHz, CDCl$_3$) δ 155.58, 136.51, 128.53, 128.15, 110.30, 86.16, 86.05, 77.59, 66.74, 57.03, 35.33, 26.18, 23.80.

Example 2a

Preparation of benzyl (3aS,4R,6S,6aR)-6-hydroxy-2,2-dimethyltetrahydro-3aH-cyclopenta[d][1,3]dioxol-4-ylcarbamate (Compound 3(l))

Compound 2 (50 g) was dissolved in MIBK (900 mL). Water (5V mL) and potassium carbonate (47.80 g) were added, followed by dropwise addition of benzyl chloroformate (54.16 g). The reaction mixture was stirred at room temperature for 4-6 hours. The aqueous and organic layers were then separated. The aqueous layer was extracted with MIBK. The combined organic layers were concentrated and the resulting residue was purified by crystallization in n-hexane give the compound 3(l) (83.36 g).

$^1$H NMR (400 MHz, CDCl$_3$): δ 7.37-7.30 (m, 5H), 5.68 (brs, 1H), 5.11 (s, 2H), 4.60 (d, J=4 Hz, 1H), 4.49 (dd, J=8 Hz, J=4 Hz, 1H), 4.28 (brs, 1H), 4.20 (t, J=8 Hz, 1H), 2.28-2.06 (m, 2H), 1.73-1.69 (m, 2H), 1.42 (s, 3H), 1.29 (s, 3H). $^{13}$C NMR (100 MHz, CDCl$_3$) δ 155.58, 136.51, 128.53, 128.15, 110.30, 86.16, 86.05, 77.59, 66.74, 57.03, 35.33, 26.18, 23.80.

Example 3

Preparation of ethyl 243aR,4S,6R,6aS)-6-(benzyloxycarbonylamino)-2,2-dimethyltetrahydro-3aH-cyclopenta[d][1,3]dioxol-4-yloxy)acetate (compound 4(I)

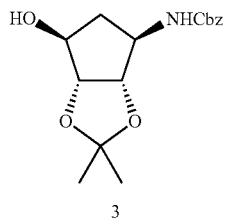

3

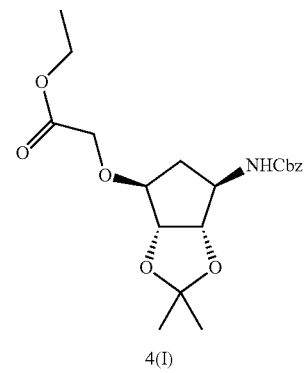

4(I)

Compound 3 (70 g,) was dissolved in THF (10-20V) and potassium-tert-butoxide (30.66 g) was added. Then, ethylbromoacetate (45.64 g) in THF (170 mL) was added dropwise. The reaction mixture was stirred 0° C. for 8-10 hrs. The reaction progress was monitored by TLC. The reaction was then quenched by addition of water (210 mL), and the THF phase was separated and concentrated. The thus obtained residue was taken up in water (150 mL), and this aqueous mixture was extracted with ethyl acetate. The ethyl acetate extract was concentrated to produce compound 4(I) (105 g), which was used for the next step without further purification.

$^1$H NMR (400 MHz, CDCl$_3$): δ 7.37-7.28 (m, 5H), 5.96 (d, J=8 Hz, 1H), 5.10 (s, 2H), 4.57 (s, 2H), 4.22-3.90 (m, 6H), 3.91 (d, J=4 Hz, 1H), 2.24-2.18 (m, 1H), 1.82 (d, J=12 Hz, 1H), 1.40 (s, 3H), 1.26 (s, 3H), 1.23 (t, J=8 Hz, 3H).). $^{13}$C NMR (100 MHz, CDCl$_3$) δ 170.27, 155.68, 136.71, 128.45, 128.16, 128.00, 110.42, 86.28, 86.07, 85.69, 83.03, 66.95, 66.54, 61.31, 57.37, 56.67, 33.22, 31.94, 29.71, 26.16, 23.79, 14.12.

Example 3a

Preparation of ethyl 243aR,4S,6R,6aS)-6-(benzyloxycarbonylamino)-2,2-dimethyltetrahydro-3aH-cyclopenta[d][1,3]dioxol-4-yloxy)acetate (compound 4(l)

Compound 3 (70 g,) was dissolved in THF (20V). Potassium-tert-butoxide (30.66 g) was added. Then, ethylbromoacetate (45.64 g) in THF (170 mL) was added dropwise. The reaction mixture was stirred 0° C. for 8-10 hrs. The reaction progress was monitored by TLC. The reaction was then quenched by addition of water (210 mL), and the THF phase was separated and concentrated. The thus obtained residue was taken up in water (150 mL), and this aqueous mixture was extracted with ethyl acetate. The ethyl acetate extract was concentrated to produce compound 4(I) (105 g), which was used for the next step without further purification.

$^1$H NMR (400 MHz, CDCl$_3$): δ 7.37-7.28 (m, 5H), 5.96 (d, J=8 Hz, 1H), 5.10 (s, 2H), 4.57 (s, 2H), 4.22-3.90 (m, 6H), 3.91 (d, J=4 Hz, 1H), 2.24-2.18 (m, 1H), 1.82 (d, J=12 Hz, 1H), 1.40 (s, 3H), 1.26 (s, 3H), 1.23 (t, J=8 Hz, 3H).). $^{13}$C NMR (100 MHz, CDCl$_3$) δ 170.27, 155.68, 136.71, 128.45, 128.16, 128.00, 110.42, 86.28, 86.07, 85.69, 83.03, 66.95, 66.54, 61.31, 57.37, 56.67, 33.22, 31.94, 29.71, 26.16, 23.79, 14.12.

Example 4

Preparation of ethyl 2-((3aR,4S,6R,6aS)-6-(tert-butoxycarbonylamino)-2,2-dimethyltetrahydro-3aH-cyclopenta[d][1,3]dioxol-4-yloxy)acetate (compound 4)

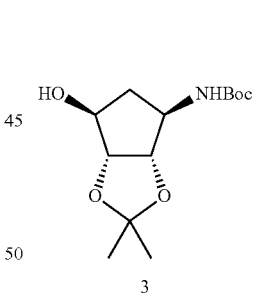

3

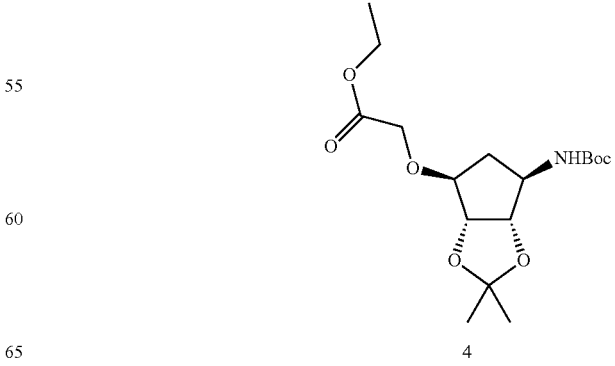

4

Compound 3 (50 g) was dissolved in THF (5-20V). Potassium-tert-butoxide (30.80 g) was added, followed by a pre-prepared solution of ethylbromoacetate (45.88 g) in THF (200 mT), which was added dropwise. The resulting mixture was stirred at 0° C. for 8-10 hours. The reaction was then quenched by addition of water (20 mL). The organic layer was concentrated and the resulting residue was purified by crystallization in n-hexane to give compound 4 (40 g).

$^1$H NMR (400 MHz, CDCl$_3$): δ 5.56 (d, J=8 Hz, 1H), 4.59-4.57 (m, 2H), 4.25 (q, J=8 Hz, 2H), 4.18-4.08 (m, 2H), 3.91 (d, J=4 Hz, 1H), 2.25-2.18 (m, 1H), 1.80 (d, J=16 Hz, 1H), 1.74 (brs, 1H), 1.45 (s, 9H), 1.40 (s, 3H), 1.32 (t, J=8 Hz, 3H), 1.22 (s, 3H). $^{13}$C NMR (100 MHz, CDCl$_3$) δ 1.70.19, 155.16, 110.38, 86.34, 85.89, 83.10, 79.20, 66.98, 61.24, 56.23, 33.34, 31.94, 29.71, 29.38, 28.44, 26.20, 23.84, 22.71, 14.21, 14.14.

Example 4a

Preparation of ethyl 2-((3aR,4S,6R,6aS)-6-(tert-butoxycarbonylamino)-2,2-dimethyltetrahydro-3aH-cyclopenta[d][1,3]dioxol-4-yloxy)acetate (compound 4)

Compound 3 (50 g) was dissolved in THF (20V). Potassium-tert-butoxide (30.80 g) was added, followed by a pre-prepared solution of ethylbromoacetate (45.88 g) in THF (200 mL), which was added drop wise. The resulting mixture was stirred at 0° C. for 8-10 hours. The reaction was then quenched by addition of water (20 mL). The organic layer was concentrated and the resulting residue was purified by crystallization in n-hexane to give compound 4 (40 g).

$^1$H NMR (400 MHz, CDCl$_3$): δ 5.56 (d, J=8 Hz, 1H), 4.59-4.57 (m, 2H), 4.25 (q, J=8 Hz, 2H), 4.18-4.08 (m, 2H), 3.91 (d, J=4 Hz, 1H), 2.25-2.18 (m, 1H), 1.80 (d, J=16 Hz, 1H), 1.74 (brs, 1H), 1.45 (s, 9H), 1.40 (s, 3H), 1.32 (t, J=8 Hz, 3H), 1.22 (s, 3H). $^{13}$C NMR (100 MHz, CDCl$_3$) δ 1.70.19, 155.16, 110.38, 86.34, 85.89, 83.10, 79.20, 66.98, 61.24, 56.23, 33.34, 31.94, 29.71, 29.38, 28.44, 26.20, 23.84, 22.71, 14.21, 14.14.

Example 5

Preparation of ethyl 2-((3aR,4S,6R,6aS)-6-amino-2,2-dimethyltetrahydro-3aH-cyclopenta[d][1,3]dioxol-4-yloxy)acetate

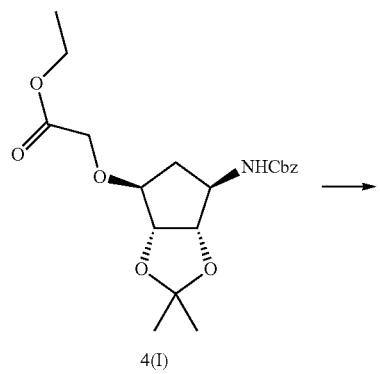

4(I)

-continued

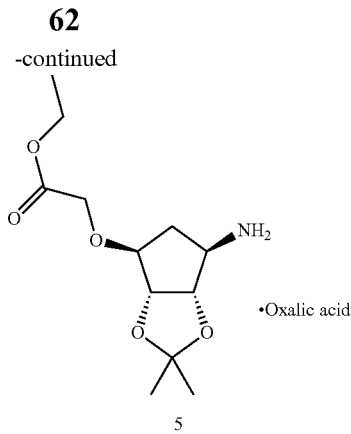

5

Compound 4 (85 g) was dissolved in ethanol (5-10V). Ammonium formate (13.6 g) and 10% Pd/C were added. The reaction mixture was heated to 50-60° C. for 1-3 hours. The reaction mixture was then filtered. The ethanol was distilled off leaving a residue. The residue was again dissolved in ethanol and oxalic acid (27.23 g) was added. The resulting reaction mixture was heated to 50-60° C. for 1-4 hours. The reaction mixture was then cooled to RT and stirred for 8-10 hrs. The ethanol was then distilled off and residue was suspended in diisopropylether. Compound 5 (66 g) was isolated by filtration and drying.

$^1$H NMR (400 MHz, D$_2$O): δ 4.24 (d, J=8 Hz, 2H), 4.21 (q, J=8 Hz, 2H), 4.14 (d, J=4 Hz, 1H), 3.75-3.72 (m, 1H), 2.44-2.37 (m, 1H), 2.12 (dd, J=12 Hz, J=4 Hz, 1H), 1.45 (s, 3H), 1.33 (s, 3H), 1.25 (t, J=4 Hz, 3H). $^{13}$C NMR (100 MHz, D$_2$O) δ 172.64, 165.71, 112.31, 83.97, 83.89, 82.27, 82.15, 67.06, 66.47, 62.41, 55.84, 32.26, 24.83, 22.86, 13.17.

Example 5a

Preparation of ethyl 2-((3aR,4S,6R,6aS)-6-amino-2,2-dimethyltetrahydro-3aH-cyclopenta[d][1,3]dioxol-4-yloxy)acetate Compound 4 (85 g) was dissolved in ethanol (5V). Ammonium formate (13.6 g) and 10% Pd/C (8.5 g) were added. The reaction mixture was heated to 50-60° C. for 1-3 hours. The reaction mixture was then filtered. The ethanol was distilled off leaving a residue. The residue was again dissolved in ethanol and oxalic acid (27.23 g) was added. The resulting reaction mixture was heated to 50-60° C. for 1-4 hours. The reaction mixture was then cooled to RT and stirred for 8-10 hrs. The ethanol was then distilled off and residue was suspended in diisopropylether. Compound 5 (66 g) was isolated by filtration and drying.

$^1$H NMR (400 MHz, D$_2$O): δ 4.24 (d, J=8 Hz, 2H), 4.21 (q, J=8 Hz, 2H), 4.14 (d, J=4 Hz, 1H), 3.75-3.72 (m, 1H), 2.44-2.37 (m, 1H), 2.12 (dd, J=12 Hz, J=4 Hz, 1H), 1.45 (s, 3H), 1.33 (s, 3H), 1.25 (t, J=4 Hz, 3H). $^{13}$C NMR (100 MHz, D$_2$O)

δ 172.64, 165.71, 112.31, 83.97, 83.89, 82.27, 82.15, 67.06, 66.47, 62.41, 55.84, 32.26, 24.83, 22.86, 13.17.

Example 6

Preparation of ethyl 2-((3aR,4S,6R,6aS)-6-amino-2,2-dimethyltetrahydro-3aH-cyclopenta[d][1,3]dioxol-4-yloxy)acetate

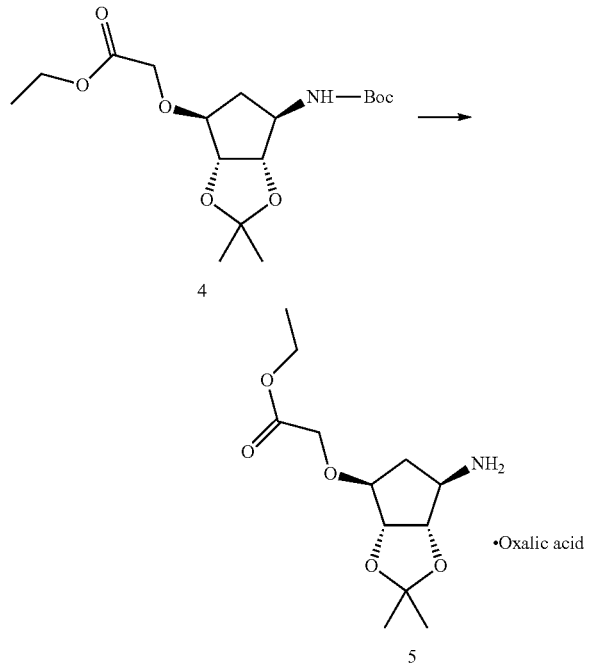

Compound 4 (39 g) was dissolved in ethanol (10-20V). Ceric ammonium nitrate (59.49 g) was added. The resulting reaction mixture was heated to 50-70° C. for 10-12 hrs. The reaction mixture was then quenched and extracted with dichloromethane (DCM). The DCM layer was distilled off. The resulting residue was suspended in ethanol (2-10V) and oxalic acid (13.68 g) was added. This reaction mixture was heated to 30-70° C. for 1-4 hours and then cooled to room temperature and stirred for 8-10 hours. The ethanol layer was distilled off and the resulting residue was purified and filtered to give compound 5 (25.2 g).

Example 6a

Preparation of ethyl 2-((3aR,4S,6R,6aS)-6-amino-2,2-dimethyltetrahydro-3aH-cyclopenta[d][1,3]dioxol-4-yloxy)acetate Compound 4 (39 g) was dissolved in ethanol (20V). Ceric ammonium nitrate (59.49 g) was added. The resulting reaction mixture was heated to 50-70° C. for 10-12 hrs. The reaction mixture was then quenched with water (500 mL) and extracted with DCM (2×3V). The DCM layer was distilled off. The thus obtained residue was suspended in ethanol (5V) and oxalic acid (13.68 g) was added. This reaction mixture was heated to 65° C. for 2 hours, and then cooled to room temperature and stirred for 8-10 hours. The ethanol layer was distilled off and the resulting residue was purified by crystallization from diisopropyl ether (400 mL) and filtered to give (25.2 g).

Example 7

Preparation of ethyl 2-((3aR,4S,6R,6aS)-6-(6-chloro-5-nitro-2-(propylthio)-pyrimidin-4-ylamino)-2,2-dimethyltetrahydro-3aH-cyclopenta[d][1,3]dioxol-4-yloxy)-acetate (compound 7)

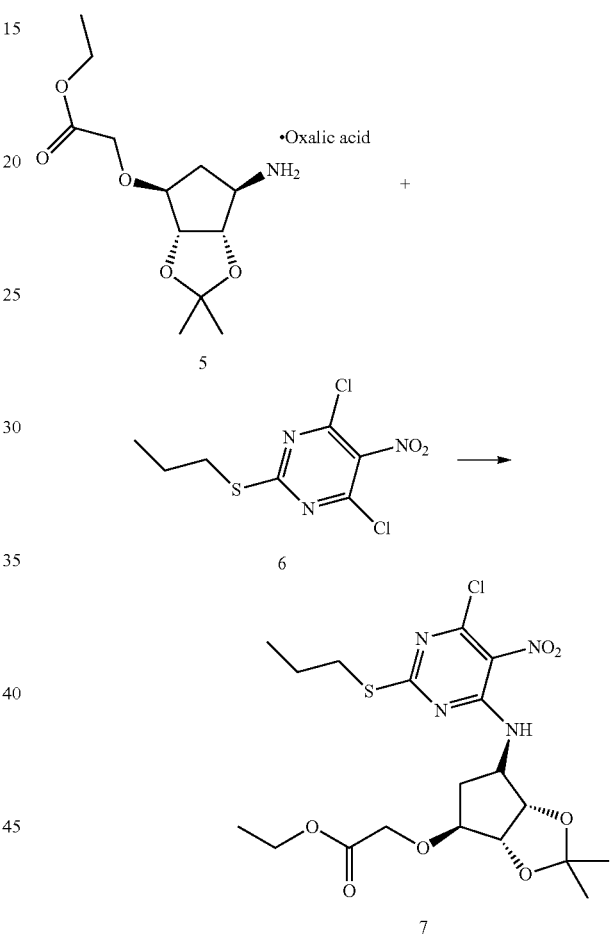

A solution of compound 5 (25.0 g) in water (10-30V) and NaHCO$_3$ (21.04 g) was added dropwise to a solution of compound 6 (38.37 g) in THF (5-15V) at 0-35° C. The resulting reaction mixture was stirred at RT for 1-3 hours. The THF layer was then distilled off. The thus obtained residue was extracted with ethyl acetate (2×300 mL). The extract was concentrated and the resulting residue was purified by column chromatography on silica to give compound 7 (28.6 g).

$^1$H NMR (400 MHz, CDCl$_3$): δ 4.74-4.57 (m, 2H), 4.58 (d, J=4 Hz, 1H), 4.27-4.23 (m, 4H), 4.08 (d, J=4 Hz, 1H), 3.17-3.08 (m, 2H), 2.37-2.33 (m, 1H), 2.05 (d, J=16 Hz, 1H), 1.82-1.76 (m, 2H), 1.44 (s, 3H), 1.27 (s, 3H), 1.33-1.23 (m, 3H), 1.06 (t, J=8 Hz, 3H).). $^{13}$C NMR (100 MHz, CDCl$_3$) δ 174.05, 170.04, 154.72, 153.97, 110.63, 86.18, 85.03, 82.76, 67.05, 61.27, 57.65, 33.70, 33.16, 31.94, 30.20, 29.71, 26.13, 23.81, 22.73, 14.19, 13.43.

Example 7a

Preparation of ethyl 2-((3aR,4S,6R,6aS)-6-(6-chloro-5-nitro-2-(propylthio)-pyrimidin-4-ylamino)-2,2-dimethyltetrahydro-3aH-cyclopenta[d][1,3]dioxol-4-yloxy)-acetate (compound 7)

A solution of compound 5 (25.0 g) in water (200 mL) and NaHCO$_3$ (21.04 g) was added dropwise to a solution of compound 6 (38.37 g) in THF (8V) at 5° C. The resulting reaction mixture was stirred at RT for 1 hour. The THF layer was then distilled off. The thus obtained residue was extracted with ethyl acetate (2×300 mL). The extract was concentrated and the resulting residue was purified by column chromatography on silica to give compound 7 (28.6 g).

$^1$H NMR (400 MHz, CDCl$_3$): δ 4.74-4.57 (m, 2H), 4.58 (d, J=4 Hz, 1H), 4.27-4.23 (m, 4H), 4.08 (d, J=4 Hz, 1H), 3.17-3.08 (m, 2H), 2.37-2.33 (m, 1H), 2.05 (d, J=16 Hz, 1H), 1.82-1.76 (m, 2H), 1.44 (s, 3H), 1.27 (s, 3H), 1.33-1.23 (m, 3H), 1.06 (t, J=8 Hz, 3H).). $^{13}$C NMR (100 MHz, CDCl$_3$) δ 174.05, 170.04, 154.72, 153.97, 110.63, 86.18, 85.03, 82.76, 67.05, 61.27, 57.65, 33.70, 33.16, 31.94, 30.20, 29.71, 26.13, 23.81, 22.73, 14.19, 13.43.

Example 8

Preparation of ethyl 2-((3aR,4S,6R,6aS)-6-(5-amino-6-chloro-2-(propylthio)-pyrimidin-4-ylamino)-2,2-dimethyltetrahydro-3aH-cyclopenta[d][1,3]dioxol-4-yloxy)-acetate

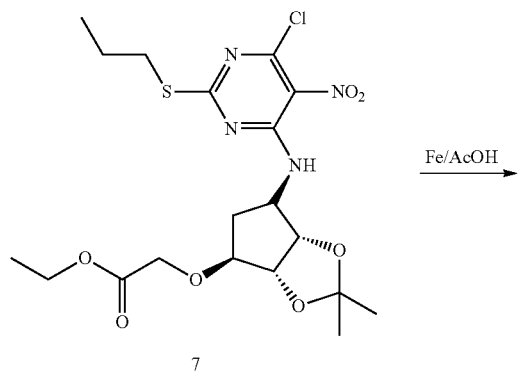

Iron powder (3.07 g) was added to a solution of compound 7 (9 g) in methanol (3-10V) and acetic acid (28 mL). The reaction mixture was then stirred at 20-35° C. for 1-4 hours. The reaction was monitored by TLC. After the reaction was complete, the product was extracted with ethyl acetate. The extract was concentrated under reduced pressure to give compound 8 (8.0 g). The crude product was used for the next step without further purification.

$^1$H NMR (400 MHz, CDCl$_3$): δ 6.36 (d, J=8 Hz, 1H), 4.66 (t, J=8 Hz, 1H), 4.60-4.56 (m, 2H), 4.36-4.06 (m, 4H), 4.00 (d, J=4 Hz, 1H), 3.79 (brs, 2H), 3.19-3.12 (m, 1H), 3.05-2.98 (m, 1H), 2.34-2.28 (m, 1H), 1.91 (d, J=16 Hz, 1H), 1.81-1.71 (m, 2H), 1.44 (s, 3H), 1.31 (t, J=4 Hz, 3H), 1.26 (s, 3H), 1.03 (t, J=8 Hz, 3H). $^{13}$C NMR (100 MHz, CDCl$_3$) δ 171.49, 159.59, 152.71, 141.74, 118.43, 110.36, 86.93, 84.80, 83.05, 67.07, 61.79, 56.80, 33.16, 32.70, 31.96, 29.73, 29.40, 26.18, 23.80, 23.33, 14.16, 13.58.

Example 8a

Preparation of ethyl 2-((3aR,4S,6R,6aS)-6-(5-amino-6-chloro-2-(propylthio)pyrimidin-4-ylamino)-2,2-dimethyltetrahydro-3aH-cyclopenta[d][1,3]dioxol-4-yloxy)acetate Iron powder (8.53 g) was added to a solution of compound 7 (25 g) in methanol (5V) and acetic acid (76.37 mL). The reaction mixture was then stirred at 35° C. for 2 hrs. The reaction was monitored by TLC. After the reaction was complete, the product was extracted with ethyl acetate. The extract was concentrated under reduced pressure to give compound 8 (8.0 g), which was used for the next step without further purification.

$^1$H NMR (400 MHz, CDCl$_3$): δ 6.36 (d, J=8 Hz, 1H), 4.66 (t, J=8 Hz, 1H), 4.60-4.56 (m, 2H), 4.36-4.06 (m, 4H), 4.00 (d, J=4 Hz, 1H), 3.79 (brs, 2H), 3.19-3.12 (m, 1H), 3.05-2.98 (m, 1H), 2.34-2.28 (m, 1H), 1.91 (d, J=16 Hz, 1H), 1.81-1.71 (m, 2H), 1.44 (s, 3H), 1.31 (t, J=4 Hz, 3H), 1.26 (s, 3H), 1.03 (t, J=8 Hz, 3H). $^{13}$C NMR (100 MHz, CDCl$_3$) δ 171.49, 159.59, 152.71, 141.74, 118.43, 110.36, 86.93, 84.80, 83.05, 67.07, 61.79, 56.80, 33.16, 32.70, 31.96, 29.73, 29.40, 26.18, 23.80, 23.33, 14.16, 13.58.

Example 9

Preparation of ethyl 2-((3aR,4S,6R,6aS)-6-(7-chloro-5-(propylthio)-3H-[1,2,3]triazole[4,5-d]pyrimidin-3-yl)-2,2-dimethyltetrahydro-3aH-cyclopenta[d][1,3]-dioxol-4-yloxy)acetate (compound 9)

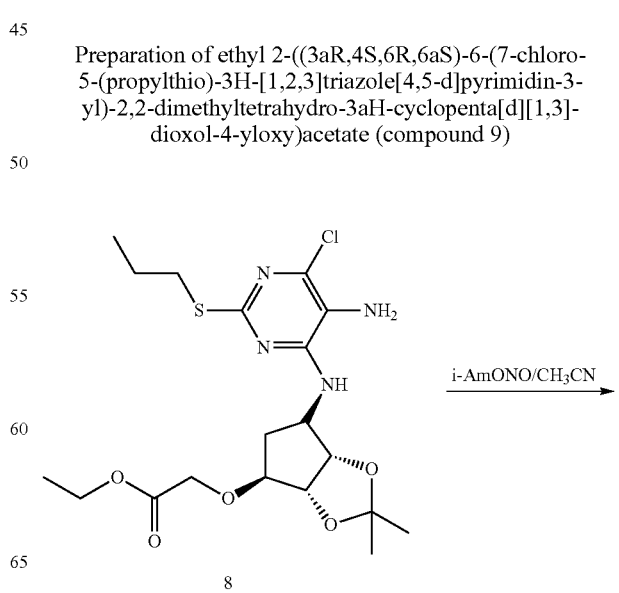

-continued

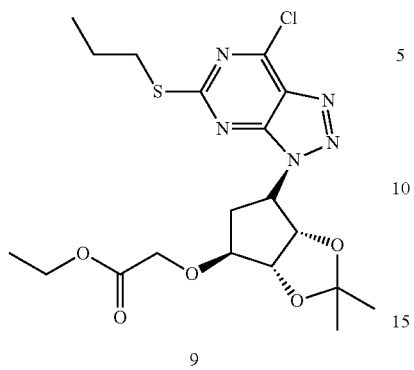

9

To a solution of compound 8 (7.5 g) in acetonitrile (10-15V) was added isoamylnitrite (2.91 g). The reaction mixture was heated to 50-70° C. for 1-5 h. Then the reaction mixture was cooled to room temperature and concentrated at reduced pressure to give compound 9 (6.5 g). The crude product was used for next step without further purification.

$^1$H NMR (400 MHz, CDCl$_3$): δ 5.54 (dd, J=8 Hz, J=4 Hz, 1H), 5.21-5.17 (m, 1H), 4.86 (dd, J=8 Hz, J=4 Hz, 1H), 4.25-4.03 (m, 5H), 3.25-3.16 (m, 2H), 2.82-2.71 (m, 2H), 1.87-1.79 (m, 2H), 1.41 (s, 3H), 1.32-1.20 (m, 6H), 1.10 (t, J=8 Hz, 3H). $^{13}$C NMR (100 MHz, CDCl$_3$) δ 171.52, 169.74, 166.85, 155.19, 153.14, 150.63, 132.10, 112.86, 103.67, 87.22, 83.88, 83.49, 82.40, 66.66, 62.92, 61.07, 42.99, 35.67, 33.74, 29.73, 26.79, 24.54, 22.73, 22.20, 18.05, 15.55.

Example 9a

Preparation of ethyl 2-((3aR,4S,6R,6aS)-6-(7-chloro-5-(propylthio)-3H-[1,2,3]triazole[4,5-d]pyrimidin-3-yl)-2,2-dimethyltetrahydro-3aH-cyclopenta[d][1,3]-dioxol-4-yloxy)acetate (compound 9)

To a solution of compound 8 (20 g) in acetonitrile (10V) was added isoamylnitrite (7.77 g). The reaction mixture was heated to 40° C. for 2 hours. Then the reaction mixture was cooled to room temperature and concentrated at reduced pressure to give compound 9 (19.5 g). The crude product was used for next step without further purification.

$^1$H NMR (400 MHz, CDCl$_3$): δ 5.54 (dd, J=8 Hz, J=4 Hz, 1H), 5.21-5.17 (m, 1H), 4.86 (dd, J=8 Hz, J=4 Hz, 1H), 4.25-4.03 (m, 5H), 3.25-3.16 (m, 2H), 2.82-2.71 (m, 2H), 1.87-1.79 (m, 2H), 1.41 (s, 3H), 1.32-1.20 (m, 6H), 1.10 (t, J=8 Hz, 3H). $^{13}$C NMR (100 MHz, CDCl$_3$) δ 171.52, 169.74, 166.85, 155.19, 153.14, 150.63, 132.10, 112.86, 103.67, 87.22, 83.88, 83.49, 82.40, 66.66, 62.92, 61.07, 42.99, 35.67, 33.74, 29.73, 26.79, 24.54, 22.73, 22.20, 18.05, 15.55.

Example 10

Preparation of ethyl 2-((3aS,4R,6S,6aR)-4-(7-((1R,2S)-2-(3,4-difluoro-phenyl)cyclopropylamino)-5-(propylthio)-3H-[1,2,3]triazolo[4,5-d]pyrimidin-3-yl)tetrahydro-3aH-spiro[cyclopenta[d][1,3]dioxole-2,1'-cyclopentane]-6-yloxy)acetate (compound 11)

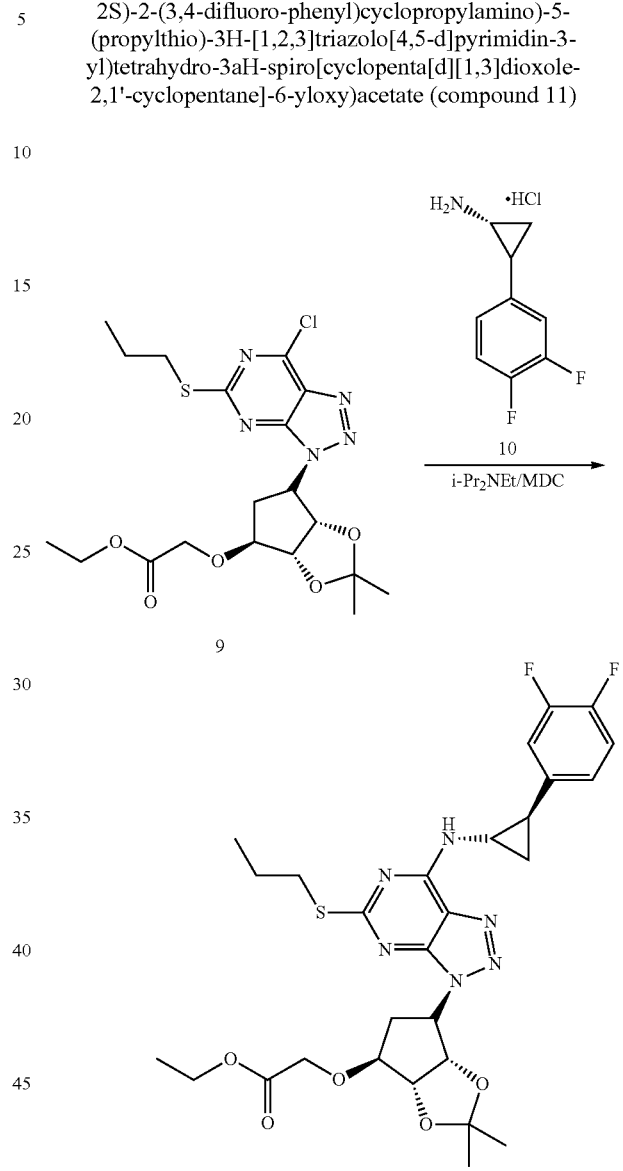

To a solution of compound 10 (3.35 g) in DCM (5-15V) was added diisopropylethylamine (DIPEA) (5.75 g). A solution of compound 9 (6.2 g) in DCM (10-15V) was then added. The reaction mixture was stirred at 25-35° C. for 1-5 hours and then the aqueous and organic layers were separated. The aqueous layer was extracted with DCM (100 mL). The combined organic layer was then concentrated to dryness. The crude product was purified by column chromatography to give compound 11 (3.5 g).

$^1$H NMR (400 MHz, CDCl$_3$): δ 7.16-7.04 (m, 3H), 6.77 (brs, 1H), 5.46-5.43 (m, 1H), 5.14-5.09 (m, 1H), 4.81 (dd, J=8 Hz, J=4 Hz, 1H), 4.20 (q, J=8 Hz, 2H), 4.13-4.08 (m, 3H), 3.10-3.02 (m, 3H), 2.72 (t, J=8 Hz, 2H), 2.60 (brs, 1H), 1.73-1.68 (m, 3H), 1.54 (s, 3H), 1.38-1.33 (m, 2H), 1.27 (t, J=8 Hz, 3H), 0.98 (t, J=8 Hz, 3H). $^{13}$C NMR (100 MHz, CDCl$_3$) δ 1.69.88, 150.35, 149.57, 149.06, 147.91, 140.90, 137.31, 123.56, 123.00, 117.13, 116.96, 115.89, 113.43, 113.08, 94.82, 84.05, 83.50, 76.72, 66.80, 61.78, 61.00, 45.73, 36.02, 33.26, 32.96, 25.03, 24.72, 22.72, 15.50, 14.19, 13.48.

Example 10a

Preparation of ethyl 2-((3aS,4R,6S,6aR)-4-(7-((1R,2S)-2-(3,4-difluoro-phenyl)cyclopropylamino)-5-(propylthio)-3H-[1,2,3]triazolo[4,5-d]pyrimidin-3-yl)tetrahydro-3aH-spiro[cyclopenta[d][1,3]dioxole-2,1'-cyclopentane]-6-yloxy)acetate (compound 11)

To a solution of compound 10 (7.75 g) in DCM (5V) was added DIPEA (18.75 g). A solution of compound 9 (15 g) in DCM (5 V) was then added. The reaction mixture was stirred at 35° C. for 4 hours and then the aqueous and organic layers were separated. The aqueous layer was extracted with DCM (200 mL). The combined organic layer was then concentrated to dryness. The crude product was purified by column chromatography (eluted with 5% methanol in DCM) to give compound 11 (24.87 g).

$^1$H NMR (400 MHz, CDCl$_3$): δ 7.16-7.04 (m, 3H), 6.77 (brs, 1H), 5.46-5.43 (m, 1H), 5.14-5.09 (m, 1H), 4.81 (dd, J=8 Hz, J=4 Hz, 1H), 4.20 (q, J=8 Hz, 2H), 4.13-4.08 (m, 3H), 3.10-3.02 (m, 3H), 2.72 (t, J=8 Hz, 2H), 2.60 (brs, 1H), 1.73-1.68 (m, 3H), 1.54 (s, 3H), 1.38-1.33 (m, 2H), 1.27 (t, J=8 Hz, 3H), 0.98 (t, J=8 Hz, 3H). $^{13}$C NMR (100 MHz, CDCl$_3$) δ 1.69.88, 150.35, 149.57, 149.06, 147.91, 140.90, 137.31, 123.56, 123.00, 117.13, 116.96, 115.89, 113.43, 113.08, 94.82, 84.05, 83.50, 76.72, 66.80, 61.78, 61.00, 45.73, 36.02, 33.26, 32.96, 25.03, 24.72, 22.72, 15.50, 14.19, 13.48.

Example 11

Preparation of 2-((3 aS,4R,6S,6aR)-4-(7-((1R,2S)-2-(3,4-difluorophenyl)-cyclopropylamino)-5-(propylthio)-3H-[1,2,3]triazolo[4,5-d]pyrimidin-3-yl)tetrahydro-3aH-spiro[cyclopenta[d][1,3]dioxole-2,1'-cyclopentane]-6-yloxy)ethanol (compound 12)

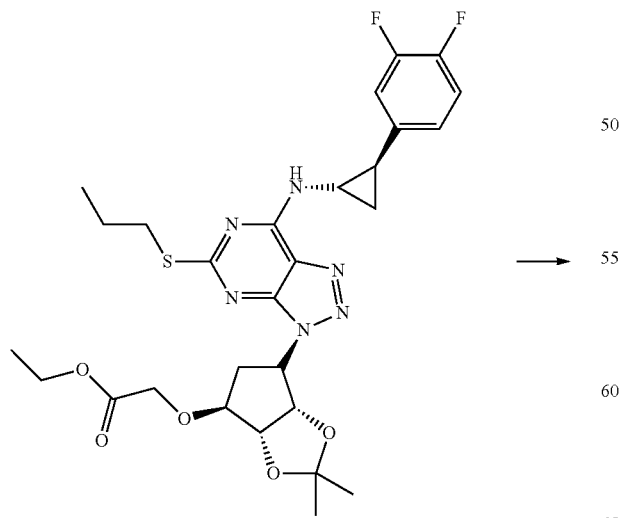

11

⟶

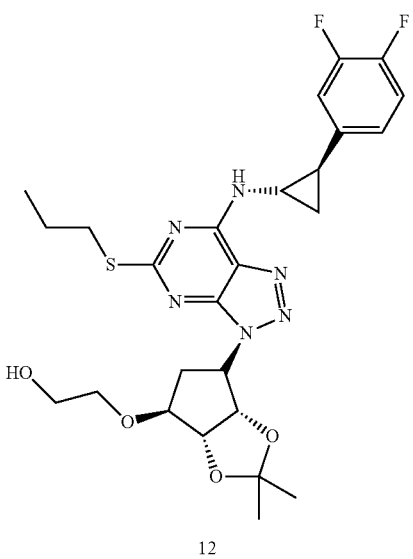

12

Compound 11 (2.0 g) in THF (30 mL) was reduced in presence of lithium borohydride (0.216 g) at 0 to 30° C. The reaction mixture was stirred at 0-30° C. for 10-12 hrs. The reaction was monitored by TLC. After completion, the reaction was quenched with water (50 mL), and the THF was distilled off under reduced pressure to provide a residue. The residue was extracted with ethyl acetate (5.0 vol). The extract was washed with water (75 mL) and then concentrated at reduced pressure to provide the crude product as a viscous mass (1.59 g, 95.72%). This crude product was used for next step without further purification.

Example 11a

Preparation of 2-((3aS,4R,6S,6aR)-4-(7-((1R,2S)-2-(3,4-difluorophenyl)-cyclopropylamino)-5-(propylthio)-3H-[1,2,3]triazolo[4,5-d]pyrimidin-3-yl)tetrahydro-3aH-spiro[cyclopenta[d][1,3]dioxole-2,1'-cyclopentane]-6-yloxy)ethanol (compound 12)

Compound 11 (20 g) in THF (200 mL) was reduced in presence of lithium borohydride (2.16 g) at 25-30° C. The reaction mixture was stiffed at 25-30° C. for 4 hrs. The reaction was monitored by TLC. After completion, the reaction was quenched with water (50 mL), and the THF was distilled off under reduced pressure to provide a residue. The residue was extracted with ethyl acetate (5.0 vol). The extract was washed with water (75 mL) and then concentrated at reduced pressure to provide the crude product as a viscous mass (20 g, 95.72%). This crude product was used for next step without further purification.

Example 12

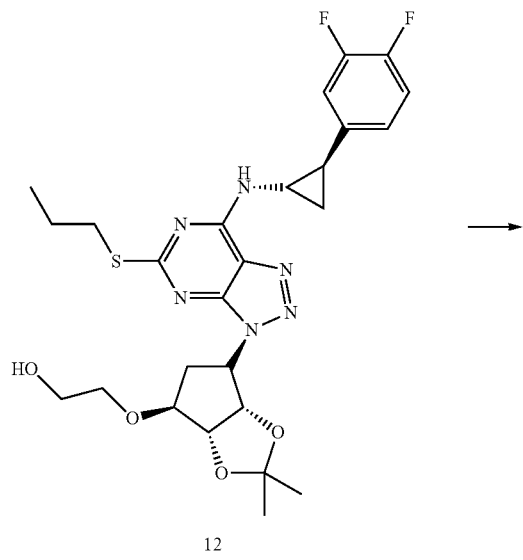

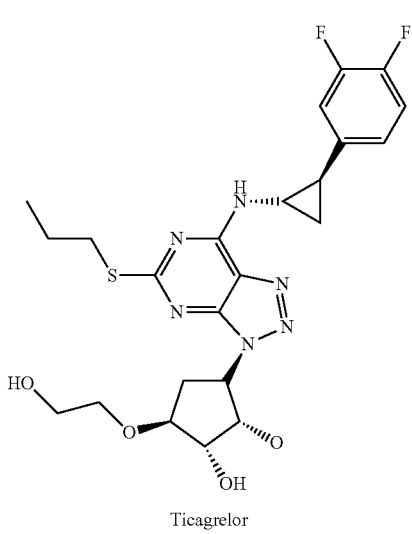

Ticagrelor

To a solution of compound 12 (1.56 g) in methanol (10 vol) was added a solution of hydrochloric acid (1.24 ml) in water (2 mL) at 25-30° C. The reaction mixture was stirred at 25-30° C. for 4-6 hrs. The reaction was monitored by TLC. After completion, the methanol was distilled off under reduced pressure. The obtained residue was taken up in water and extracted with ethyl acetate (100 mL). The extract was washed with aqueous sodium bicarbonate (50 mL) and then the ethyl acetate was removed by distillation to provide the crude product. The crude product was crystallized from a mixture of ethyl acetate and diisopropylether to provide a white solid.

Example 13

Preparation of 4,6-dichloro-2-(propylthio)pyrimidin-5-amine

Iron powder (15.62 g) was added to a solution of compound 6 in methanol (10 vol) and acetic acid (5.0 vol) at RT. The resulting reaction mixture was stirred for 3-5 hrs at 50° C. The reaction was monitored by TLC. The product was extracted by adding water (5.0 vol). The resulting mixture was filtered and the filtrate was distilled off under reduced pressure at 40-50° C. to form a residue. The obtained residue was extracted with ethyl acetate (500-600 ml). The ethyl acetate extract was washed with aqueous sodium bicarbonate and then concentrated under reduced pressure. The thus obtained residue was crystallized. Isolated yield 90-95%. $^1$H NMR (400 MHz, CDCl$_3$): δ 4.22 (brs, 2H), 3.07 (t, J=8 Hz, 2H), 1.77-1.68 (m, 2H), 1.03 (t, J=8 Hz, 3H). $^{13}$C NMR (100 MHz, CDCl$_3$) δ 158.60, 145.27, 131.48, 33.38, 22.42, 13.45.

Example 13a

Synthesis of 4,6-dichloro-2-(propylthio)pyrimidin-5-amine

Iron powder (15.62 g) was added to a solution of compound 6 (25 g) in methanol (10 vol) and acetic acid (5.0 vol) at RT. The resulting reaction mixture was stirred for 4 hrs at 50° C. The reaction was monitored by TLC. After the reaction was complete, the reaction mixture was filtered and the collected solid was washed with methanol (10V). The combined filtrate was concentrated do dryness under reduced pressure at 40-50° C. The thus-obtained residue was redissolved in ethyl acetate (600 mL). The ethyl acetate solution was washed with aqueous sodium bicarbonate and then concentrated under reduced pressure. The thus-obtained residue was crystallized from n-hexane (80 mL) at −20° C. to provide the product in 76% yield.

$^1$H NMR (400 MHz, CDCl$_3$): δ 4.22 (brs, 2H), 3.07 (t, J=8 Hz, 2H), 1.77-1.68 (m, 2H), 1.03 (t, J=8 Hz, 3H). $^{13}$C NMR (100 MHz, CDCl$_3$) δ 158.60, 145.27, 131.48, 33.38, 22.42, 13.45.

Example 14

Preparation of ethyl 2-((3aR,4S,6R,6aS)-6-(5-amino-6-chloro-2-(propyl-thio)pyrimidin-4-ylamino)-2,2-dimethyltetrahydro-3aH-cyclopenta[d][1,3]dioxol-4-yloxy)acetate

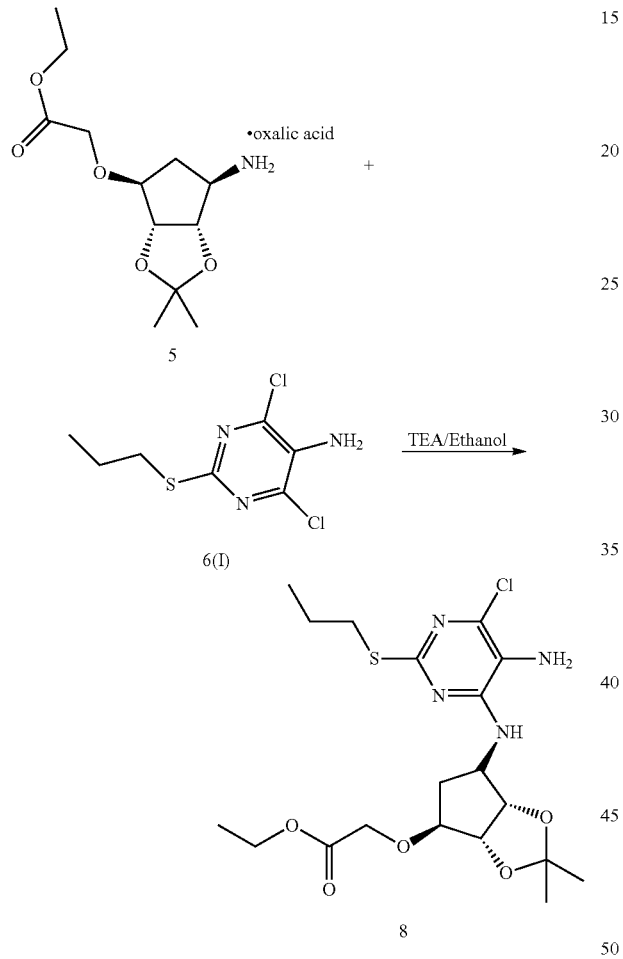

Compound 5 (3.0 g) and compound 6(I) (1.7 g) were condensed in ethanol (69 mL) in presence of triethylamine (2.53 g) in an autoclave. The autoclave was flushed with nitrogen and pressurized to 5 kg/cm$^2$ with nitrogen. The autoclave was then heated to 125° C. The reaction mixture was stirred for 36 hrs at this temperature. The reaction was monitored by TLC. When the reaction was complete, the solvent was distilled off to provide a residue. The residue was taken up in water (50 mL) and extracted with ethyl acetate (2×50 mL). The extract was then concentrated under reduced pressure. The thus obtained crude product was then purified.

$^1$H NMR (400 MHz, CDCl$_3$): δ 6.36 (d, J=8 Hz, 1H), 4.66 (t, J=8 Hz, 1H), 4.60-4.56 (m, 2H), 4.36-4.06 (m, 4H), 4.00 (d, J=4 Hz, 1H), 3.79 (brs, 2H), 3.19-3.12 (m, 1H), 3.05-2.98 (m, 1H), 2.34-2.28 (m, 1H), 1.91 (d, J=16 Hz, 1H), 1.81-1.71 (m, 2H), 1.44 (s, 3H), 1.31 (t, J=4 Hz, 3H), 1.26 (s, 3H), 1.03 (t, J=8 Hz, 3H). $^{13}$C NMR (100 MHz, CDCl$_3$) δ 171.49, 159.59, 152.71, 141.74, 118.43, 110.36, 86.93, 84.80, 83.05, 67.07, 61.79, 56.80, 33.16, 32.70, 31.96, 29.73, 29.40, 26.18, 23.80, 23.33, 14.16, 13.58.

Example 15

Preparation of ethyl 2-((3aR,4S,6R,6aS)-6-(5-amino-6-chloro-2-(propylthio)pyrimidin-4-ylamino)-2,2-dimethyltetrahydro-3aH-clopenta[d][1,3]dioxol-4-yloxy)acetate

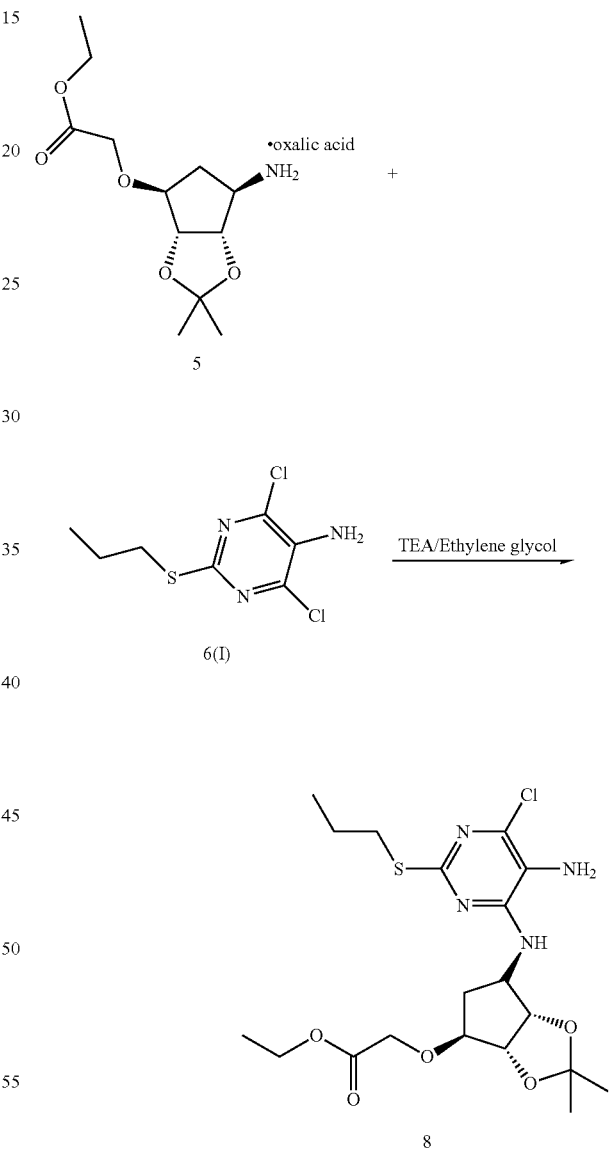

To a mixture of Compound 5 (5.0 g), compound 6(I) (4.77 g) and ethylene glycol (10 g) was added triethylamine (5.99 g). The resulting reaction mixture was heated to 100° C. for 12 h under an inert atmosphere. The reaction was monitored by TLC. After completion of reaction, the reaction mixture was quenched by addition of water (100 mL). The layers were separated and the aqueous layer was extracted with ethyl acetate (5.0 vol). The combined organic fraction was then concentrated under reduced pressure. The obtained crude product used for next hydrolysis step.

Example 16

Preparation of ethyl 2-((3aR,4S,6R,6aS)-6-(5-amino-6-chloro-2-(propylthio)pyrimidin-4-ylamino)-2,2-dimethyltetrahydro-3aH-cyclopenta[d][1,3]dioxol-4-yloxy)acetate

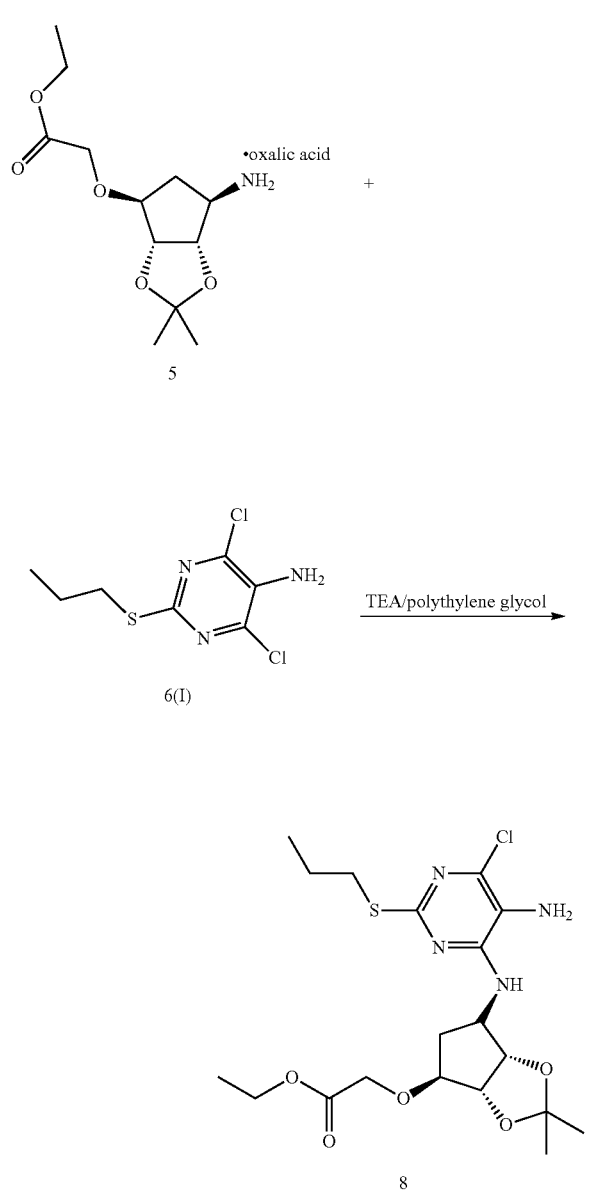

To a mixture of compound 5 (5.0 g), compound 6(I) (4.77 g) and polyethylene glycol (10 g) was added triethylamine (5.99 g) under an inert atmosphere. The resulting reaction mixture was heated to 100° C. for 6-10 hrs. The reaction was monitored by TLC and HPLC. After completion of the reaction, it was quenched by addition of water (100 mL). The layers were separated and the aqueous layer was extracted with ethyl acetate (100 mL). The combined organic fraction was then concentrated under reduced pressure to provide the crude product. The crude product was used for next hydrolysis.

Example 17

Preparation of ethyl 2-((3aR,4S,6R,6aS)-6-(5-amino-6-chloro-2-(propylthio)pyrimidin-4-ylamino)-2,2-dimethyltetrahydro-3aH-cyclopenta[d][1,3]dioxol-4-yloxy)acetate

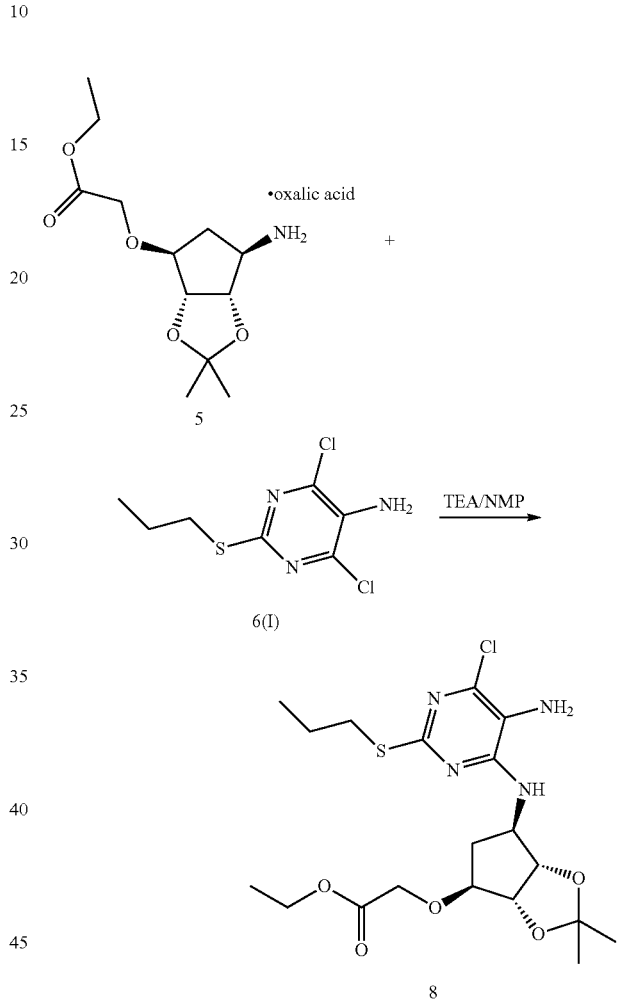

Compound 5 (25.0 g), was condensed with compound 6(I) (23.85 g) in N-methyl-2-pyrrolidinone (125 mL) and triethylamine (29.98 g) under an inert atmosphere. The reaction mixture was heated to 70-100° C. for 6-12 h. The reaction was monitored by TLC and HPLC. When the reaction was complete, it was quenched by addition of water (125 mL). The aqueous layer was separated and extracted with ethyl acetate (2×125 mL). The combined organic fraction was then concentrated under reduced pressure to provide the crude product, which was used for next step

Example 17a

Preparation of ethyl 2-((3aR,4S,6R,6aS)-6-(5-amino-6-chloro-2-(propylthio)pyrimidin-4-ylamino)-2,2-dimethyltetrahydro-3aH-cyclopenta[d][1,3]dioxol-4-yloxy)acetate Compound 5 (25.0 g), was condensed with compound 6(I) (23.85 g) in N-methyl-2-pyrrolidinone (125 mL) and triethylamine (29.98 g) under an inert atmosphere. The reaction mixture was heated to 85° C. for 6 hours. The reaction was monitored by TLC and HPLC. When the reaction was complete, it was quenched by addition of water (125 mL). The aqueous layer was separated and extracted with ethyl acetate (2×125 mL). The combined organic fraction was then concentrated under reduced pressure to provide the crude product, which was used for next step.

Example 18

Preparation of 2-((3aR,4S,6R,6aS)-6-(5-amino-6-chloro-2-(propylthio)-pyrimidin-4-ylamino)-2,2-dimethyltetrahydro-3aH-cyclopenta[d][1,3]dioxol-4-yloxy)-acetic acid (compound 8a)

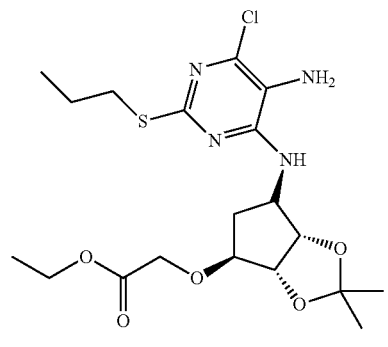

Crude compound 8 (20.0 g) was hydrolyzed in a methanol (100 mL) and water mixture in the presence of NaOH (4.34 g) at RT. The reaction mixture was stirred at 0-30° C. for 4-12 hrs. The reaction was monitored by TLC. After completion of the reaction, the methanol was distilled off under reduced pressure. The remaining aqueous layer was washed with ethyl acetate (3×50 mL) to recover compound 6(I), and the aqueous layer was then acidified with acetic acid. The aqueous layer was then extracted with ethyl acetate (200 ml). The extract was concentrated under reduced pressure to provide compound 8a as a white solid (14 g, 80-90%).

$^1$H NMR (400 MHz, DMSO-D$_6$): δ 13.0 (brs, 1H), 6.78 (d, J=8 Hz, 1H), 4.56-4.49 (m, 2H), 4.28 (brs, 1H), 4.20-4.02 (m, 2H), 3.96 (brs, 1H), 2.97 (t, J=8 Hz, 1H), 2.26-2.23 (m, 1H), 1.84 (d, J=12 Hz, 1H), 1.65-1.60 (m, 2H), 1.36 (s, 3H), 1.20 (s, 3H), 0.94 (t, J=8 Hz, 3H);. $^{13}$C NMR (100 MHz, DMSO-D$_6$) δ 172.93, 156.09, 152.36, 138.76, 120.33, 110.70, 84.87, 84.52, 83.57, 67.76, 66.63, 57.07, 33.87, 32.58, 26.90, 24.59, 23.41, m23.27, 13.79.

Example 18a

Preparation of 2-((3aR,4S,6R,6aS)-6-(5-amino-6-chloro-2-(propylthio)-pyrimidin-4-ylamino)-2,2-dimethyltetrahydro-3aH-cyclopenta[d][1,3]dioxol-4-yloxy)-acetic acid (compound 8a)

Crude compound 8 (20.0 g) was dissolved in THF (100 mL). An aqueous NaOH solution (4.34 g NaOH in 50 mL water) was added dropwise at 25-30° C. The resulting mixture was stirred at 25-30° C. for 2 hours. The reaction was monitored by TLC. After completion of the reaction, the mixture was concentrated under reduced pressure to remove the organic solvent. The remaining aqueous layer was washed with ethyl acetate (3×75 mL) to recover compound 6(I). The aqueous layer was then acidified with acetic acid. The aqueous layer was then extracted with ethyl acetate (3×75 ml). The extract was concentrated under reduced pressure to provide compound 8a as a white solid (18.5 g, 59.71% yield).

$^1$H NMR (400 MHz, DMSO-D$_6$): δ 13.0 (brs, 1H), 6.78 (d, J=8 Hz, 1H), 4.56-4.49 (m, 2H), 4.28 (brs, 1H), 4.20-4.02 (m, 2H), 3.96 (brs, 1H), 2.97 (t, J=8 Hz, 1H), 2.26-2.23 (m, 1H), 1.84 (d, J=12 Hz, 1H), 1.65-1.60 (m, 2H), 1.36 (s, 3H), 1.20 (s, 3H), 0.94 (t, J=8 Hz, 3H);. $^{13}$C NMR (100 MHz, DMSO-D$_6$) δ 172.93, 156.09, 152.36, 138.76, 120.33, 110.70, 84.87, 84.52, 83.57, 67.76, 66.63, 57.07, 33.87, 32.58, 26.90, 24.59, 23.41, m23.27, 13.79.

Example 19

2-((3aR,4S,6R,6aS)-6-(7-chloro-5-(propylthio)-3H-[1,2,3]triazolo[4,5-d]pyrimidin-3-yl)-2,2-dimethyltetrahydro-3aH-cyclopenta[d][1,3]dioxol-4-yloxy) acetic acid (compound 9a)

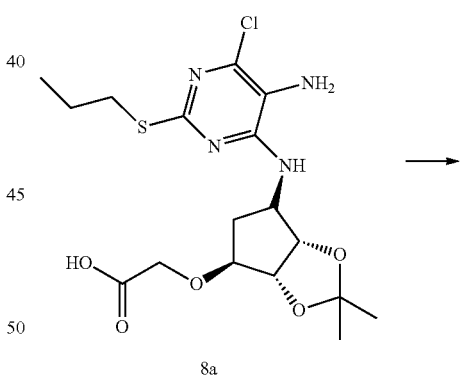

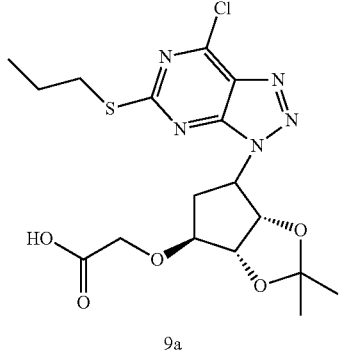

To a solution of compound 8a (10 g) in acetonitrile (100 mL) was added isoamylnitrite (4.0 g) at 10-30° C. The reaction mixture was stirred at 50-70° C. for 3-5 h. The reaction was monitored by TLC. After completion, the reaction was quenched with 10% aqueous NaHSO₃ (10 ml) and concentrated under reduced pressure. The obtained residue was extracted with ethyl acetate (10 vol). The extract was washed with water and then concentrated at reduced pressure to provide the product (9.5 g, 92.68%).

¹H NMR (400 MHz, DMSO-Ds): δ 12.5 (brs, 1H), 5.37 (m, 3H), 4.10-3.93 (m, 3H), 3.21-3.13 (m, 2H), 2.74-2.49 (m, 2H), 1.80-1.71 (m, 213), 1.47 (s, 3H), 1.27 (s, 3H), 1.01 (t, J=8 Hz, 3H);. ¹³C NMR (100 MHz, DMSO-D₆) δ 171.47, 170.19, 162.79, 152.30, 151.01, 132.29, 112.63, 83.91, 82.86, 82.34, 66.29, 36.26, 35.04, 33.35, 31.24, 27.16, 25.05, 22.30, 13.74.

Example 19a 2-((3aR,4S,6R,6aS)-6-(7-chloro-5-(propylthio)-3H-[1,2,3]triazolo[4,5-d]pyrimidin-3-yl)-2,2-dimethyltetrahydro-3aH-cyclopenta[d][1,3]dioxol-4-yloxy)acetic acid (compound 9a)

To a solution of compound 8a (18 g) in acetonitrile (150 mL) was added isoamylnitrite (7.45 g) at 30° C. The reaction mixture was stirred at 25-30° C. for 45 minutes. The reaction was monitored by TLC. After completion, the reaction was quenched with 10% NaHSO₃ solution in water (10 ml) and concentrated under reduced pressure. The obtained residue was extracted with ethyl acetate (10 vol). The extract was washed with water and then concentrated at reduced pressure to provide the product (21 g, 92.68%).

¹H NMR (400 MHz, DMSO-D₆): δ 12.5 (brs, 1H), 5.37 (m, 3H), 4.10-3.93 (m, 3H), 3.21-3.13 (m, 2H), 2.74-2.49 (m, 2H), 1.80-1.71 (m, 2H), 1.47 (s, 3H), 1.27 (s, 3H), 1.01 (t, J=8 Hz, 3H);. ¹³C NMR (100 MHz, DMSO-D₆) δ 171.47, 170.19, 162.79, 152.30, 151.01, 132.29, 112.63, 83.91, 82.86, 82.34, 66.29, 36.26, 35.04, 33.35, 31.24, 27.16, 25.05, 22.30, 13.74.

Example 20

Preparation of 2-((3aR,4S,6R,6aS)-6-(7-((1R,2S)-2-(3,4-difluorophenyl)-cyclopropylamino)-5-(propylthio)-3H-[1,2,3]triazolo[4,5-d]pyrimidin-3-yl)-2,2-dimethyltetrahydro-3aH-cyclopenta[d][1,3]dioxol-4-yloxy)acetic acid (compound 11a)

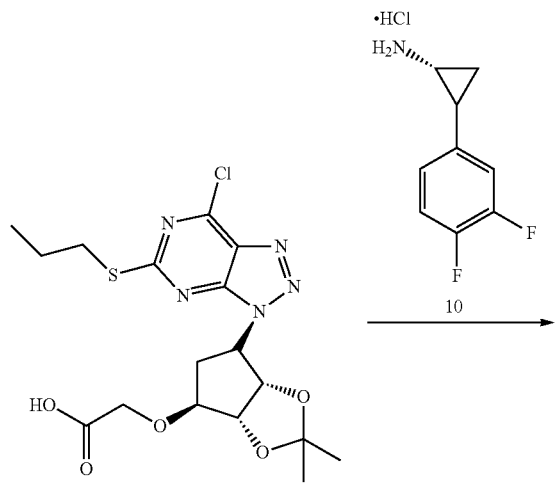

9a

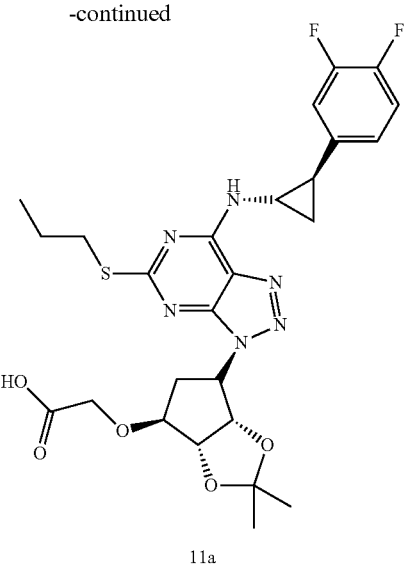

11a

To a solution of compound 10 (4.63 g) in DCM (30 mL) and diisopropylethylamine (4.37 g) at 25-30° C. was added a solution of compound 9a (5 g) in DCM (5.0 vol). The resulting reaction mixture was stirred at less than 30° C. for 10-12 h. The reaction was monitored by TLC. After completion of the reaction, water (100 mL) was added. The organic layer was separated and then concentrated to dryness at 40° C. to give a white solid (4.6 g 70.87%).

¹H NMR (400 MHz, CDCl₃): δ 7.14-7.00 (m, 3H), 5.44 (brs, 1H), 5.23 (d, J=4 Hz, 1H), 4.86 (d, J=4 Hz, 1H), 4.22-4.15 (m, 2H), 4.18 (s, 2H), 3.11-3.04 (m, 2H), 2.65-2.75 (m, 1H), 2.53 (m, 1H), 2.11 (m, 1H), 1.72-1.66 (m, 2H), 1.53 (s, 3H), 1.36 (s, 3H), 1.42-1.34 (m, 1H), 1.26 (s, 2H) 0.96 (t, J=8 Hz, 3H);. ¹³C NMR (100 MHz, CDCl₃) δ 1.72.67, 171.92, 153.91, 150.29, 149.61, 149.04, 147.71, 137.51, 122.97, 122.79, 117.10, 116.93, 115.89, 115.71, 112.26, 84.18, 83.88, 82.95, 66.31, 62.83, 34.73, 33.30, 33.21, 31.94, 29.72, 29.39, 26.62, 24.75, 24.32, 22.70, 15.22, 14.16, 13.45, 1.04.

Example 21

Preparation of 2-((3aR,4S,6R,6aS)-6-(7-((1R,2S)-2-(3,4-difluorophenyl)-cyclopropylamino)-5-(propylthio)-3H-[1,2,3]triazolo[4,5-d]pyrimidin-3-yl)-2,2-dimethyltetrahydro-3aH-cyclopenta[d][1,3]dioxol-4-yloxy)ethanol (compound 12)

11

81
-continued

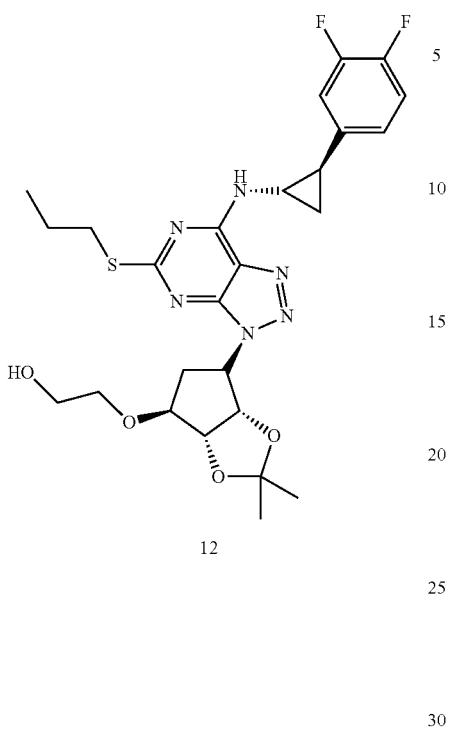

12

LiAlH$_4$ (0.2 g) was added to THF (10 vol) slowly at 0 to −10° C. To this mixture was added a solution of compound 11a (3 g) in THF (15 mL) slowly over 30 min at 0 to −10° C. The reaction mixture was stirred at 0 to −10° C. for 4-12 hrs. The reaction was monitored by TLC. When the reaction was complete, it was quenched and the product was isolated by routine work up. The filtrate was concentrated under reduced pressure, and compound 12 was isolated as an oily mass; yield 14 g, 70-75%.

Example 21a

Preparation of 2-((3aR,4S,6R,6aS)-6-(7-((1R,2S)-2-(3,4-difluorophenyl)-cyclopropylamino)-5-(propylthio)-3H-[1,2,3]triazolo[4,5-d]pyrimidin-3-yl)-2,2-dimethyltetrahydro-3aH-cyclopenta[d][1,3]dioxol-4-yloxy)ethanol (compound 12)

LiAlH$_4$ (0.151 g) was added to THF (35 mL) slowly at −10° C. To this mixture was added a solution of compound 11a (1.5 g) in THF (15 mL) slowly over 30 min at 0 to −10° C. The reaction mixture was stirred at 0 to −10° C. for 2 hrs. The reaction was monitored by TLC. When the reaction was complete, it was quenched by addition of aqueous saturated ammonium chloride (10 mL), followed by addition of ethyl acetate (20 mL). The phases were separated and the organic phase was concentrated. The residue was purified by column chromatography (eluting with 40% ethyl acetate in hexane). The fractions containing the product were concentrated under reduced pressure to provide compound 12 as an oily mass (0.7 g, 70-75% yield).

82

Example 22

Preparation of methyl (2-((1S,2S,3S,4R)-4-(6-chloro-5-nitro-2-(propylthio)-pyrimidin-4-ylamino)-2,3-dihydroxycyclopentyloxy)acetate (compound 7a)

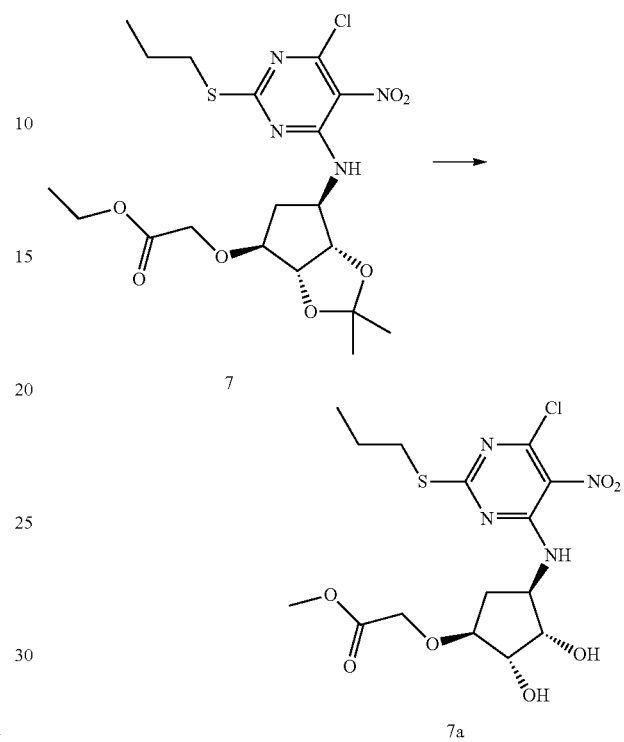

A 50% solution of hydrochloric acid (5.5 mL) was added to a mixture of compound 7 in methanol (75 ml) at room temperature with stirring. The resulting reaction mixture was heated to 50-70° C. for 2-3 hrs. The reaction was monitored by TLC. After completion of the reaction, the mixture was extracted with ethyl acetate and the extract was concentrated to provide a white solid; yield 2.12 g, 45.88%.

$^1$H NMR (400 MHz, CDCl$_3$): δ 8.84 (d, J=4 Hz, 1H), 4.44-4.43 (m, 1H), 4.28 (s, 2H), 4.25-4.18 (m, 4H), 4.04 (m, 1H), 3.83 (s, 3H); 3.24-3.15 (m, 2H); 2.87-2.79 (m, 1H); 1.89-1.81 (m, 3H); 1.13 (t, J=8 Hz, 3H); $^{13}$C NMR (100 MHz) δ 174.62, 171.01, 163.53, 156.61, 83.84, 67.18, 57.25, 55.57, 52.10, 34.88, 33.56, 22.74, 13.46.

Example-23

Preparation of methyl 2-((1S,2S,3S,4R)-4-(5-amino-6-chloro-2-(propylthio)-pyrimidin-4-ylamino)-2,3-dihydroxycyclopentyloxy)acetate (compound 8b)

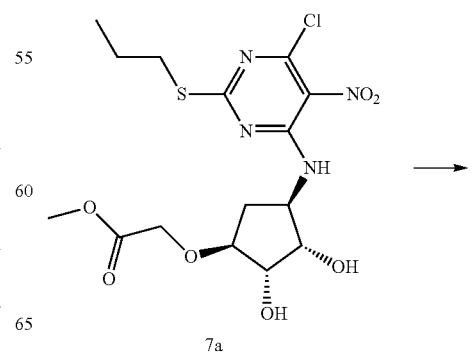

7a

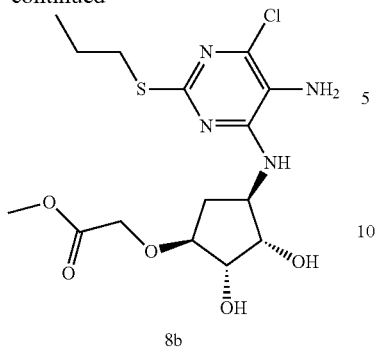

8b

Compound 7a (5 g) was reduced in methanol (10.0 vol) and acetic acid (5.0 vol) at 0-30° C. The reaction mixture was stirred at this temperature for 2-3 h. After completion of the reaction by TLC, the product was extracted with ethyl acetate. The extract was concentrated under reduced pressure to give crude 8b, which was used for the next step directly, Example 23a Preparation of methyl 2-((1S,2S,3S,4R)-4-(5-amino-6-chloro-2-(propylthio)pyrimidin-4-ylamino)-2,3-dihydroxycyclopentyloxy)acetate (compound 8b)

Compound 7a (5 g) was reduced in methanol (10.0 vol) and acetic acid (5.0 vol) at 20-25° C. The reaction mixture was stirred at this temperature for 2-3 h. After completion of the reaction by TLC, the product was extracted with ethyl acetate. The extract was concentrated under reduced pressure to give crude 8b, which was used for the next step directly.

Example 24

Preparation of methyl 2-((1S,2S,3S,4R)-4-(7-chloro-5-(propylthio)-3H-[1,2,3]triazole[4,5-d]pyrimidin-3-yl)-2,3-dihydroxycyclopentyloxy)acetate (compound 9b)

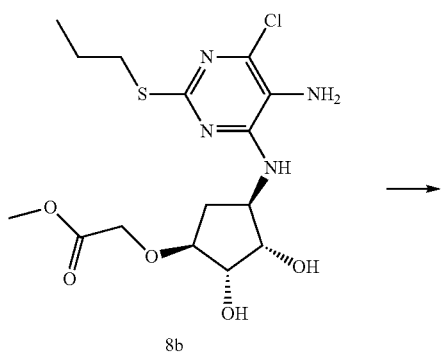

8b

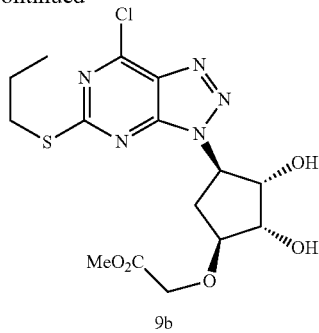

9b

To a solution of compound 8b (4.5 g) in acetonitrile (5-10 vol) was added isoamylnitrite (1.87 g) at 30° C. The reaction mixture was stirred at 40-60° C. for 3-5 h. The reaction was monitored by TLC. After completion, the reaction was quenched with NaHSO₃ solution in water (10 ml) and concentrated under reduced pressure to 80% of its total volume. The product was isolated as a viscous oil (4.2 g, 91%) from ethyl acetate. This crude product was used for the next step without further purification.

$^1$H NMR (400 MHz, CDCl$_3$): δ 5.14 (dd, J=8 Hz, J=12 Hz, 1H), 4.80 (dd, J=8 Hz, J=12 Hz, 1H), 4.48-4.46 (m, 1H), 4.38-4.24 (m, 4H), 4.16-4.12 (m, 1H), 3.85 (s, 3H); 3.23 (t, J=8 Hz, 3H); 3.05-3.00 (m, 1H); 2.62-2.54 (m, 1H); 1.88 (q, J=8 Hz, 2H); 1.15 (t, J=8 Hz, 3H); $^{13}$C NMR (100 MHz) δ 171.19, 160.49, 151.65, 124.15, 83.19, 75.01, 67.13, 61.95, 55.09, 52.13, 33.50, 32.99, 22.99, 14.00

Example 24a

Preparation of ethyl 2-((1S,2S,3S,4R)-4-(7-chloro-5-(propylthio)-3H-[1,2,3]triazole[4,5-d]pyrimidin-3-yl)-2,3-dihydroxycyclopentyloxy)acetate (compound 9b)

To a solution of compound 8b (4.5 g) in acetonitrile (10 vol) was added isoamylnitrite (1.87 g) at 30° C. The reaction mixture was stirred at 60-65° C. for 3-5 h. The reaction was monitored by TLC. After completion, the reaction was quenched with NaHSO₃ solution in water (10 ml) and the acetonitrile was distilled off under reduced pressure to 80% of its total volume. The product was isolated as a viscous oil (4.2 g, 91%) from ethyl acetate. This crude product was used for the next step without further purification.

Example 25

Preparation of ethyl 2-((1S,2S,3S,4R)-4-(7-((1R,2S)-2-(3,4-difluorophenyl)-cyclopropylamino)-5-(propylthio)-3H-[1,2,3]triazolo[4,5-d]pyrimidin-3-yl)-2,3-dihydroxycyclopentyloxy)acetate (compound 11a)

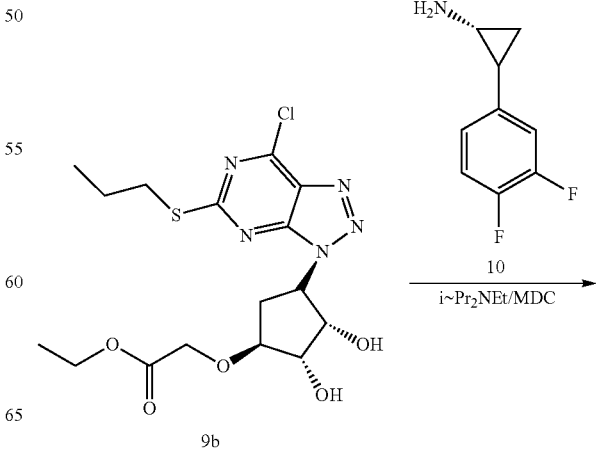

9b

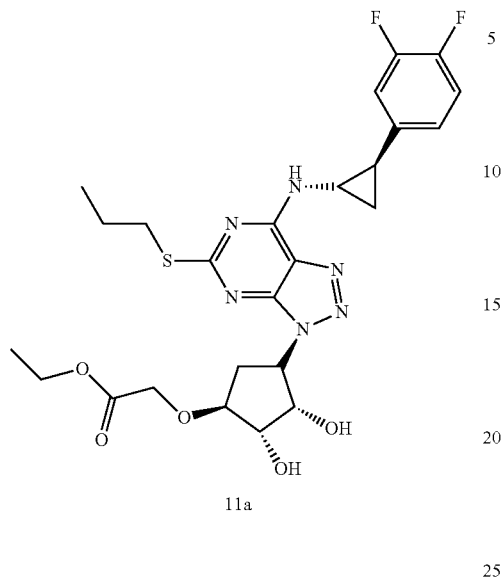

11a

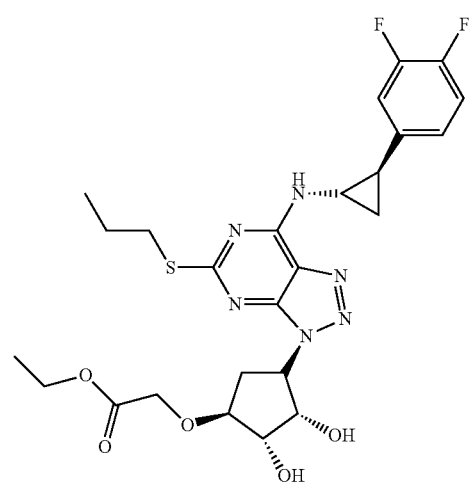

11a

To a solution of compound 10 (3.70 g) in DCM (2-5 vol), was added diisopropylethylamine (3.48 g) at RT. A solution of compound 9b (4 g) in DCM (20 mL) was added. The reaction mixture was stirred at 25° C. for 4-7 h. The reaction was monitored by TLC. After completion of the reaction, the reaction mixture was worked up in DCM and the crude product was isolated and purified by column chromatography eluting with ethyl acetate and n-hexane on silica gel to provide the purified compound (3.5 g, 70%).

Example 25a

Preparation of ethyl 2-((1S,2S,3S,4R)-4-(7-((1R,2S)-2-(3,4-difluoro-phenyl)cyclopropylamino)-5-(propylthio)-3H-[1,2,3]triazolo[4,5-d]pyrimidin-3-yl)-2,3-dihydroxycyclopentyloxy)acetate (compound 11a)

To a solution of compound 10 (3.70 g) in DCM (2 vol), was added diisopropylethylamine (3.48 g) at RT. A solution of compound 9b (4 g) in DCM (20 mL) was added. The reaction mixture was stirred at 25° C. for 4 h. The reaction was monitored by TLC. The reaction did not go to completion.

Example 26

Preparation of methyl 2-((1S,2S,3S,4R)-4-(7-((1R,2S)-2-(3,4-difluoro-phenyl)cyclopropylamino)-5-(propylthio)-3H-[1,2,3]triazolo[4,5-d]pyrimidin-3-yl)-2,3-dihydroxycyclopentyloxy)acetate

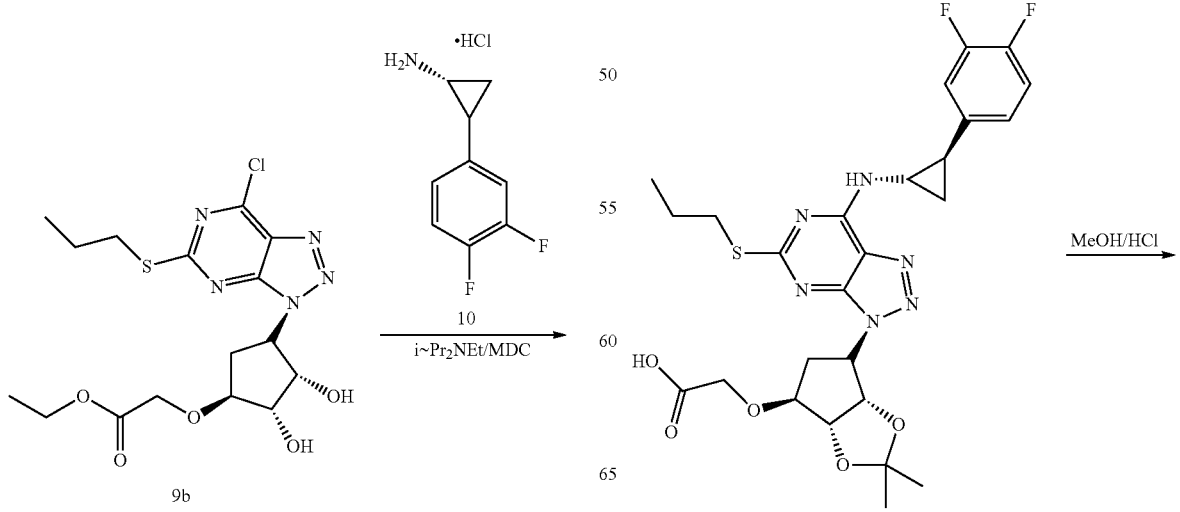

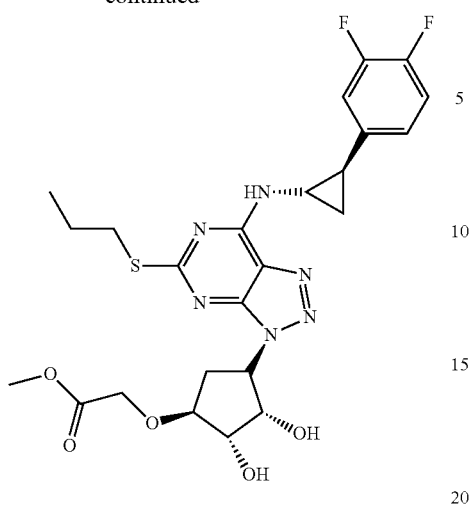

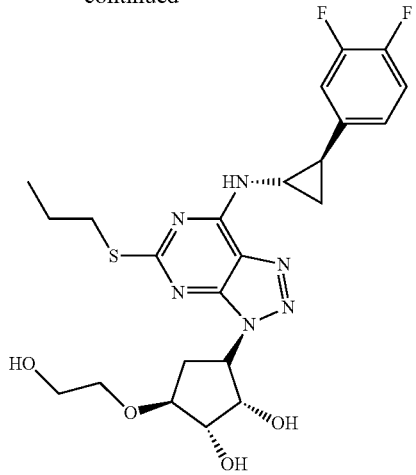

To a suspension of Compound TCG-14 (5 g, 0.0086 mol) acid in methanol (100 ml) was added HCl (1.5 ml) at RT and this mixture was stirred for 16 hr. After the reaction was complete by TLC monitoring 200 ml of water was added, and the mixture was basified with sodium bicarbonate solution and extracted with ethyl acetate (2×200 ml). The extract was dried over anhydrous $Na_2SO_4$, filtered and concentrated under vacuum below 45° C. to provide the crude product. The crude product was crystallized using ethyl acetate and hexane. Isolated Yield was 3.35 g, 70.23%.

Example 27

Preparation of (1S,2S,3R,5S)-3-(7-((1R,2S)-2-(3,4-difluorophenyl)cyclopropylamino)-5-(propylthio)-3H-[1,2,3]triazolo[4,5-d]pyrimidin-3-yl)-5-(2-hydroxy-ethoxy)cyclopentane-1,2-diol

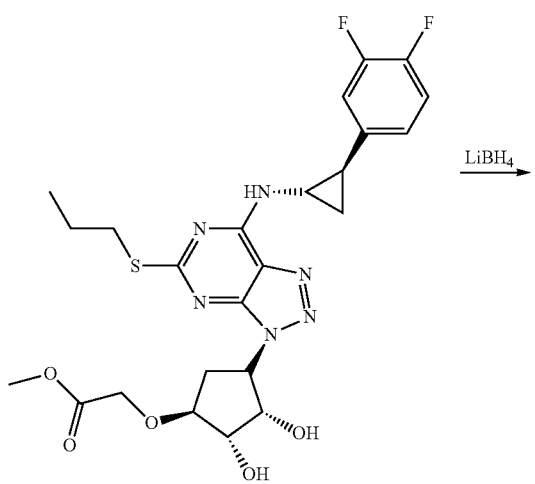

To a solution of TCG-15 DPT (3.5 g, 0.0063 mol) in THF (70 ml) was added LiBH4 (0.415 g, 0.019 mol) at −10° C. The mixture was stirred at RT for one hour. After the reaction was complete by TLC monitoring, 100 ml of water was added and the mixture was acidified with HCl solution and extracted with ethyl acetate (2×100 ml). The extract was dried over anhydrous $Na_2SO_4$, filtered and concentrated under vacuum below 45° C. to provide the crude product. The crude product was crystallized from a mixture of ethyl acetate and hexane to provide 1.80 g (54.5%) of the pure product.

Example-28

Preparation of tert-butyl (3aR,4S,6R,6aS)-4-hydroxytetrahydro-3aH-spiro[cyclopenta[d][1,3]dioxole-2, 1'-cyclopentane]-6-ylcarbamate

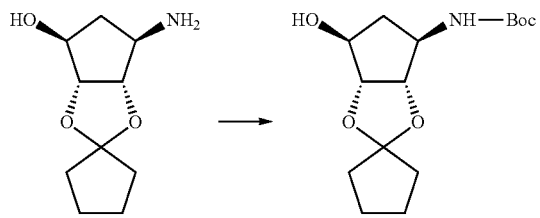

Compound 1 (10 g) is dissolved in THF (2-15V). A solution of water (2-15V) and sodium carbonate (5.85 g) is added. The mixture is stirred at room temperature for 0-15 min followed by dropwise addition of Boc-anhydride (12.04 g). The reaction mixture is then stirred at room temperature for 1-3 hrs. The aqueous and organic layers are separated. The aqueous layer is extracted with EtOAc (1-5V). The combined organic fraction is concentrated and the resulting residue is purified by crystallization to give compound 2 (13.21 g).

Example 29

Preparation of benzyl (3aR,4S,6R,6aS)-4-hydroxytetrahydro-3aH-spiro[cyclopenta[d][1,3]dioxole-2,1'-cyclopentane]-6-ylcarbamate

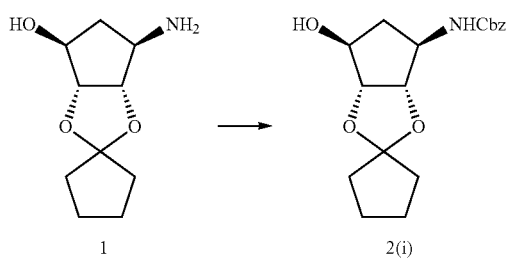 [SMILES: N[C@@H]1C[C@H](O)[C@H]2OC3(CCCC3)O[C@H]21 ; O=C(N[C@@H]1C[C@H](O)[C@H]2OC3(CCCC3)O[C@H]21)OCc1ccccc1]

Compound 1 (10 g) is dissolved in MIBK (180 mL). Water (1-5V mL) and potassium carbonate (8.31 g) are added followed by dropwise addition of benzyl chloroformate (9.42 g). The reaction mixture is stirred at room temperature for 4-6 hours. The aqueous and organic layers are separated. The aqueous layer is extracted with MIBK (80 mL). The combined organic fraction is concentrated and the resulting residue is purified by crystallization in n-hexane give compound 2(i) (15.93 g).

Example 30

Preparation of ethyl 2-((3aS,4R,6S,6aR)-4-(benzyloxycarbonylamino)-tetrahydro-3aH-spiro[cyclopenta[d][1,3]dioxole-2,1'-cyclopentane]-6-yloxy)acetate

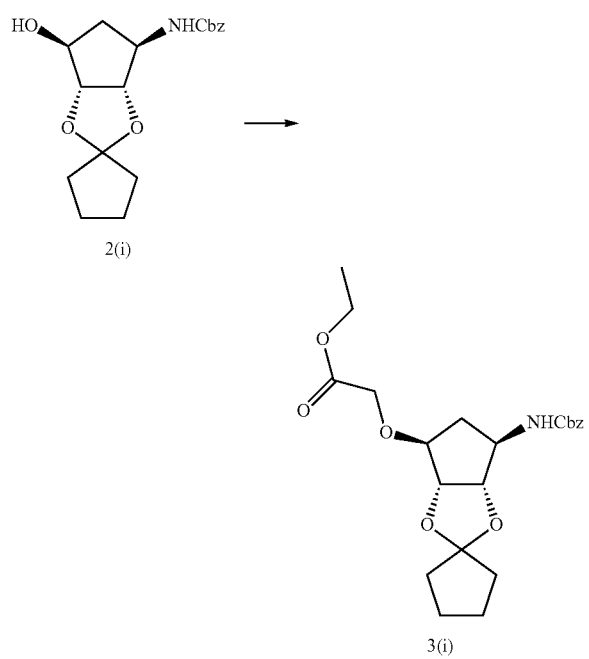

Compound 2(i) (10 g) is dissolved in THF (15-25V), and the solution is cooled to 0 to −50° C. Potassium-tert-butoxide (4.04 g) is added at 0 to −50° C. After 10-30 min, ethylbromoacetate (6.01 g) in THF (40 mL) is added dropwise. The reaction mixture is stirred at 0 to −50° C. for 8-10 hrs. The reaction progress is monitored by TLC. When complete, the reaction is quenched by addition of water (60 mL) and then is concentrated to produce a residue. The residue is taken up in water (150 mL) and extracted with ethyl acetate. The extract is concentrated to provide compound 3(i) (14.31 g), which will be used for the next step without further purification.

Example 31

Preparation of ethyl 2-((3aS,4R,6S,6aR)-4-(tert-butoxycarbonylamino)tetrahydro-3aH-spiro[cyclopenta[d][1,3]dioxole-2,1'-cyclopentane]-6-yloxy)acetate

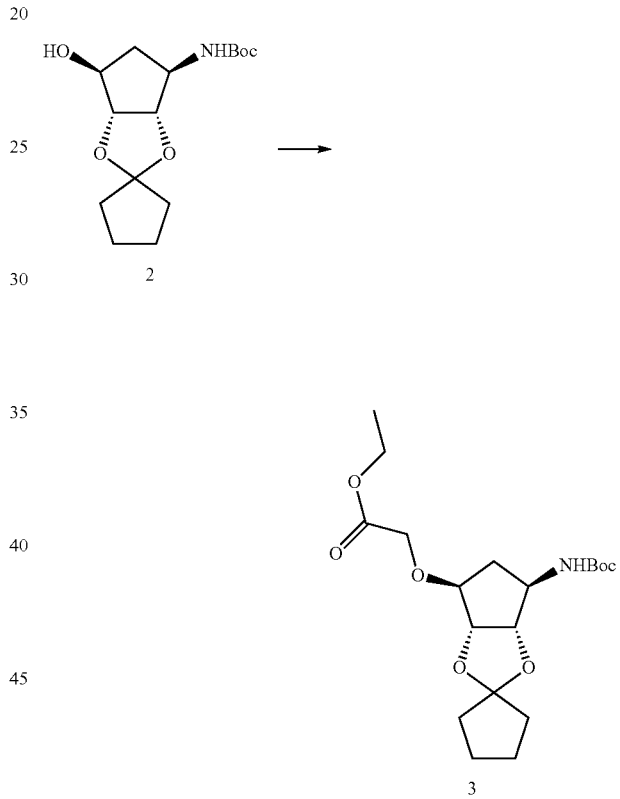

Compound 2 (10 g) is dissolved in THF (15-25V) and cooled to 0 to −50° C. Potassium-tert-butoxide (4.49 g) is added at 0 to −50° C. After 10-30 min. a pre-made solution of ethylbromoacetate (6.69 g) in THF (40 mL) is added dropwise. The resulting reaction mixture is stirred at 0 to −50° C. for 8-10 hours. When the reaction is complete, it is quenched by addition of water (60 mL) and concentrated to produce a residue. The residue is diluted with water (150 mL) and extracted with ethyl acetate. The extracts are concentrated to produce a residue which is purified by crystallization from n-hexane to give compound 3 (7.19 g).

Example 32

Preparation of benzyl (3aR,4S,6R,6aS)-4-(2-hydroxyethoxy)tetrahydro-3aH-spiro[cyclopenta[d][1,3]dioxole-2,1'-cyclopentane]-6-ylcarbamate

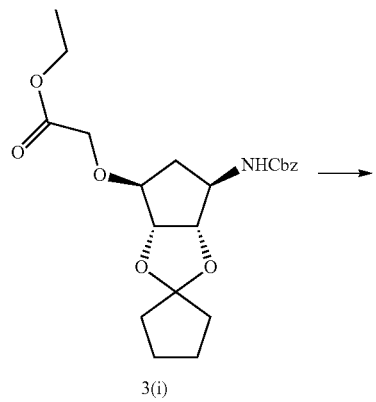

3(i)

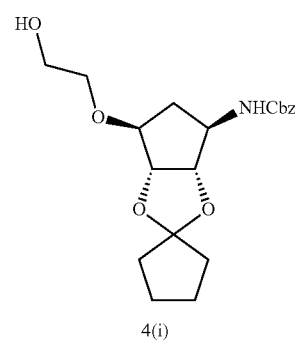

4(i)

Compound 3(i) (10 g) is dissolved in THF (5-10V). Lithium borohydride (1.81 g) is added portion wise at 25-30° C. The reaction mixture is stirred at room temperature for 8-12 hours. The reaction is quenched with acetic acid and then with water. Ethyl acetate (150 ml) is added and the aqueous and organic layers are separated. The aqueous layer is adjusted to neutral pH with saturated aqueous NaHCO₃ solution and then extracted with ethyl acetate (80 mL). The combined organic fraction is concentrated to provide compound 4(i) (7.48 g), which is used for the next step without further purification.

Example 33

Preparation of tert-butyl (3aR,4S,6R,6aS)-4-(2-hydroxyethoxy)tetrahydro-3aH-spiro[cyclopenta[d][1,3]dioxole-2,1'-cyclopentane]-6-ylcarbamate

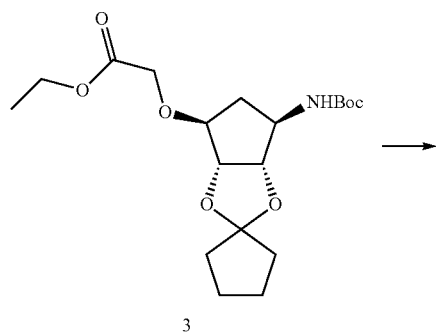

3

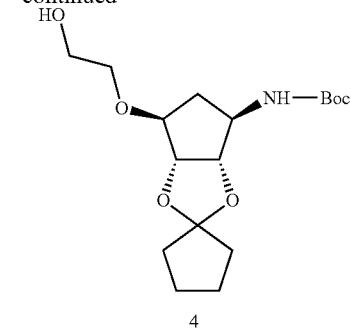

4

Compound 3 (10 g) is dissolved in THF (5-10V). Lithium borohydride (1.97 g) is added portion wise at 25-30° C. The reaction mixture is stirred at room temperature for 8-12 hours. The reaction is quenched with acetic acid and then with water. Ethyl acetate (150 mL) is added and the aqueous and organic layers are separated. The aqueous fraction is neutralized with sat. NaHCO₃ solution and then extracted with ethyl acetate (80 mL). The combined organic layers are concentrated to provide compound 4 (7.63 g), which is used for the next step without further purification.

Example 34

Preparation of 2-((3aS,4R,6S,6aR)-4-aminotetrahydro-3aH-spiro[cyclopenta[d][1,3]dioxole-2,1'-cyclopentane]-6-yloxy)ethanol

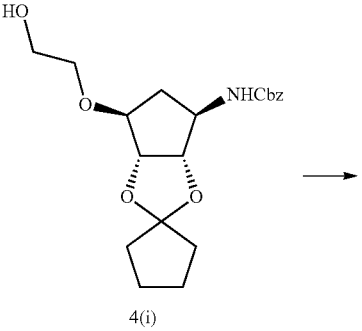

4(i)

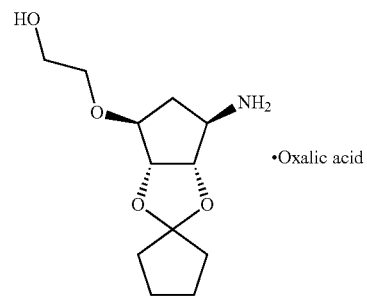

5

Compound 4(i) (10 g) is dissolved in ethanol (5-10V) Ammonium formate (1.68 g) and 10% Pd/C are added. The reaction mixture is heated to 30-70° C. for 1-3 hours. The reaction mixture is filtered. The filtrate and oxalic acid (3.34 g) are charged into a 1 L RB flask. The resulting reaction mixture is heated to 50-70° C. for 1-4 hours. The reaction mixture is stirred at RT for 8-10 hrs. The ethanol is distilled off and the resulting residue is suspended in hexane. The suspension is filtered and the collected solid is dried to give compound 5 (7.51 g).

Example 35

Preparation of 2-((3aS,4R,6S,6aR)-4-aminotetrahydro-3aH-spiro[cyclopenta[d][1,3]dioxole-2,1'-cyclopentane]-6-yloxy)ethanol

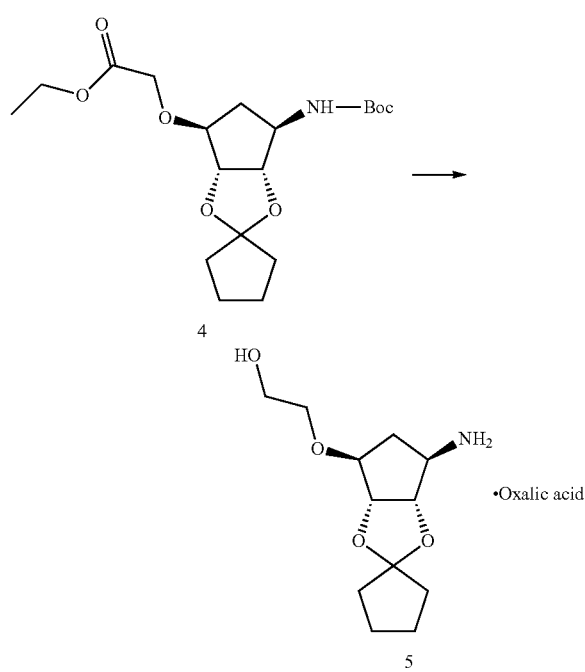

Compound 4 (10 g) is dissolved in ethanol (10-20V). Ceric ammonium nitrate (15.96 g) is added. The resulting reaction mixture is heated to 30-70° C. for 10-12 hrs. The reaction mixture is quenched and extracted with DCM. The DCM layer is distilled off. The thus obtained residue is suspended in ethanol (2-101) followed by addition of oxalic acid (3.68 g). The resulting mixture is heated to 30-70° C. for 1-4 hours and at room temperature for 8-10 hours. The ethanol layer is distilled off and residue is purified and filtered to give compound 5 (5.43 g).

Example 36

Preparation of 2-((3aS,4R,6S,6aR)-4-(5-amino-6-chloro-2-(propylthio)-pyrimidin-4-ylamino)tetrahydro-3aH-spiro[cyclopenta[d][1,3]dioxole-2,1'-cyclopentane]-6-yloxy)ethanol

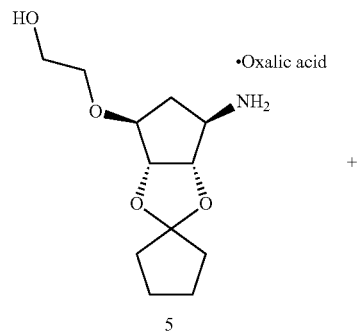

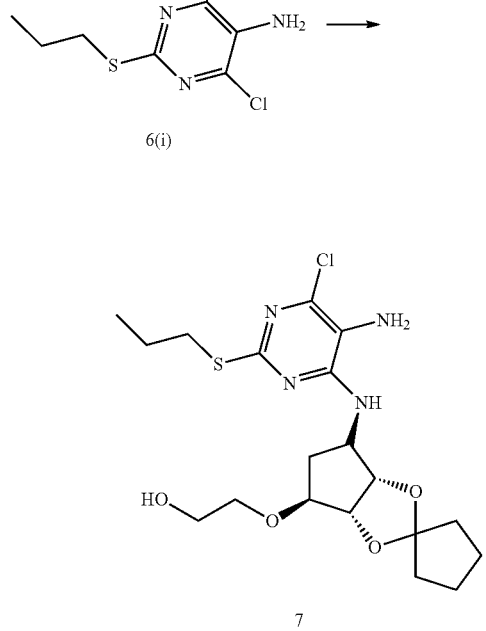

Compound 5 (10.0 g) and compound 6(I) (10.0 g) are condensed in NMP (50 mL) in the presence of triethylamine (12.56 g). The reaction mixture is flushed with nitrogen and heated to 30-90° C. The reaction mixture is stirred for 6-12 hrs at same temperature. The obtained residue is diluted with water (150 mL). The aqueous layer is extracted with ethyl acetate. The organic layer is concentrated and 1-2 vol ethyl acetate kept inside. The reduced-volume mixture is heated to 30-70° C., and 5-10 V heptane is charged dropwise. The resulting mixture is cooled to 0° C. and stirred for 1-3 hrs and filtered to provide compound 7 (8.31 g).

Example 37

Preparation of 2-((3aS,4R,6S,6aR)-4-(7-chloro-5-(propylthio)-3H-[1,2,3]triazole[4,5-d]pyrimidin-3-yl)tetrahydro-3aH-spiro[cyclopenta[d][1,3]dioxole-2,1'-cyclopentane]-6-yloxy)ethanol

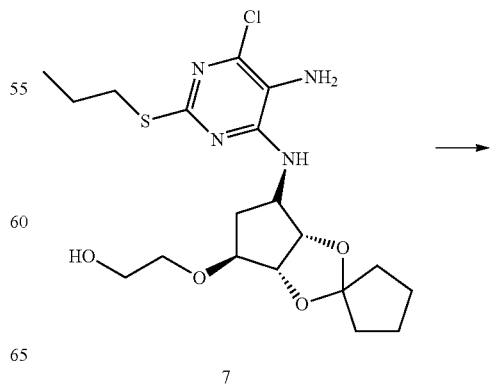

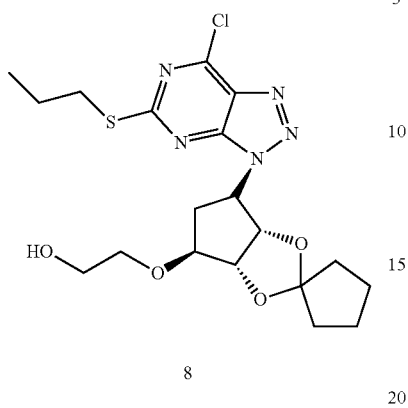

8

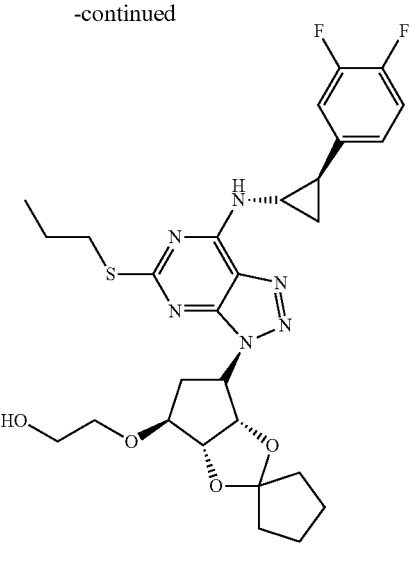

10

To a mixture of compound 7 (10.0 g), toluene (5-10V) and acetic acid (5-10V), is added sodium nitrite (1.74 g) in water (1-5V). The reaction mixture is stirred for 1-5 hrs at 25-30° C. Potassium carbonate (9.32 g) in water is added to the reaction mixture and it is stirred for 10-30 min., extracted and the organic layer was concentrated to provide crude compound 8, which is used for the next step.

Example 38

Preparation of 2-((3aS,4R,6S,6aR)-4-(7-((1R,2S)-2-(3,4-difluorophenyl)-cyclopropylamino)-5-(propylthio)-3H-[1,2,3]triazolo[4,5-d]pyrimidin-3-yl)tetrahydro-3aH-spiro[cyclopenta[d][1,3]dioxole-2,1'-cyclopentane]-6-yloxy)ethanol To a solution of compound 8 in toluene, is added compound 9 (8.78 g) and potassium carbonate (45.96 g) in water (2-10V). The reaction mixture is stirred at 25-30° C. for 2-8 hrs and the aqueous and organic layers are separated. The organic layer is washed with acetic acid (5.32 g) and sodium chloride (5.32 g) in 45 ml of water and washed a second time with acetic acid (1.78 g) and sodium chloride (1.22 g) in 53 ml water, and washed a third time with sodium chloride (5.3 g) in 48 ml water. The organic layer is then concentrated to provide crude compound 10, which is used for the next step.

Example 39

Preparation of (1S,2S,3R,5S)-3-(7-((1R,2S)-2-(3,4-difluorophenyl)-cyclopropylamino)-5-(propylthio)-3H-[1,2,3]triazolo[4,5-d]pyrimidin-3-yl)-5-(2-hydroxyethoxy)cyclopentane-1,2-diol

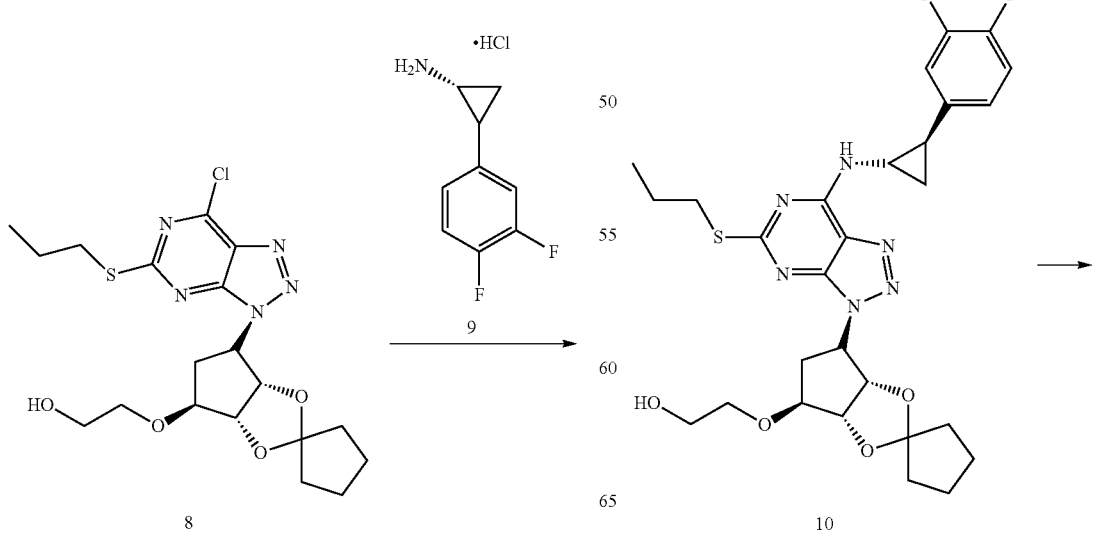

97

-continued

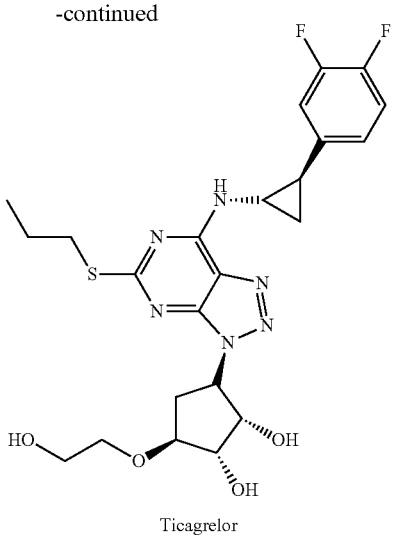

Ticagrelor

Compound 10 in toluene is cooled to 0-20° C., and Conc. HCl (26.24 g) and methanol (2-10V) are added at 0-20° C. The reaction mixture is stirred at 0-20° C. for 8-20 hrs. The reaction is monitored by TLC. After completion, the methanol is distilled off under reduced pressure. The obtained residue is diluted with water and the mixture is neutralized with saturated aqueous NaHCO$_3$ and extracted with ethyl acetate (2×150 mL). The organic fraction is washed with aqueous sodium bicarbonate (50 mL) and concentrated to provide the crude product, which is crystallized from a mixture of ethyl acetate and heptane to provide a white solid (8.23 g).

Example 40

Preparation of 4,6-dichloro-2-(propylthio)pyrimidin-5-amine

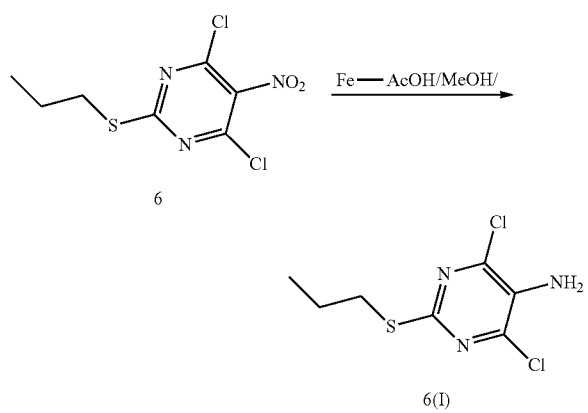

Iron powder (15.62 g) was added to a solution of compound 6 in methanol (10 vol) and acetic acid (5.0 vol) at <30° C., and the resulting reaction mixture was stirred for 3-5 hrs at 50° C. The reaction was monitored by TLC. The reaction mixture was worked up by adding water (5.0 vol) and filtering. The filtrate was concentrated under reduced pressure at 40-50° C. to produce a residue. The residue was extracted with ethyl acetate (500-600 ml) and the combined ethyl acetate fraction was washed with aqueous sodium bicarbonate and concen-

98 trated under reduced pressure. The thus obtained residue was crystallized from n-hexane. Isolated yield 90-95%.

$^1$H NMR (400 MHz, CDCl$_3$): δ 4.22 (brs, 2H), 3.07 (t, J=8 Hz, 2H), 1.77-1.68 (m, 2H), 1.03 (t, J=8 Hz, 3H). $^{13}$C NMR (100 MHz, CDCl$_3$) δ 158.60, 145.27, 131.48, 33.38, 22.42, 13.45.

Example 41

Preparation of benzyl (1R,2S,3S,4S)-2,3-dihydroxy-4-(2-hydroxyethoxy)-cyclopentylcarbamate

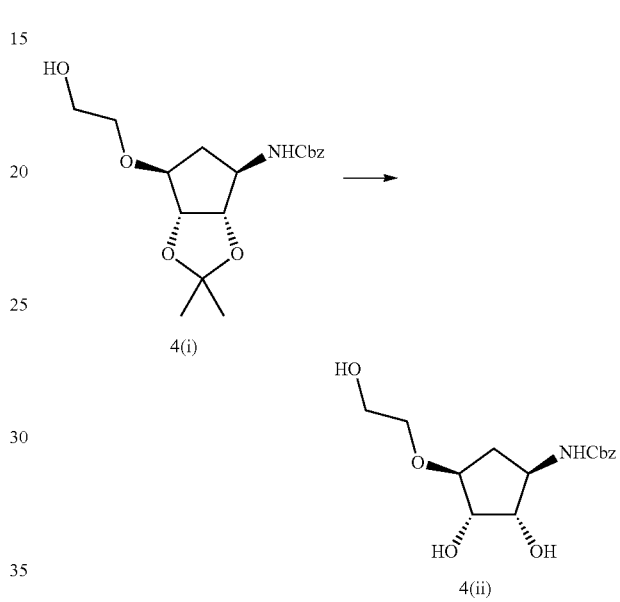

Compound 4(i) (20.0 g) was dissolved in Methanol (2-10V). Conc. HCl (18.69 g) and water (2-8V) were added at 25-30° C. The reaction mixture was stirred for 8-20 hrs. The reaction was monitored by TLC. After completion, the methanol was distilled off under reduced pressure. The obtained residue was diluted with water and the mixture was neutralized with saturated aqueous NaHCO$_3$ and extracted with ethyl acetate (2×200 mL). The organic layer was washed with aqueous sodium bicarbonate (120 mL) and concentrated to provide the product as a crude residue which was purified by crystallization give compound 4(ii) (2.83 g).

Example 41a

Preparation of benzyl (1R,2S,3S,4S)-2,3-dihydroxy-4-(2-hydroxyethoxy)-cyclopentylcarbamate Compound 4(i) (20.0 g) was dissolved in Methanol (5V). Conc. HCl (18.69 g) and water (5V) were added at 25-30° C. The reaction mixture was stirred for 18 hrs. The reaction was monitored by TLC. After completion, the methanol was distilled off under reduced pressure. The obtained residue was diluted with water and the mixture was neutralized with saturated aqueous NaHCO$_3$ and extracted with ethyl acetate (2×200 mL). The organic layer was washed with aqueous sodium bicarbonate (120 mL) and concentrated to provide the product as a crude residue which was purified by crystallization from MTBE to give compound 4(ii) (2.83 g).

Example 42

Preparation of benzyl (3aR,4S,6R,6aS)-4-(2-hydroxyethoxy)tetrahydro-3aH-spiro[cyclopenta[d][1,3]dioxole-2,1'-cyclopentane]-6-ylcarbamate

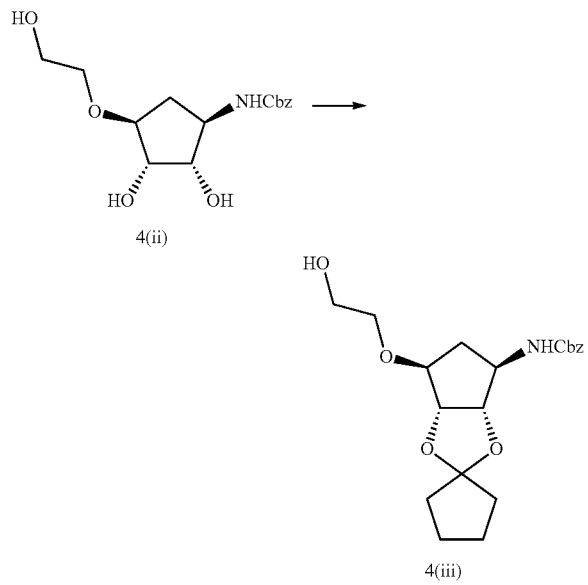

Compound 4(ii) (2.7 g) was dissolved in cyclopentanone (5-20V). PTSA (0.16 g) was added. The reaction mixture was stirred for 8-10 hrs. The reaction progress was monitored by TLC. Water was added (60 mL), and the mixture was extracted with ethyl acetate. The organic layer was concentrated to provide compound 4(iii) (3.14 g).

Example 42a

Preparation of benzyl (3aR,4S,6R,6aS)-4-(2-hydroxyethoxy)tetrahydro-3aH-spiro[cyclopenta[d][1,3]dioxole-2,1'-cyclopentane]-6-ylcarbamate Compound 4(ii) (2.7 g) was dissolved in cyclopentanone (7.4V). PTSA (0.16 g) was added. The reaction mixture was stirred for 8-10 hrs. The reaction progress was monitored by TLC. Water was added (60 mL), and the mixture was extracted with ethyl acetate. The organic layer was concentrated to provide compound 4(iii) (3.14 g).

Example 43

Preparation of ethyl 2-((1S,2S,3S,4R)-4-(5-amino-6-chloro-2-(propylthio)-pyrimidin-4-ylamino)-2,3-dihydroxycyclopentyloxy)acetate

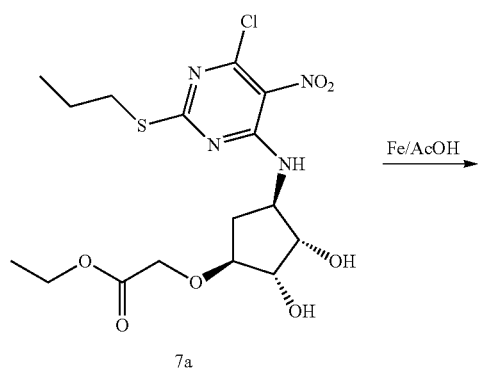

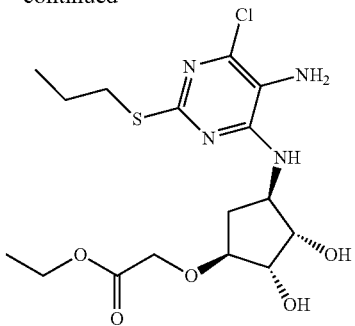

Compound 7a (5 g, 0.011 mol) was added to methanol (25 mL) at 25-30° C. Acetic acid (15 mL) was added slowly to the reaction mixture over 30 min. The reaction mixture was stirred at 25-30° C. for 2 h. After 2 hrs, the reaction was monitored by TLC and showed completion. The reaction mixture was passed through a diatomaceous earth (Celite) pad and the pad was washed with methanol (25 mL). The filtrate was concentrated under reduced pressure at 50° C. The thus obtained residue was mixed with water (50 mL) and basified with aqueous $NaHCO_3$ to pH 9.0. The aqueous layer was extracted with ethyl acetate (3×25 mL). The combined extract was washed with brine, dried over anhydrous $Na_2SO_4$, and concentrated under reduced pressure to provide the crude product (89%), which was used for next step without further purification.

Example 44

Preparation of tert-butyl(3aR,4S,6R,6aS)-tetrahydro-4-hydroxy-2,2-dimethyl-3aH-cyclopenta[d][1,3]dioxol-6-ylcarbamate

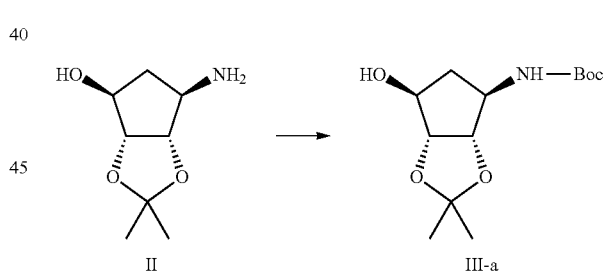

Compound II (100 g, 0.578 mol) was dissolved in THF (1500 mL). Water (1500 mL) and sodium carbonate (67.4 g, 0.635 mol) were added at 25-30° C. The reaction mixture was stirred at the same temperature for next 10-15 min. Then Boc-anhydride was added slowly over 1 h at 25-30° C. The reaction mixture was stirred at 25-30° C. for 1 h. The reaction progress was monitored by TLC. When the reaction was complete, the aqueous and organic layers were separated, and the organic layer was washed with brine (500 mL) and water (500 mL) and the combined aqueous layer was extracted with EtOAc (500 mL). The combined organic layer was dried over anhydrous $Na_2SO_4$, and then concentrated under reduced pressure at 35-40° C. The thus obtained residue was mixed with n-hexane (1500 mL) and stirred at 25-30° C. for 1 h. Compound III-a precipitated and was isolated by filtration and washed with n-hexane (100 mL). The isolated compound III-a was dried under vacuum at 40° C. over 12 h.

$^1$H NMR (400 MHz, CDCl$_3$): δ 5.44 (d, J=8 Hz, 1H), 4.57-4.49 (m, 2H), 4.27 (t, J=4 Hz, 1H), 4.09 (brs, 1H), 2.55 (brs, 1H), 2.22 (brs, 1H), 1.68 (d, J=16 Hz, 1H), 1.45 (s, 9H), 1.41 (s, 3H), 1.26 (s, 3H). $^{13}$C NMR (100 MHz, CDCl$_3$) δ 155.20, 110.17, 86.23, 35.47, 28.44, 26.23, 23.85.

Example 45

Preparation of benzyl (3aR,4S,6R,6aS)-tetrahydro-4-hydroxy-2,2-dimethyl-3aH-cyclopenta[d][1,3]dioxol-6-ylcarbamate

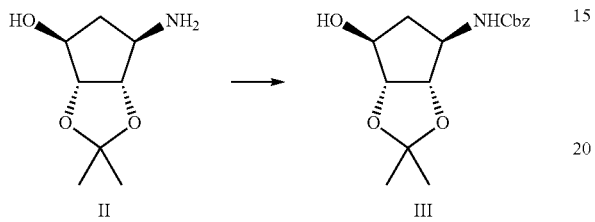

Compound II (50 g, 0.288 mol) was dissolved in MIBK (900 mL). Water (250 mL) and potassium carbonate (47.80 g, 0.346 mol) were added at 25-30° C. The reaction mixture was stirred at the same temperature for 30-min, and then added solution of benzyl chloroformate 50% in Toluene (54.16 g, 0.317 mol) was added slowly over 30 min at 25-30° C. The reaction mixture was stirred at 25-30° C. for 6 h. Reaction progress was monitored by TLC. When the reaction was complete, the aqueous and organic layers were separated, and the aqueous layer was extracted with MIBK (250 mL). The combined organic fraction was dried over anhydrous Na$_2$SO$_4$ and concentrated under reduced pressure at 40-50° C. to provide a residue. The residue was mixed with n-hexane (500 mL) and stirred at 25-30° C. for 1 h. A precipitate formed and the solid was isolated by filtration and washed with n-hexane (100 mL). The collected compound 3(I) was dried under vacuum at 40° C. over 12 h, isolated.

$^1$H NMR (400 MHz, CDCl$_3$): δ 7.37-7.30 (m, 5H), 5.68 (brs, 1H), 5.11 (s, 2H), 4.60 (d, J=4 Hz, 1H), 4.49 (dd, J=8 Hz, J=4 Hz, 1H), 4.28 (brs, 1H), 4.20 (t, J=8 Hz, 1H), 2.28-2.06 (m, 2H), 1.73-1.69 (m, 2H), 1.42 (s, 3H), 1.29 (s, 3H). $^{13}$C NMR (100 MHz, CDCl$_3$) δ 155.58, 136.51, 128.53, 128.15, 110.30, 86.16, 86.05, 77.59, 66.74, 57.03, 35.33, 26.18, 23.80.

Example 46

Preparation of ethyl 2-(((3aR,4S,6R,6aS)-6-(((benzyloxy)carbonyl)amino)-2,2-dimethyltetrahydro-3aH-cyclopenta[d][1,3]dioxol-4-yl)oxy)acetate

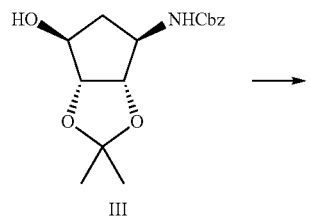

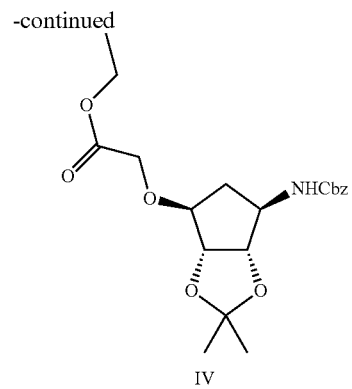

Compound III (70 g, 0.288 mol) was dissolved in THF (1400 mL) at 25-30° C. The reaction mixture was cooled to −30 to −20° C. Potassium-tert-butoxide (30.66 g) was added in one lot. The reaction mixture was stirred at the same temperature for 1 h. Then a pre-made solution of ethylbromoacetate (45.64 g) in THF (170 mL) was added slowly to the reaction mixture over 2 h at −30 to −20° C. The reaction mixture was stirred at the same temperature for 2 h. Reaction progress was monitored by TLC. A second portion of ethylbromoacetate (30.43 g) in THF (110 mL) was added at −30 to −20° C. to the reaction mixture over 1.5 h. The reaction mixture was stirred at −20° C. for 16 h. Water (210 mL) was added to the reaction mixture and the THF was distilled off under reduced pressure at 50° C. The thus obtained residue was diluted with water (150 mL). The aqueous layer was extracted with ethyl acetate (3×200 mL). The combined organic layer was washed with brine (250 mL) and dried over anhydrous Na$_2$SO$_4$, and concentrated under reduced pressure at 40-50° C. to provide crude compound IV (105 g), which was used, for next step without further purification.

$^1$H NMR (400 MHz, CDCl$_3$): δ 7.37-7.28 (m, 5H), 5.96 (d, J=8 Hz, 1H), 5.10 (s, 2H), 4.57 (s, 2H), 4.22-3.90 (m, 6H), 3.91 (d, J=4 Hz, 1H), 2.24-2.18 (m, 1H), 1.82 (d, J=12 Hz, 1H), 1.40 (s, 3H), 1.26 (s, 3H), 1.23 (t, J=8 Hz, 3H).). $^{13}$C NMR (100 MHz, CDCl$_3$) δ 170.27, 155.68, 136.71, 128.45, 128.16, 128.00, 110.42, 86.28, 86.07, 85.69, 83.03, 66.95, 66.54, 61.31, 57.37, 56.67, 33.22, 31.94, 29.71, 26.16, 23.79, 14.12.

Example 47

Preparation of tert-butyl (3aR,4S,6R,6aS)-4-((ethoxycarbonyl)methoxy)-tetrahydro-2,2-dimethyl-3aH-cyclopenta[d][1,3]dioxol-6-ylcarbamate

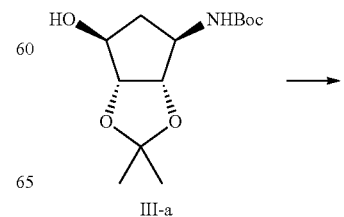

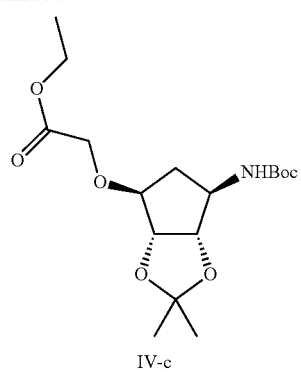

IV-c

Compound III (50 g) was dissolved in THF (1000 mL) at 25-30° C. The reaction mixture was cooled to −30 to −20° C. Potassium-tert-butoxide (30.80 g) was added in one lot. The reaction mixture was stirred at the same temperature for 1 h. Then, a pre-made solution of ethylbromoacetate (45.88 g) in TUT (200 mL) was added slowly to the reaction mixture over 1 hr at −30 to −20° C. The mixture was stirred at the same temperature for 1 h. Reaction progress was monitored by TLC and it showed the presence of starting material. Water (20 mL) was added to the reaction mixture and the mixture was warmed to 25-30° C. The THF layer was distilled off under reduced pressure at 40° C. The thus obtained residue was diluted with water (500 mL), and this mixture was extracted with ethyl acetate (2×300 mL). The combined organic layer was washed with brine (250 mL), dried over anhydrous $Na_2SO_4$, and concentrated under reduced pressure at 30-40° C. The thus isolated compound IV-c, was crystallized from n hexane to give 40 g as a white to off white solid.

$^1$H NMR (400 MHz, $CDCl_3$): δ 5.56 (d, J=8 Hz, 1H), 4.59-4.57 (m, 2H), 4.25 (q, J=8 Hz, 2H), 4.18-4.08 (m, 2H), 3.91 (d, J=4 Hz, 1H), 2.25-2.18 (m, 1H), 1.80 (d, J=16 Hz, 1H), 1.74 (brs, 1H), 1.45 (s, 9H), 1.40 (s, 3H), 1.32 (t, J=8 Hz, 3H), 1.22 (s, 3H). $^{13}$C NMR (100 MHz, $CDCl_3$) δ 1.70.19, 155.16, 110.38, 86.34, 85.89, 83.10, 79.20, 66.98, 61.24, 56.23, 33.34, 31.94, 29.71, 29.38, 28.44, 26.20, 23.84, 22.71, 14.21, 14.14.

Example 48

Preparation of 2-(((3aR,4S,6R,6aS)-6-(((benzyloxy)carbonyl)amino)-2,2-dimethyl tetrahydro-3aH-cyclopenta[d][1,3]dioxol-4-yl)oxy)acetic acid (IV-a), via ethyl 2-(((3aR,4S,6R,6aS)-6-(((benzyloxy)carbonyl)amino)-2,2-dimethyltetrahydro-3a H-cyclopenta[d][1,3]dioxol-4-yl)oxy)acetate (IV)

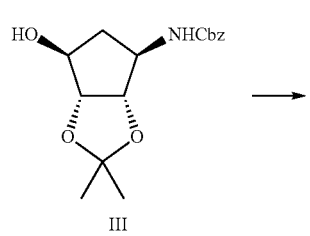

III

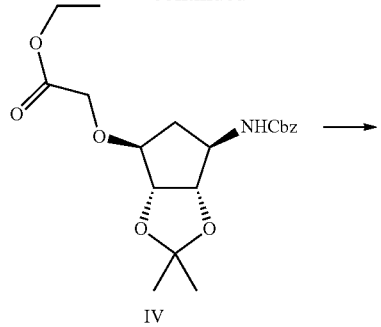

A suspension of sodium hydride 60% (3.9 g) in DMF (2-10V) is cooled to −50 to 0° C. Compound III (20 g,) is dissolved in DMF (2-10V) and added to the reaction flask over 10 to 30 min. The reaction mixture is stirred at the same temperature for 10 to 30 min. A solution of ethylbromoacetate (13.04 g) in DMF (80 mL) is added dropwise. The reaction mixture is stirred at the same temperature for 1-2 hrs. The reaction progress is monitored by TLC. When the reaction is complete, the reaction is quenched by addition of acetic acid and water (600 mL). The aqueous layer is extracted with ethyl acetate (400 mL). The organic layer is concentrated to dryness. The obtained residue is dissolved in THF (60 mL) and charged into a reaction flask. The reaction flask is cooled to below 10° C. and a solution of NaOH (7.8 g) in water (30 mL) is added. The reaction mixture is stirred at RT for 2-6 hrs. The THF layer is distilled off and the aqueous layer is washed with ethyl acetate (80 mL). The aqueous layer is acidified to pH 2-3 and extracted with ethyl acetate (3×100 mL). The combined organic layer is dried over anhydrous sodium sulphate and concentrated to dryness to give compound IV-a.

Example 48a

Preparation of 2-(((3aR,4S,6R,6aS)-6-(((benzyloxy)carbonyl)amino)-2,2-dimethyl tetrahydro-3aH-cyclopenta[d][1,3]dioxol-4-yl)oxy)acetic acid (IV-a), via ethyl 2-(((3aR,4S,6R,6aS)-6-(((benzyloxy)carbonyl)amino)-2,2-dimethyltetrahydro-3a H-cyclopenta[d][1,3]dioxol-4-yl)oxy)acetate (IV)

Compound III (20 g) and DMF (2.5V) were added to the reaction flask. A suspension of sodium hydride (3.38 g) 60% in mineral oil was added under nitrogen at −25°. The resulting reaction mixture was stirred at −25° for 2 hr. A solution of ethylbromoacetate (14.12 g) in DMF (10 mL) was then added dropwise. The resulting reaction mixture was stirred at −25° for 1-2 hrs. The reaction progress was monitored by TLC. When the reaction was complete, the reaction was quenched by addition of acetic acid and a solution of NaOH (2.6 g) in water (20 mL). The resulting mixture was stirred for 16 hrs at 25-30° C. Water (150 ML) was added to the reaction mixture.

The aqueous layer was acidified to pH 2-3 and extracted with ethyl acetate (2×300 mL). The combined organic layer was dried over anhydrous sodium sulphate and concentrated to dryness to give compound IV-a 19.45 g $^1$H NMR (400 MHz, DMSO-d$_6$): δ 7.36-7.27 (m, 5H), 7.00 (d, J=8 Hz, 1H), 4.96 (s, 2H), 4.49-4.48 (m, 1H), 4.39-4.38 (m, 1H), 4.13-3.99 (m, 4H), 2.11-2.04 (m, 1H), 1.73-1.69 (m, 2H), 1.31 (s, 3H), 1.17 (s, 3H). $^{13}$C NMR (100 MHz, CDCl$_3$) δ 172.79, 155.82, 137.36, 128.88, 128.34, 128.19, 110.77, 85.05, 84.78, 83.49, 66.63, 65.90, 56.42, 39.00, 33.70, 26.73, 24.43, 21.47.

Example 49

Preparation of 2-(((3aR,4S,6R,6aS)-6-(((benzyloxy)carbonyl)amino)-2,2-dimethyltetrahydro-3aH-cyclopenta[d][1,3]dioxol-4-yl)oxy)acetic acid (IV-a)-via ethyl 2-(((3aR,4S,6R,6aS)-6-(((benzyloxy)carbonyl)amino)-2,2-dimethyltetrahydro-3a H-cyclopenta[d][1,3]dioxol-4-yl)oxy)acetate (IV)

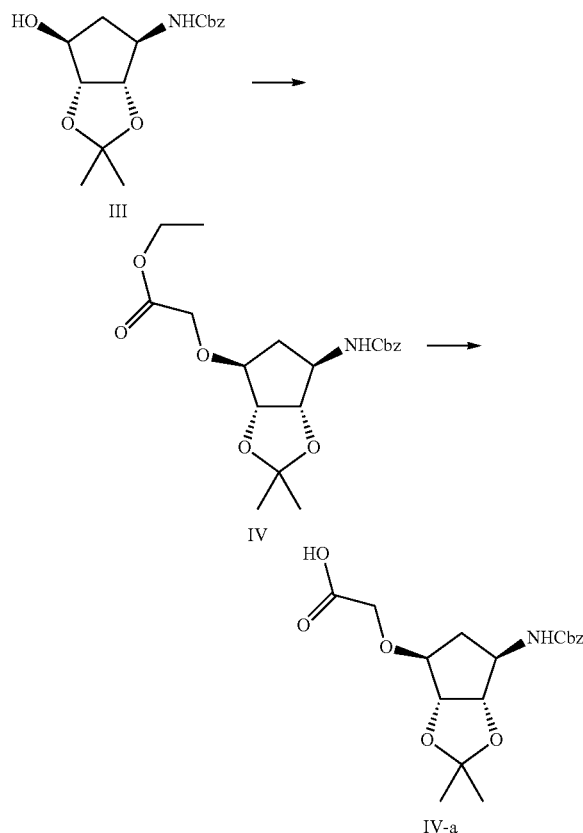

Compound III (70 g) was dissolved in THF (10-20V). Potassium-tert-butoxide (30.66 g) was added. After 10-30 min, ethyl bromoacetate (45.64 g) in THF (170 mL) was added dropwise over 1 h. The reaction mixture was stirred at −40 to 0° C. for 8-10 hrs. A solution of NaOH (7.8 g) in water (30 mL) was added and the reaction mixture was stirred at RT for 2-6 hrs. The THF layer was distilled off and the aqueous layer was washed with ethyl acetate (80 mL). The aqueous layer was acidified to pH 2-3 and extracted with ethyl acetate (3×100 mL). The combined organic fraction was dried over anhydrous sodium sulphate and concentrated to dryness to give compound IV-a.

Example 49a

Preparation of 2-(((3aR,4S,6R,6aS)-6-(((benzyloxy)carbonyl)amino)-2,2-dimethyltetrahydro-3aH-cyclopenta[d][1,3]dioxol-4-yl)oxy)acetic acid (IV-a)-via ethyl 2-(((3aR,4S,6R,6aS)-6-(((benzyloxy)carbonyl)amino)-2,2-dimethyltetrahydro-3aH-cyclopenta[d][1,3]dioxol-4-yl)oxy)acetate (IV)

Compound III (50 g) was dissolved in THF (10V). Potassium-tert-butoxide (21.90 g) was added at −25 to −20° C. After 30 min, ethyl bromoacetate (32.60 g) in THF (100 mL) was added dropwise over 1 h. The reaction mixture was stirred at −25° C. for 8-10 hrs, and then warmed to 25-30° C. A solution of NaOH (19.52 g) in water (100 mL) was added and the reaction mixture was stirred at RT for 2 hrs. The THF layer was distilled off and water (500 mL) was added. The aqueous layer was washed with ethyl acetate (2×300 mL). The aqueous layer was acidified to pH 2-3 and extracted with ethyl acetate (2×500 mL). The combined organic fraction was dried over anhydrous sodium sulphate and concentrated to dryness to give compound IV-a (60 g).

Example 50

Preparation of 2-((3aS,4R,6S,6aR)-4-amino-tetrahydro-2,2-dimethyl-3aH-cyclopenta[d][1,3]dioxol-6-yloxy)acetic acid

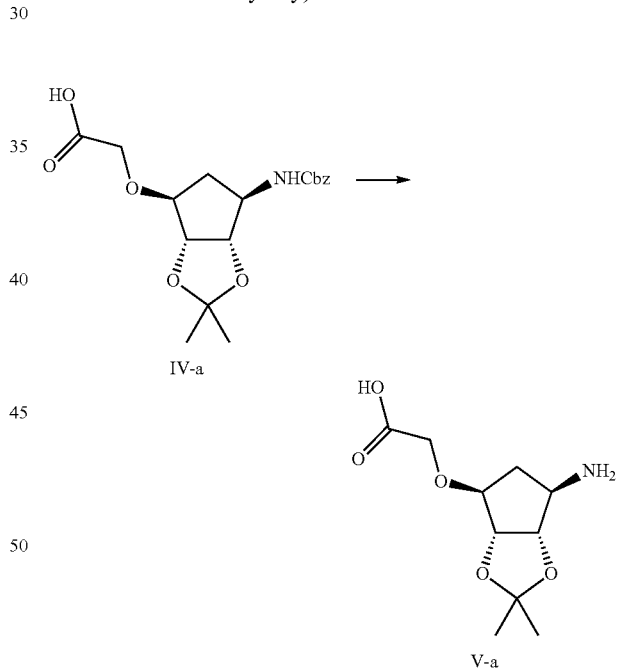

Compound IV-a (10 g) was dissolved in ethanol (5-10V). Ammonium formate (1.72 g) and 10% Pd/C (1.0 g) were added. The reaction mixture was heated to 30-70° C. for 3-7 hours. The reaction mixture was filtered and the filtrate was concentrated to dryness at 40° C. to give compound V-a (6.0 g).

$^1$H NMR (400 MHz, D$_2$O): δ 4.96 (s, 2H), 4.04 (d, J=4 Hz, 1H), 3.97-3.88 (m, 2H), 3.64 (d, J=8 Hz, 1H), 2.31-2.25 (m, 1H), 2.04-2.00 (m, 1H), 1.85 (brs, 1H), 1.36 (s, 3H), 1.25 (s, 3H). $^{13}$C NMR (100 MHz, D$_2$O) δ 178.10, 111.96, 83.32, 82.35, 81.89, 67.83, 55.98, 32.16, 24.79, 22.80.

Example 50a

Preparation of 2-((3aS,4R,6S,6aR)-4-amino-tetrahydro-2,2-dimethyl-3aH-cyclopenta[d][1,3]dioxol-6-yloxy)acetic acid Compound IV-a (10 g) was dissolved in ethanol (7V). Ammonium formate (1.72 g) and 10% Pd/C (1.0 g) were added. The reaction mixture was heated to 60-70° C. for 4 hours. The reaction mixture was filtered and the filtrate was concentrated to dryness at 40° C. to give compound V-a (6.0 g).

$^1$H NMR (400 MHz, D$_2$O): δ 4.96 (s, 2H), 4.04 (d, J=4 Hz, 1H), 3.97-3.88 (m, 2H), 3.64 (d, J=8 Hz, 1H), 2.31-2.25 (m, 1H), 2.04-2.00 (m, 1H), 1.85 (brs, 1H), 1.36 (s, 3H), 1.25 (s, 3H). $^{13}$C NMR (100 MHz, D$_2$O) δ 178.10, 111.96, 83.32, 82.35, 81.89, 67.83, 55.98, 32.16, 24.79, 22.80.

Example 51

Preparation of N-[4,6-dichloro-2-(propylthio)pyrimidin-5-yl]formamide

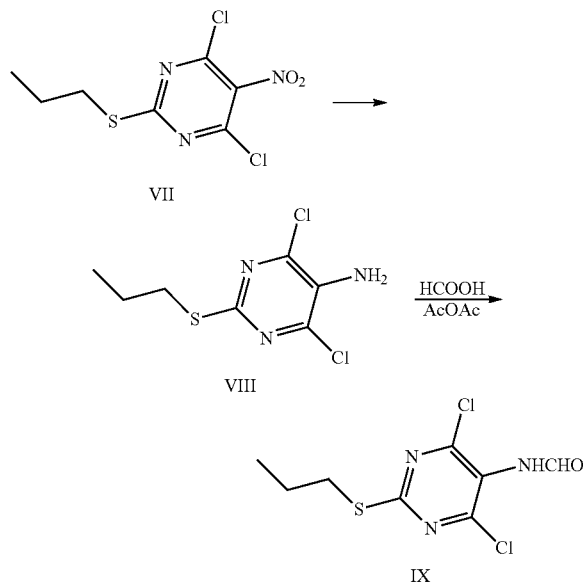

Iron powder (15.62 g) was added portionwise to a solution of compound VII (25 g) in methanol (5V) and acetic acid (3V) at <30° C. The resulting reaction mixture was stirred for 3-5 hrs at 35° C. The reaction mixture was then passed through a diatomaceous earth (Celite) pad. Water (400 mL) was added and the mixture was extracted with toluene (3×150 mL). The combined organic layer was washed with water (2×150 mL). The toluene layer was concentrated to half volume and added into a rb flask containing formic acid (51.5 mL). This mixture was cooled 0-5° C. and acetic anhydride (57.11 g) was added dropwise. The reaction mixture was allowed to come at room temperature and stirred 4-5 hrs at this temperature. The toluene layer was distilled off and the thus obtained solid product was crystallized from a mixture of cyclohexane and methyl-tert-butyl ether to give compound IX (22 g).

$^1$H NMR (400 MHz, CDCl$_3$): δ 8.40-8.31 (m, 1H), 7.10 (brs, 1H), 3.13 (t, J=8 Hz, 2H), 1.82-1.71 (m, 2H), 1.06 (t, J=8 Hz, 3H). $^1$H NMR (400 MHz, DMSO-D6): δ 8.25 (s, 1H), 3.05 (t, J=4 Hz, 2H), 1.80-1.46 (m, 2H), 0.924 (t, J=8 Hz, 3H); C NMR (100 MHz, DMSO-D6) δ 170.11, 164.93, 160.71, 159.71, 123.25, 33.33, 22.13, 13.53.

Example 52

Preparation of 2-(((3aR,4S,6R,6aS)-6-((6-chloro-5-formamido-2-(propylthio)pyrimidin-4-yl)amino)-2,2-dimethyltetrahydro-3aH-cyclopenta[d][1,3]dioxol-4-yl)oxy)acetic acid

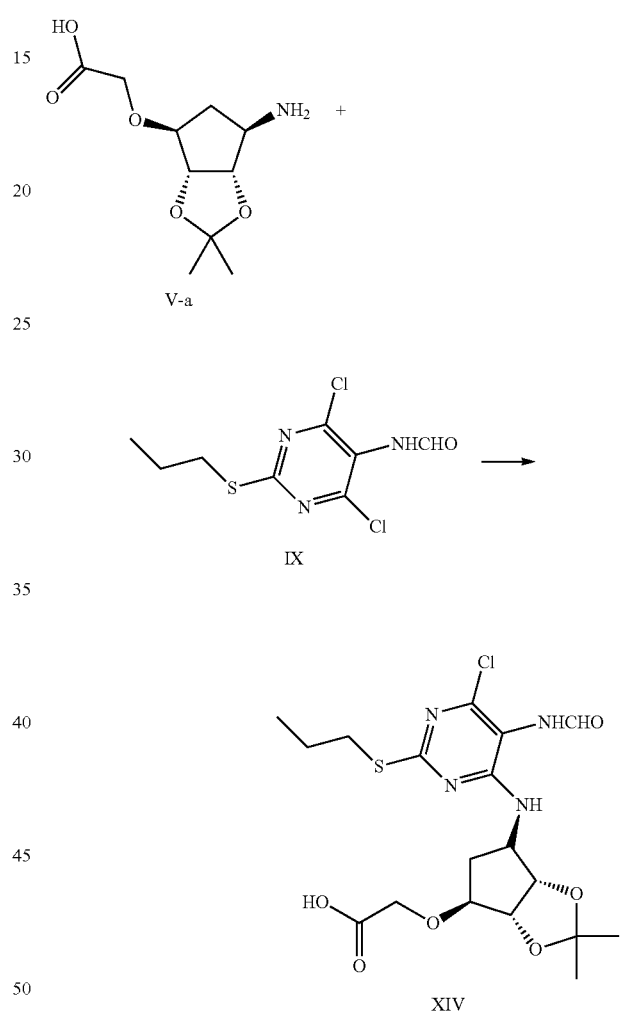

Compound V-a (35 g), compound IX (5.75 g) and ethanol (400 mL) were combined to form a mixture. Triethylamine (23 g) was added under an inert atmosphere. The reaction mixture was heated to 50-60° C. for 4-5 hrs. The ethanol layer was distilled off and the obtained residue was diluted with water (350 mL) and acidified to pH 2-3. The aqueous layer was then extracted with ethyl acetate (2×250 mL). The organic layer was distilled off under reduced pressure. The obtained residue (54.0 g) was used for next step without further purification.).

$^1$H NMR (400 MHz, DMSO-d$_6$): δ 9.49 (s, 1H), 8.18 (s, 1H), 6.94 (d, J=8 Hz, 1H), 4.57-4.38 (m, 3H), 4.22-3.97 (m, 3H), 3.11-2.98 (m, 2H), 2.24-2.10 (m, 1H), 1.85-1.82 (m, 1H), 1.74-1.63 (m, 2H)), 1.38 (s, 3H), 1.22 (s, 3H). $^{13}$C NMR (100 MHz, DMSO-d$_6$) δ 172.32, 168.70, 165.58, 161.21, 158.72, 155.31, 110.68, 108.29, 85.01, 84.59, 84.25, 83.30, 83.19, 66.75, 56.76, 33.89, 33.57, 32.87, 28.95, 26.77, 25.25, 24.57.

Example 53 methyl 2-(((1S,2S,3S,4R)-4-(7-chloro-5-(propylthio)-3H-[1,2,3]triazolo[4,5-d]pyrimidin-3-yl)-2,3-dihydroxycyclopentyl)oxy)acetate; via methyl 2-(((1S,2S,3S,4R)-4-((5-amino-6-chloro-2-(propylthio)pyrimidin-4-yl)amino)-2,3-dihydroxycyclopentyl)oxy)acetate

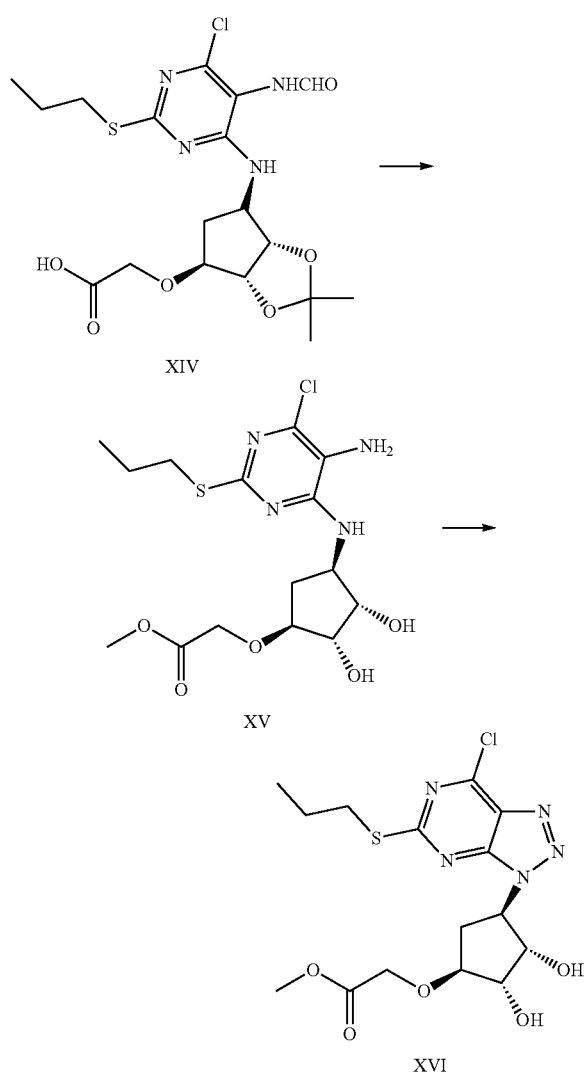

To a solution of compound XIV (54.0 g) and methanol (750 mL) was added aqueous hydrochloric acid (5M) solution (200 mL). The reaction mixture was stirred at 35° C. for 4-5 hrs. The reaction mixture was then cooled to 0-5° C. and a solution of sodium nitrite in water was added slowly dropwise. The reaction mixture was stirred at 0-5° C. for 1 hrs. The reaction mixture was then diluted with water (1500 mL) and extracted with ethyl acetate (500 mL). The organic layer was washed with brine n (300 mL), sodium bicarbonate solution (3×100 mL) and finally with brine (2×100 mL). The organic layer was then concentrated under reduced pressure to give compound XVI (41.0 g, 84%). This crude product was used for the next step without further purification.

Example 54

Methyl 2-(((1S,2S,3S,4R)-4-(7-(((1R,2S)-2-(3,4-difluorophenyl)-cyclopropyl)amino)-5-(propylthio)-3H-[1,2,3]triazolo[4,5-d]pyrimidin-3-yl)-2,3-dihydroxycyclopentyl)oxy)acetate

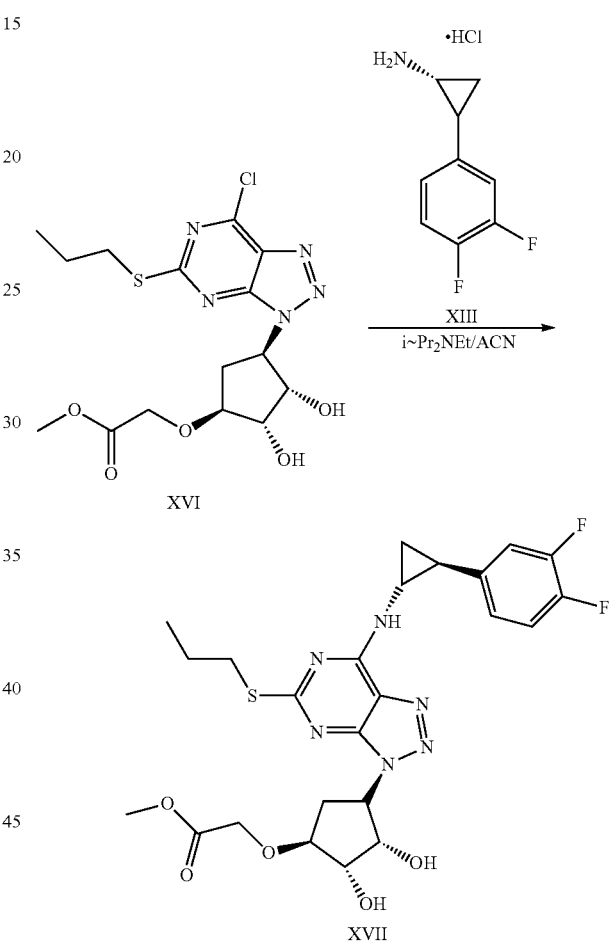

To a solution of compound XVI (40.0 g) in acetonitrile (5-10V) was added diisopropylethylamine (27.01 g). A solution of compound XIII (19.68 g) in acetonitrile (3-5 V) was added. The reaction mixture was stirred at 25-35° C. for 1-5 hours. The reaction was stopped by adding brine solution (250 mL) and the mixture was extracted with ethyl acetate (3×200 mL). The combined organic fraction was washed with brine (200 mL) and concentrated to dryness. The crude product was purified by crystallization from a mixture of MTBE and cyclohexane to give compound XVII (48 g, 91%).

$^1$H NMR (400 MHz, DMSO-$d_6$): δ 7.33-7.26 (m, 2H), 7.06 (m, 1H), 5.21-5.15 (m, 2H), 4.95-4.93 (m, 1H), 4.54 (m, 1H), 4.20 (s, 2H), 3.97 (brs, 1H), 3.82 (brs, 1H), 3.64 (s, 3H), 3.13-3.12 (m, 1H), 2.89-2.80 (m, 2H), 2.64-2.62 (m, 1H), 2.09-2.06 (m, 2H), 1.54-1.35 (m, 4H), 0.78 (t, J=8 Hz, 3H).

Example 54a

Methyl 2-(((1S,2S,3S,4R)-4-(7-(((1R,2S)-2-(3,4-difluorophenyl)-cyclopropyl)amino)-5-(propylthio)-3H-[1,2,3]triazolo[4,5-d]pyrimidin-3-yl)-2,3-dihydroxycyclopentyl)oxy)acetate To a solution of compound XVI (40.0 g) in acetonitrile (2.5V) was added diisopropylethylamine (27.01 g). A solution of compound XIII (19.68 g) in acetonitrile (2.5 V) was added. The reaction mixture was stirred at 25-35° C. for 1 hour. The reaction was stopped by adding brine solution (250 mL) and the mixture was extracted with ethyl acetate (3×200 mL). The combined organic fraction was washed with brine (200 mL) and concentrated to dryness. The crude product was purified by crystallization from a mixture of MTBE and cyclohexane to give compound XVII (48 g, 91%).

$^1$H NMR (400 MHz, DMSO-$d_6$): δ 7.33-7.26 (m, 2H), 7.06 (m, 1H), 5.21-5.15 (m, 2H), 4.95-4.93 (m, 1H), 4.54 (m, 1H), 4.20 (s, 2H), 3.97 (brs, 1H), 3.82 (brs, 1H), 3.64 (s, 3H), 3.13-3.12 (m, 1H), 2.89-2.80 (m, 2H), 2.64-2.62 (m, 1H), 2.09-2.06 (m, 2H), 1.54-1.35 (m, 4H), 0.78 (t, J=8 Hz, 3H),

Example 55

Preparation of (1S,2S,3R,5S)-3-(7-((1R,2S)-2-(3,4-difluorophenyl)cyclopropylamino)-5(propylthio)-3H-[1,2,3]triazolo[4,5-d]pyrimidin-3-yl)-5-(2-hydroxyethoxy)cyclopentane-1,2-diol (Ticagrelor)

Compound XVII (5 g) was dissolved in THF (5-10V). LiBH4 (0.592 g) was added portionwise at 0-5° C. The reaction mixture was stirred at room temperature for 4-8 hours. water (50 mL) was added. Ethyl acetate was added and the mixture was stirred for 10 min at RT. The aqueous and organic layers were separated and the aqueous layer was neutralized to pH 6-7. The aqueous layer was extracted with ethyl acetate (3×50 mL). The combined organic fraction was concentrated to dryness and the residue was purified by crystallization from MTBE/cyclohexane to give compound I, Ticagrelor (3.80 g).

Example 55a

Preparation of (1S,2S,3R,5S)-3-(7-((1R,2S)-2-(3,4-difluorophenyl)cyclopropylamino)-5 (propylthio)-3H-[1,2,3]triazolo[4,5-d]pyrimidin-3-yl)-5-(2-hydroxy-ethoxy)cyclo pentane-1,2-diol (Ticagrelor)

Compound XVII (5 g) was dissolved in THF (20V). LiBH$_4$ (0.592 g) was added portionwise at 0-5° C. The reaction mixture was stirred at room temperature for 2 hours. Water (50 mL) was added. Ethyl acetate (2×100 mL) was added and the mixture was stirred for 10 min at RT. The aqueous and organic layers were separated and the aqueous layer was neutralized to pH 6-7. The aqueous layer was extracted with ethyl acetate (3×50 mL). The combined organic fraction was concentrated to dryness and the residue was purified by crystallization from MTBE/cyclohexane to give Ticagrelor (3.80 g).

Example 56

Preparation of benzyl (3aR,4S,6R,6aS)-4-(2-hydroxyethoxy)-tetrahydro-2,2-dimethyl-3aH-cyclopenta[d][1,3]dioxol-6-ylcarbamate

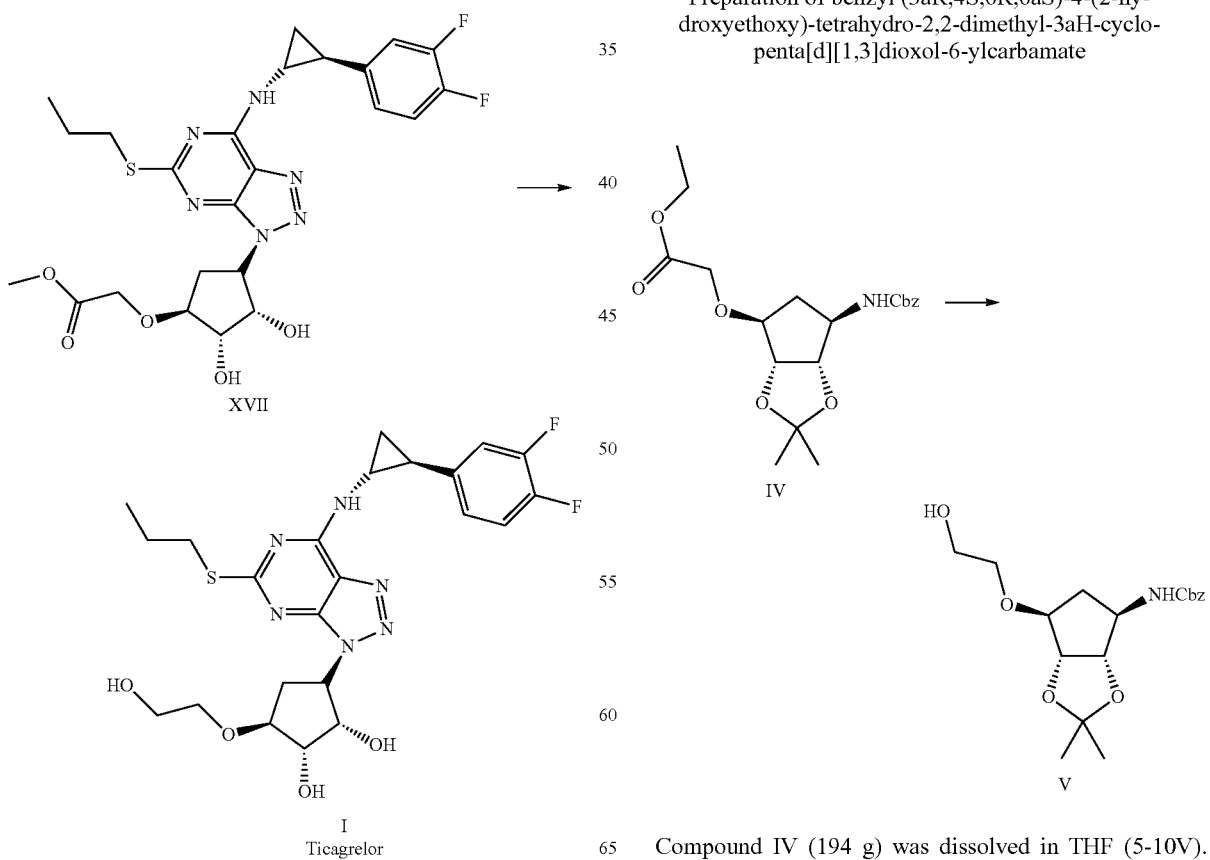

Compound IV (194 g) was dissolved in THF (5-10V). LiBH$_4$ (37.58 g) was added portionwise at 0-5° C. The reaction mixture was stirred at room temperature for 4-8 hours.

The reaction was quenched by adding a solution of acetic acid (388 mL) and water (970 mL). Then ethyl acetate was added and the mixture was stirred for 10 min at RT. The aqueous and organic layers were separated. The aqueous layer was neutralized to pH 6-7 with sat. NaHCO$_3$ solution and extracted with ethyl acetate (3×500 mL). The combined organic fraction was concentrated to dryness to provide compound V (155 g, 89%), which was used for the next step without further purification.

Example 56a

Preparation of benzyl (3aR,4S,6R,6aS)-4-(2-hydroxyethoxy)-tetrahydro-2,2-dimethyl-3aH-cyclopenta[d][1,3]dioxol-6-ylcarbamate Compound IV (194 g) was dissolved in THF (5V). Lithium borohydride (37.58 g) was added portionwise at 0-5° C. The reaction mixture was stirred at room temperature for 4 hours. The reaction was quenched by adding a solution of acetic acid (388 mL) and water (970 mL). Then ethyl acetate (500 mL) was added and the mixture was stirred for 10 min at RT. The aqueous and organic layers were separated. The aqueous layer was neutralized to pH 6-7 with sat. NaHCO$_3$ solution and extracted with ethyl acetate (3×500 mL). The combined organic fraction was concentrated to dryness to provide compound V (155 g, 89%), which was used for the next step without further purification.

Example 57

Preparation of 2-((3aS,4R,6S,6aR)-4-amino-tetrahydro-2,2-dimethyl-3aH-cyclopenta[d][1,3]dioxol-6-yloxy)ethanol, oxalic acid salt (1:1)

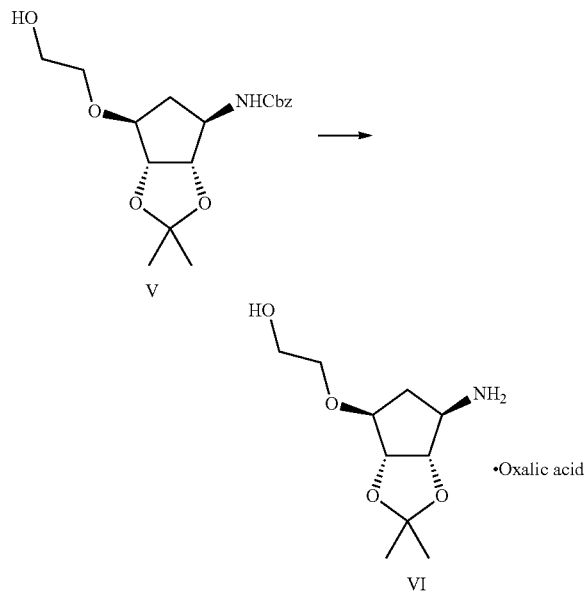

Compound V (70 g) was dissolved in ethanol (5-10V). Ammonium formate (12.56 g) and 10% Pd/C (7.0 g) were added. The reaction mixture was heated to 30-70° C. for 1-3 hours. The reaction mixture was filtered. The resulting filtrate and oxalic acid (25.11 g) was charged into a 1-liter RB flask. The resulting reaction mixture was heated to 50-70° C. for 1-4 hours. The reaction mixture was stirred at RT for 8-10 hrs. The ethanol was distilled off and THE residue was suspended in hexane. The suspension was filtered and the collected solid was dried to provide compound VI (60.23 g, 98%).

Example 57a

Preparation of 2-((3aS,4R,6S,6aR)-4-amino-tetrahydro-2,2-dimethyl-3aH-cyclopenta[d][1,3]dioxol-6-yloxy)ethanol, oxalic acid salt (1:1)

Compound V (70 g) was dissolved in ethanol (5V). Ammonium formate (12.56 g) and 10% Pd/C (7.0 g) were added. The reaction mixture was heated to 60-65° C. for 2.5 hours. The reaction mixture was filtered. The resulting filtrate and oxalic acid (25.11 g) was charged into a 1-liter RB flask. The resulting reaction mixture was heated to 60-65° C. for 16 hours. The reaction mixture was stirred at RT for 8-10 hrs. The ethanol was distilled off and THE residue was suspended in hexane. The suspension was filtered and the collected solid was dried to provide compound VI (60.23 g, 98%).

Example 58

Preparation of 2-((3aS,4R,6S,6aR)-4-amino-tetrahydro-2,2-dimethyl-3aH-cyclopenta[d][1,3]dioxol-6-yloxy)ethanol

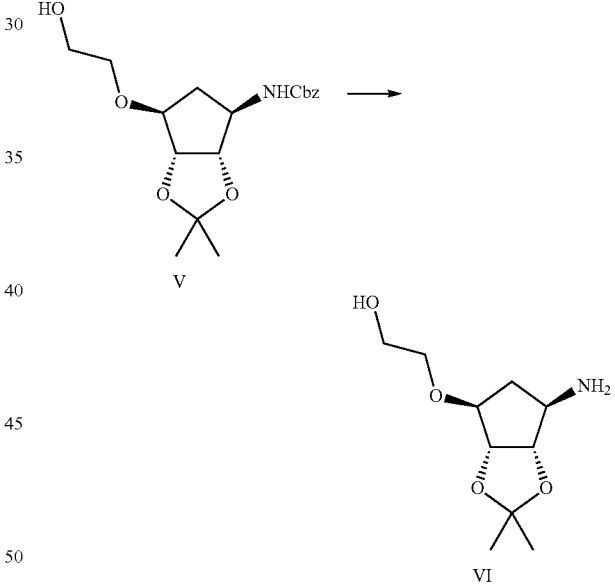

Compound V (70 g) was dissolved in ethanol (5-10V). Ammonium formate (12.56 g) and 10% Pd/C (7.0 g) were added. The reaction mixture was heated to 30-70° C. for 1-3 hours. The reaction mixture was filtered. The ethanol was distilled off and the resulting residue was isolated as dense oil as the free base (39.0 g, 90%).

Example 58a

Preparation of 2-((3aS,4R,6S,6aR)-4-amino-tetrahydro-2,2-dimethyl-3aH-cyclopenta[d][1,3]dioxol-6-yloxy)ethanol Compound V (90 g) was dissolved in ethanol (5V). Ammonium formate (16.5 g) and 10% Pd/C (9.0 g) were added. The

Example 59

Preparation of N-(4-chloro-6-(((3aS,4R,6S,6aR)-6-(2-hydroxyethoxy)-2,2-dimethyl tetrahydro-3aH-cyclopenta[d][1,3]dioxol-4-yl)amino)-2-(propylthio)pyrimidin-5-yl)formamide

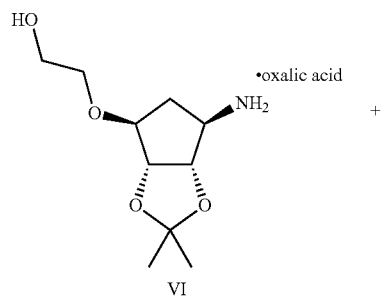

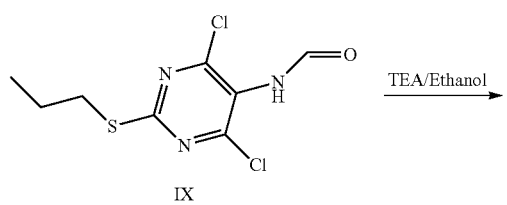

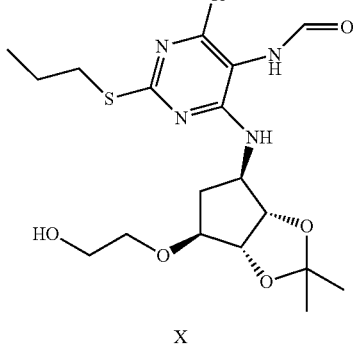

To a mixture of compound VI oxalic acid salt (20.0 g), compound IX (17.31 g) and ethanol (100 mL), was added triethylamine (26.34 g) under an inert atmosphere. The resulting reaction mixture was heated to 40-80° C. for 3-6 hrs. The reaction was monitored by TLC and HPLC. After completion of reaction, the ethanol was distilled off under reduced pressure. Water (280 mL) was added and the layers were separated. The aqueous layer was extracted with ethyl acetate (3×100 mL). The organic layer was distilled off at 40° C. under reduced pressure. The thus obtained residue was crystallized from a mixture of methyl-tertbutyl ether and diisopropyl ether to give compound X (25.0 g, 86%).

$^1$H NMR (400 MHz, CDCl$_3$): δ 8.31 (s, 1H), 7.51 (s, 1H), 6.57-6.14 (m, 1H), 4.58-4.48 (m, 1H), 3.94-3.88 (m, 1H), 3.79-3.68 (m, 4H), 3.61-3.57 (m, 1H), 3.39 (brs, 1H), 3.16-3.11 (m, Hi), 3.06-2.99 (m, 1H), 2.29-2.24 (m, 1H), 1.92-1.72 (m, 3H), 1.43 (s, 3H), 1.27 (s, 3H), 1.03 (t, J=8 Hz, 3H).

Example 59

Preparation of N-(4-chloro-6-(((3aS,4R,6S,6aR)-6-(2-hydroxyethoxy)-2,2-dimethyl tetrahydro-3aH-cyclopenta[d][1,3]dioxol-4-yl)amino)-2-(propylthio)pyrimidin-5-yl)formamide To a mixture of compound VI oxalic acid salt (20.0 g), compound IX (17.31 g) and ethanol (100 mL), was added triethylamine (26.34 g) under an inert atmosphere. The resulting reaction mixture was heated to 60° C. for 4 hrs. The reaction was monitored by TLC and HPLC. After completion of reaction, the ethanol was distilled off under reduced pressure. Water (280 mL) was added and the layers were separated. The aqueous layer was extracted with ethyl acetate (3×100 mL). The organic layer was distilled off at 40° C. under reduced pressure. The thus obtained residue was crystallized from a mixture of methyl-tertbutyl ether and diisopropyl ether to give compound X (25.0 g, 86%).

$^1$H NMR (400 MHz, CDCl$_3$): δ 8.31 (s, 1H), 7.51 (s, 1H), 6.57-6.14 (m, 1H), 4.58-4.48 (m, 1H), 3.94-3.88 (m, 1H), 3.79-3.68 (m, 4H), 3.61-3.57 (m, 1H), 3.39 (brs, 1H), 3.16-3.11 (m, 1H), 3.06-2.99 (m, 1H), 2.29-2.24 (m, 1H), 1.92-1.72 (m, 3H), 1.43 (s, 3H), 1.27 (s, 3H), 1.03 (t, J=8 Hz, 3H).

Example 60

Preparation of N-(4-chloro-6-(((3aS,4R,6S,6aR)-6-(2-hydroxyethoxy)-2,2-dimethyltetrahydro-3aH-cyclopenta[d][1,3]dioxol-4-yl)amino)-2-(propylthio)pyrimidin-5-yl)formamide reaction mixture was heated to 60-65° C. for 3 hours. The reaction mixture was filtered. The ethanol was distilled off and the resulting residue was isolated as dense oil as the free base (55 g).

-continued

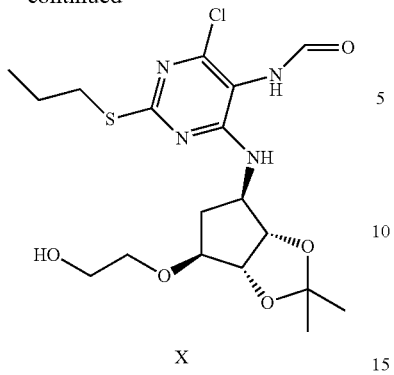

X

To a mixture of compound VI free base (20.0 g), compound IX (24.49 g) and ethanol (240 mL) was added triethylamine (9.31 g) under an inert atmosphere. The resulting reaction mixture was heated to 40-80° C. for 3-6 hrs. The reaction was monitored by TLC and HPLC. After completion of reaction, ethanol was distilled off under reduced pressure. Water (280 mL) was added and the layers were separated. The aqueous layer was extracted with ethyl acetate (3×100 mL). The organic layer was distilled off at 40° C. under reduced pressure. The thus obtained residue was crystallized from a mixture of methyl-tertbutyl ether and diisopropyl ether to give compound X (35.0 g).

Example 60a

Preparation of N-(4-chloro-6-(((3aS,4R,6S,6aR)-6-(2-hydroxyethoxy)-2,2-dimethyltetrahydro-3aH-cyclopenta[d][1,3]dioxol-4-yl)amino)-2-(propylthio)pyrimidin-5-yl)formamide To a mixture of compound VI free base (50.0 g), compound IX (58.17 g) and ethanol (500 mL) was added triethylamine (34.93 g) under an inert atmosphere. The resulting reaction mixture was heated to 60° C. for 5 hrs. The reaction was monitored by TLC and HPLC. After completion of reaction, ethanol was distilled off under reduced pressure. Water (500 mL) was added and the layers were separated. The aqueous layer was extracted with ethyl acetate (3×250 mL). The organic layer was distilled off at 40° C. under reduced pressure. The thus obtained residue was crystallized from a mixture of methyl-tert-butyl ether and diisopropyl ether to give compound X (69.82 g).

Example 61

Preparation of (1S,2S,3R,5S)-3-(7-chloro-5-(propyl-sulfanyl-triazolo) [4,5-d]pyrimidin-3-yl)-5-(2-hydroxyethoxy)cyclopentane-1,2-diol (XII) via (1S,2S,3S,5R)-3-(2-hydroxyethoxy)-5-(5-amino-6-chloro-2-(propylthio)pyrimidin-4-ylamino)cyclopentane-1,2-diol (XI)

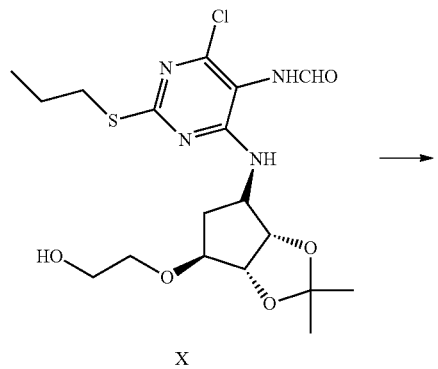

X

-continued

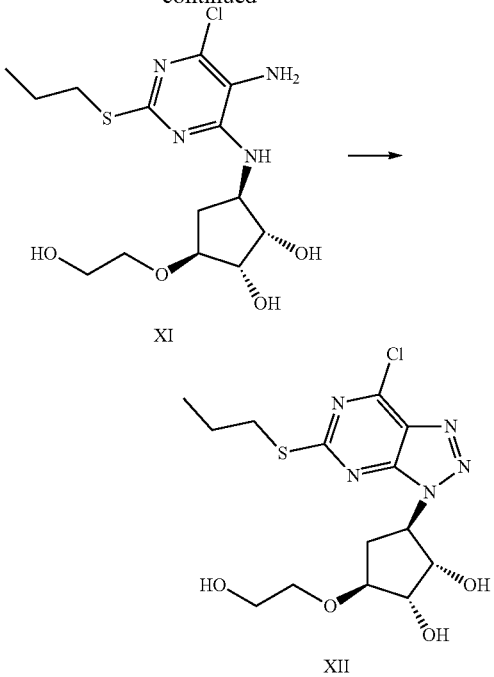

XI

XII

To a solution of compound X (31.0 g) in methanol (250 mL) was added aqueous hydrochloric acid (5M) solution (124 mL). The reaction mixture was stirred at 35° C. for 4-5 hrs. The reaction mixture was cooled to 0-5° C. and sodium nitrite (6.13 g) was dissolved in water (11 mL) and added to the reaction mixture slowly dropwise. The reaction mixture was stirred at 0-5° C. for 1 hr. The reaction mixture was diluted with water (100 mL) and extracted with ethyl acetate (250 mL). The organic layer was washed with brine (100 mL), sodium bicarbonate solution (100 mL) and finally with brine (100 mL). The organic layer was distilled off under reduced pressure and the resulting residue was crystallized from MTBE to give compound XII (24.5.g, 90%).

$^1$H NMR (400 MHz, DMSO-d$_6$): δ 5.11 (q, J=8 Hz, 1H), 3.96 (d, J=4 Hz, 1H), 3.78-3.76 (m, 1H), 3.53-3.43 (m, 4H), 3.25-3.14 (m, 2H), 2.75-2.67 (m, 1H), 1.78-1.69 (m, 2H), 0.99 (t, J=8 Hz, 3H). $^{13}$C NMR (100 MHz, DMSO-d$_6$) δ$^{170.10}$, 152.27, 151.21, 132.33, 82.13, 75.03, 74.09, 71.32, 62.48, 60.75, 33.51, 33.35, 22.20, 13.62.

Example 62

Preparation of (1S,2S,3R,5S)-3-(7-((1R,2S)-2-(3,4-difluorophenyl)cyclopropylamino)-5(propylthio)-3H-[1,2,3]triazolo[4,5-d]pyrimidin-3-yl)-5-(2-hydroxyethoxy)cyclopentane-1,2-diol (Ticagrelor)

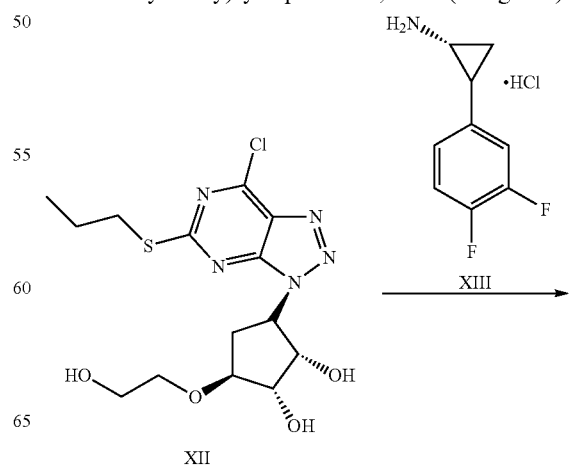

XII

-continued

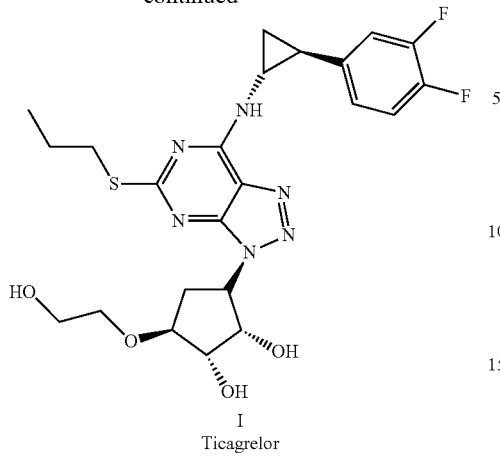

I
Ticagrelor

To a solution of compound XIII (5.80 g) in acetonitrile (5-10V) was added diisopropylethylamine (7.63 g). A solution of compound XII (10 g) in acetonitrile (3-5 V) was added. The reaction mixture was stirred at 25-35° C. for 1-5 hours. The reaction was stopped by adding brine solution (250 mL) and the resulting mixture was extracted with ethyl acetate (3×200 mL). The combined organic fraction was washed with brine (200 mL) and concentrated to dryness. The crude product was purified by crystallization from a mixture of MTBE and cyclohexane to give the product (12.8 g, 95.5%).

Example 62a

Preparation of (1S,2S,3R,5S)-3-(7-((1R,2S)-2-(3,4-difluorophenyl)cyclopropylamino)-5(propylthio)-3H-[1,2,3]triazolo[4,5-d]pyrimidin-3-yl)-5-(2-hydroxyethoxy)cyclopentane-1,2-diol (Ticagrelor)

To a solution of compound XIII (5.80 g) in acetonitrile (5V) was added diisopropylethylamine (7.63 g). A solution of compound XII (10 g) in acetonitrile (5 V) was added. The reaction mixture was stirred at 25-35° C. for 1 hour. The reaction was stopped by adding brine solution (250 mL) and the resulting mixture was extracted with ethyl acetate (3×200 mL). The combined organic fraction was washed with brine (200 mL) and concentrated to dryness. The crude product was purified by crystallization from a mixture of MTBE and cyclohexane to give the product (12.8 g, 95.5%).

Example 63

Preparation of (1S,2S,3R,5S)-3-(7-((1R,2S)-2-(3,4-difluorophenyl)cyclopropylamino)-5 (propylthio)-3H-[1,2,3]triazolo[4,5-d]pyrimidin-3-yl)-5-(2-hydroxyethoxy)cyclopentane-1,2-diol (Ticagrelor)

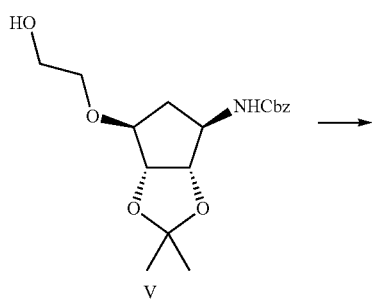

V

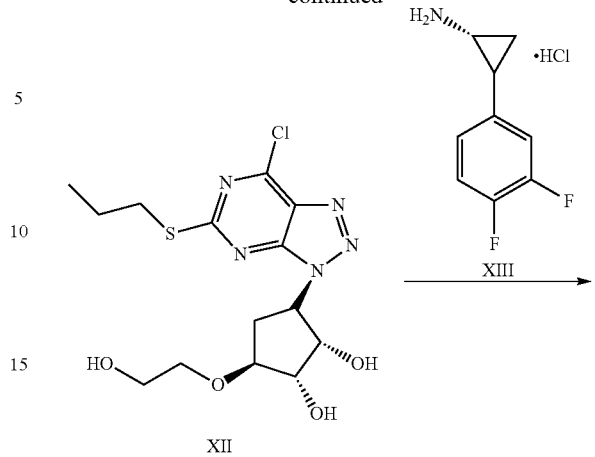

I
Ticagrelor

Compound V (25 g) is dissolved in ethanol (5-10V). Ammonium formate (4.48 g) and 10% Pd/C (2.5 g) are added. The reaction mixture is heated to 30-70° C. for 1-3 hours. The reaction mixture is filtered and the filtrate is added to a 1-Liter rb flask. Compound IX (15.15 g) and triethylamine (7.20 g) are added under an inert atmosphere. The resulting reaction mixture is heated to 40-80° C. for 3-6 hrs. The reaction is monitored by TLC and HPLC. When the reaction is complete, aqueous hydrochloric acid (5M) solution (60 mL) is added. The reaction mixture is stirred at 35° C. for 4-5 hrs. The reaction mixture is then cooled to 0-5° C. and sodium nitrite (5.89 g) is dissolved in water (12 mL) and added to the reaction mixture slowly dropwise. The reaction mixture is stirred at 0-5° C. for 1 hr. The reaction mixture is then diluted with water (100 mL) and extracted with ethyl acetate (250 mL). The organic layer is washed with brine (100 mL), sodium bicarbonate solution (100 mL) and finally with brine (100 mL). The organic layer is concentrated under reduced pressure and the resulting residue is crystallized from MTBE to provide compound XII (22.46 g, 81%).

We claim:

1. A process of preparing Ticagrelor according to Formula I:

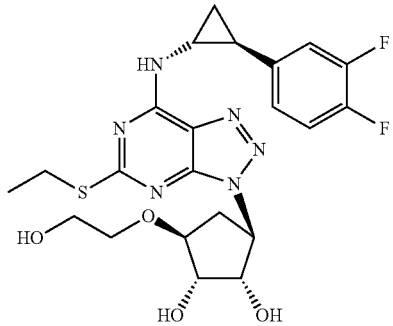

I said process comprising coupling a compound according to Formula VI:

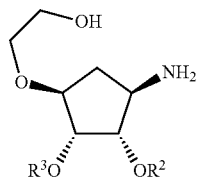

VI wherein $R^2$ and $R^3$ are independently selected from —H, optionally substituted —Si($C_{1-6}$ alkyl)$_3$, optionally substituted —C(=O)—$C_{1-6}$alkyl, and optionally substituted —C(=O)—O$C_{1-6}$ alkyl; alternatively, $R^2$ and $R^3$ together form an alkylidene group, or an alkoxymethylidene group, each optionally substituted with 1, 2 or 3 substituents independently selected from —$C_1$-$C_8$ alkyl or —$C_6$-$C_8$ aryl; or $R^2$ and $R^3$ together with the attached oxygen atoms and the carbon atoms to which the oxygen atoms attached form a heterocyclic ring:

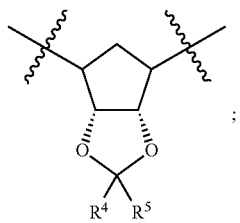

wherein $R^4$ and $R^5$ are independently selected from —H, —$C_{1-6}$ alkyl, and —$C_{6-10}$ aryl; or $R^4$ and $R^5$ together form a 5 to 6 membered spiro-fused carbocyclic ring, which is optionally substituted by 1, 2 or three substituents independently selected from —$C_1$-$C_6$ alkyl; —$C_6$-$C_{10}$ aryl and —$C_6$-$C_{10}$ aryl-$C_1$-$C_3$ alkyl; wherein said carbocyclic ring is optionally substituted by 1, 2 or 3 substituents independently selected from —$C_1$-$C_6$ alkyl, $C_6$-$C_{10}$ aryl, and $C_6$-$C_{10}$ aryl-$C_1$-$C_3$ alkyl;

with a compound according to Formula IX:

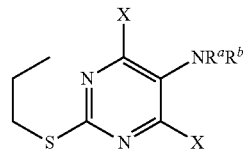

IX wherein each X is independently a halogen; $R^a$ is —H; and $R^b$ is an amino protecting group; to produce a compound according to Formula X:

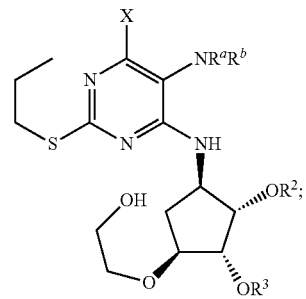

X and
converting the compound of Formula X to a compound according to Formula I with method A, method B, method C or method D,
wherein method A comprises
deprotecting the amino group —$NR^aR^b$ in the compound of Formula X to form the compound of Formula XIc:

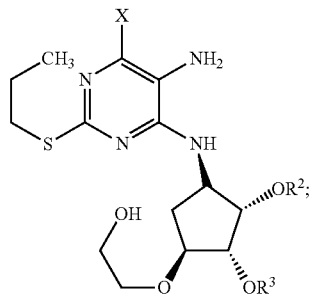

Formula XIc diazotizing the compound of Formula XIc to form the compound of Formula XIIc:

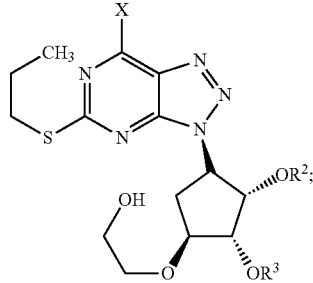

Formula XIIc coupling the compound of Formula XIIc with ((1R,2S)-2-(3,4-difluorophenyl)cyclopropanamine) to form the compound of Formula XX:

Formula XX

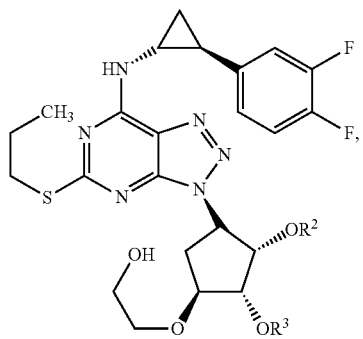

wherein the compound of Formula XX is Ticagrelor when both R² and R³ are H; and optionally converting the compound of Formula XX to Ticagrelor when R² and R³ are not both H by deprotection of the —OR² and/or —OR³ in the compound of Formula XX;

wherein method B comprises deprotecting the amino group —NR$^a$R$^b$ and deprotecting the —OR² and/or —OR³ in the compound of Formula X to form the compound of Formula XId:

Formula XId

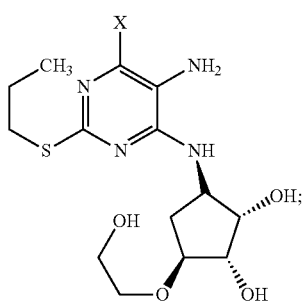

diazotizing the compound of Formula XId to form the compound of Formula XIId:

Formula XIId

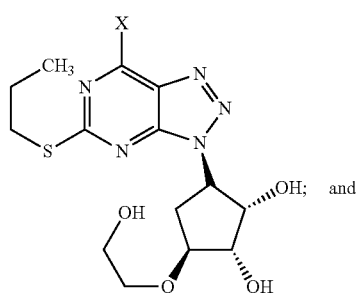

coupling the compound of Formula XIId with ((1R,2S)-2-(3,4-difluorophenyl)cyclopropanamine) to form Ticagrelor;

wherein method C comprises deprotecting the —OR² and/or —OR³ in the compound of Formula X to form the compound of Formula XIX;

Formula XIX

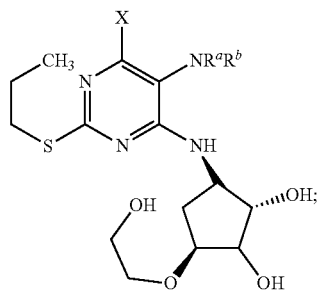

deprotecting the amino group —NR$^a$R$^b$ in the compound of Formula XIX to form the compound of Formula XId:

Formula XId

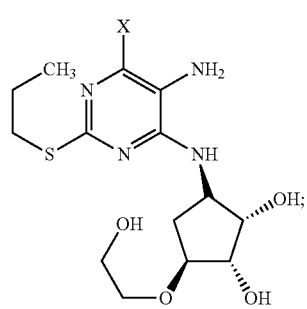

diazotizing the compound of Formula XId to form the compound of Formula XIId:

Formula XIId

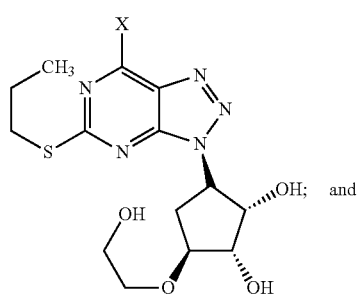

coupling the compound of Formula XIId with ((1R,2S)-2-(3,4-difluorophenyl)cyclopropanamine) to form Ticagrelor; and wherein method D comprises deprotecting the amino group —NR$^a$R$^b$ in the compound of Formula X to form the compound of Formula XIc:

Formula XIc

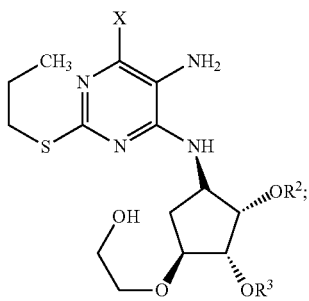

diazotizing the compound of Formula XIc to form the compound of Formula XIIc:

Formula XIIc

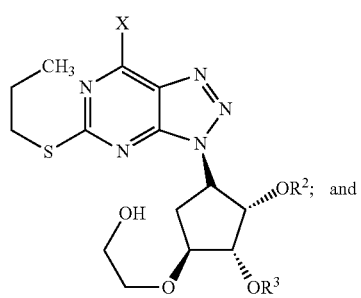

deprotecting the —OR² and/or —OR³ group and coupling the compound with ((1R,2S)-2-(3,4-difluorophenyl)cyclopropanamine) to form Ticagrelor.

2. The process according to claim 1, wherein the compound of Formula X is N-(4-chloro-6-(((3 aS,4R,6S,6aR)-6-(2-hydroxyethoxy)-2,2-dimethyl tetrahydro-3aH-cyclopenta-[d][1,3]dioxol-4-yl)amino)-2-(propylthio) pyrimidin-5-yl) formamide, or N-(4-chloro-6-((3 aR,4S,6R,6 aS)-4-(2-hydroxyethoxyl)tetrahydro-3aH-spiro[cyclopenta-[d][1,3]dioxole-2,1'-cyclopentane]-6-ylamino)-2-(propylthio) pyrimidin-5-yl)formamide.

3. The process according to claim 1, wherein converting the compound of Formula X to a compound of Formula I comprises a step of coupling a compound of Formula XII:

XII

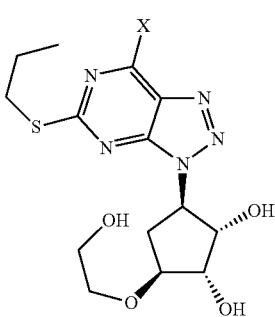

wherein X is a halogen, with (1R,2S)-2-(3,4-difluorophenyl)cyclopropanamine) to produce the compound Ticagrelor.

4. A process of preparing Ticagrelor, comprising:
a. coupling compound of Formula VI:

VI

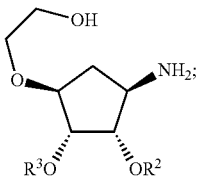

wherein R² and R³ are independently selected from —H, optionally substituted —Si(C$_{1-6}$ alkyl)$_3$, optionally substituted —C(=O)—C$_{1-6}$alkyl, and optionally substituted —C(=O)—OC$_{1-6}$ alkyl; alternatively, R² and R³ together form an alkylidene group, or an alkoxymethylidene group, each optionally substituted with 1, 2 or 3 substituents independently selected from —C$_1$-C$_8$ alkyl or —C$_6$-C$_8$ aryl; or R² and R³ together with the attached oxygen atoms and the carbon atoms to which the oxygen atoms attached form a heterocyclic ring:

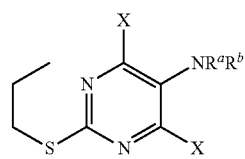

wherein R⁴ and R⁵ are independently selected from —H, —C$_{1-6}$ alkyl, and —C$_{6-10}$ aryl; or R⁴ and R⁵ together form a 5 to 6 membered spiro-fused carbocyclic ring, which is optionally substituted by 1, 2 or three substituents independently selected from —C$_1$-C$_6$ alkyl; —C$_6$-C$_{10}$ aryl and —C$_6$-C$_{10}$ aryl-C$_1$-C$_3$ alkyl; wherein said carbocyclic ring is optionally substituted by 1, 2 or 3 substituents independently selected from —C$_1$-C$_6$ alkyl, C$_6$-C$_{10}$ aryl, and C$_6$-C$_{10}$ aryl-C$_1$-C$_3$ alkyl;

with a compound of Formula IX:

IX wherein X is a leaving group; Ra is —H; and R$^b$ is an amino protecting group;

to produce a compound of Formula X;

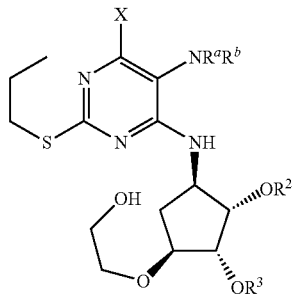

b) hydrolyzing the Formula X compound to produce a compound of Formula XI:

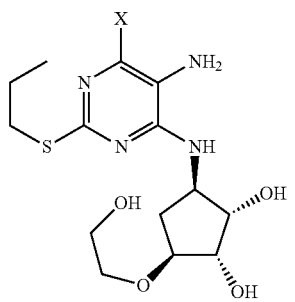

c) diazotizing the Formula XI compound to produce a compound of Formula XII:

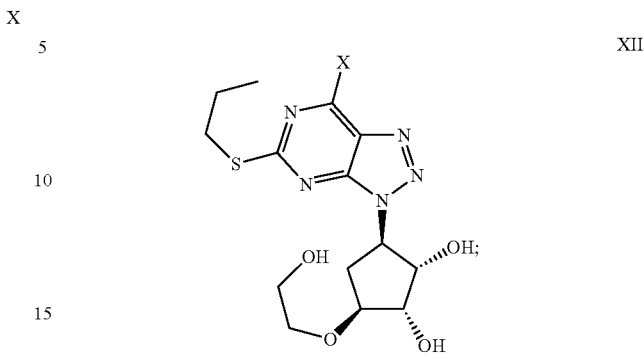

d) reacting the Formula XII compound with (1R,2S)-2-(3,4-difluorophenyl)cyclopropanamine, to produce Ticagrelor.

5. A process of preparing Ticagrelor according to claim 1, wherein the compound of Formula X is converted to the compound according to Formula I with method A.

6. A process of preparing Ticagrelor according to claim 1, wherein the compound of Formula X is converted to the compound according to Formula I with method B.

7. A process of preparing Ticagrelor according to claim 1, wherein the compound of Formula X is converted to the compound according to Formula I with method C.

8. A process of preparing Ticagrelor according to claim 1, wherein the compound of Formula X is converted to the compound according to Formula I with method D.

* * * * *